US005928887A

United States Patent [19]

Cheng et al.

[11] Patent Number: 5,928,887

[45] Date of Patent: Jul. 27, 1999

[54] κ/μ-LIKE PROTEIN TYROSINE PHOSPHATASE, PTP λ

[75] Inventors: Jill Cheng, Burlingame; Laurence A. Lasky, Saulito, both of Calif.

[73] Assignee: Genentech, Inc., S. San Francisco, Calif.

[21] Appl. No.: 08/991,258

[22] Filed: Dec. 16, 1997

Related U.S. Application Data

[62] Division of application No. 08/652,971, May 24, 1996, Pat. No. 5,814,507.

[51] Int. Cl.[6] .............................. C12Q 1/42; C12N 9/16; C07H 21/04

[52] U.S. Cl. ............................ 435/21; 435/196; 536/23.2

[58] Field of Search ..................... 435/21, 196; 536/23.2

[56] References Cited

FOREIGN PATENT DOCUMENTS

94/24161 10/1994 WIPO .

OTHER PUBLICATIONS

Cheng, J., et al., "A Novel Protein–Tyrosine Phosphatase Related to the Homotypically Adhering κ and μ Receptors", *The Journal of Biological Chemistry*, vol. 272, No. 11, pp. 7264–7277 (Mar. 14, 1997).

Maher, Pamela A., "Tissue–dependent Regulation of Protein Tyrosine Kinase Activity during Embryonic Development", *The Journal of Cell Biology*, vol. 112, No. 5 (Mar. 1991).

Tonks, N.K., "Introduction: Protein Tyrosine Phosphatases," *Seminars in Cell Biology*, 4:373–377 (1993).

Walton, K.M. and J.E. Dixon, "Protein Tyrosine Phosphatases," *Annu. Rev. Biochem.* 62:101–120 (1993).

Sun, H., and N.K. Tonks, "The Coordinated Action of Protein Tyrosine Phosphatases and Kinases i Signaling," *TIBS,* 19(11):480–485 (1994).

Brady–Kalnay, S.M., and N.K. Tonks, "Protein Tyrosine Phosphatases as Adhesion Receptors," *Curr Opinion in Cell Biology*, 7:650–657 (1995).

Beckman, G and P. Bork, "An Adhesive Domain Detected in Functionally Diverse Receptors," *TIBS*, 41 (1993).

Jiang, Y.–P., et al., "Cloning and Characterization of R–PTP–k, a New Member of the Receptor Prot Tyrosine Phosphatase Family with a Proteolytically Cleaved Cellular Adhesion Molecule–Like Extrac Region," *Molecular and Cellular Biology*, 13(5):2942–2951 (1993).

Gebbink, M.F.B.G., et al., "Cloning, Expression and Chromosomal Localization of a New Putative Receptor–Like Protein Tyrosine Phosphatase," *FEBS*, 290(1,2):123–130 (1991).

Brady–Kalnay, S.M., et al., "Homophilic Binding of PTPμ, a Receptor–Type Protein Tyrosine Phosph Can Mediate Cell–Cell Aggregation," *J.Cell. Biol.*, 122(4):961–972 (1993).

Gebbink, M.F.B.G., et al., "Cell–Cell Adhesion Medicated by a Receptor–Like Protein Tyrosine Phosphatase," *The Journal of Biological Chemistry*, 268(22):16101–16104 (1993).

Sap, J., et al., "Receptor Tyrosine Phosphatase R–PTP–k Mediates Homophilic Binding," *Molecular Cellular Biology*, 14(1):1–9 (1994).

Brady–Kalnay, S.N., and N.K. Tonks, "Identification of the Homophilic Binding Site of the Receptor Tyrosine Phosphataes PTPμ*," *The Journal of Biological Chemistry*, 269(45):28472–28477 (1994).

Zondag, G.C.M., "Homophilic Interactions Mediated by Receptor Tyrosine Phosphatases μ and κ," *Journal of Biological Chemistry*, 270(24):14247–14250 (1995).

Brady–Kalnay, S.M., et al., "Receptor Protein Tyrosine Phosphatase PTPμ Associates with Cadherin Catenins In Vivo," *J. Cell. Biol.*, 130(4):977–986 (1995).

Fang, K.S., et al., "A Transmembrane Protein–Tyrosine Phosphatase Contains Spectrin–Like Repeat Extracellular Domain," *The Journal of Biological Chemistry*, 269(19):14056–14063 (1994).

Kaplan, R., et al., "Cloning of Three Human Tyrosine Phosphatases Reveals a Multigene Family of Receptor–Linked Protein–Tyrosine–Phosphatases Expressed in Brain," PNAS USA, 87:7000–7004 (1990).

*Primary Examiner*—Robert A. Wax
*Assistant Examiner*—Einar Stole
*Attorney, Agent, or Firm*—Walter H. Dreger; Mark T. Kresnak, Ph.D.; Flehr Hohbach Test Albritton and Herbert LLP

[57] ABSTRACT

This invention concerns novel receptor protein tyrosine phosphatase polypeptides. Specifically, this invention concerns the novel receptor protein tyrosine phosphatase λ which is related to the homotypically adhering receptor protein tyrosine phosphatases κ and μ. The invention further relates to analogs of these polypeptides in other mammals, functional derivatives thereof, antibodies which are capable of specifically binding to these polypeptides, nucleic acids encoding these polypeptides, vectors containing and capable of expressing such nucleic acid and recombinant host cells transformed with such nucleic acid. Methods for the recombinant production of these receptor protein tyrosine phosphatase polypeptides and assays for identifying agonists and antagonists of these polypeptides are also within the scope of the invention.

4 Claims, 23 Drawing Sheets

```
  1 GTTGACTACT CAGCTGCCAG AACATCCAAT CTGGCTCCTG CAACTTTAGA CCAACATATT GTGTTTGATC

 71 TTCTCCTGAA CAACTTGGGA GATACGTCTG ATCTTCAGCT TGGTACATAC AGTTGCGCAG TGAATGGCAC

141 TTACGTGTTC ATTGTGCACA TGCTAAAGCT GGCATGATTA ATGTTCGACT GCTATGTCAA CCTGATTAAC

211 AATGAGGATG TCTTGGTGTC AGCTATGCCA ACGATGGTGC TCCAGACCGG CGCCAGTCCC GCTCCGCGCG

281 GCACTGTCCA CTACGGCTCC CGCTCGCCTT GGGCTCCCGG TCGGGCTCCG GAGGCGTCGC CTCCCCAGCT

351 GCGGGTCTCC AGGACCTAGG CGGCGGCC   ATG GCC CGG GCT CAG GCT CTG GTC CTG GCG CTC
  1                                 M   A   R   A   Q   A   L   V   L   A   L

412 ACC TTC CAG TTC TGC GCG CCT GAG ACC GAG ACT CCC GCA GCT GGC TGC ACC TTC GAG
 12 T   F   Q   F   C   A   P   E   T   E   T   P   A   A   G   C   T   F   E

469 GAG GCG AGT GAC CCG GTC GTG CCC TGC GAG TTC AGC CAG GCT CAG TAT GAC GAC TTC
 31 E   A   S   D   P   V   V   P   C   E   F   S   Q   A   Q   Y   D   D   F

526 CAA TGG GAG CAA GTG CGG ATC CAC CCC GGC ACC CGG ACC CCT GAA GAC CTG CCC CAT
 50 Q   W   E   Q   V   R   I   H   P   G   T   R   T   P   E   D   L   P   H

583 GGT GCC TAC TTG ATG GTC AAT GCT TCT CAG CAT ACC CCA GGT CAG AGG GCC CAC ATC
 69 G   A   Y   L   M   V   N   A   S   Q   H   T   P   G   Q   R   A   H   I

640 ATC TTC CAG ACC CTG AGC GAG AAC GAC ACC CAT TGT GTG CAG TTC AGC TAC TTC CTG
 88 I   F   Q   T   L   S   E   N   D   T   H   C   V   Q   F   S   Y   F   L

697 TAC AGC AGG GAT GGG CAC AGC CCA GGC ACC CTG GGG GTC TAC GTG CGC GTG AAT GGG
107 Y   S   R   D   G   H   S   P   G   T   L   G   V   Y   V   R   V   N   G
```

FIG._1A

```
754  GGC CCT CTG GGC AGT GCC GTG TGG AAT ATG ACC GGA TCC CAC GGC CGT CAG TGG CAC
126  G   P   L   G   S   A   V   W   N   M   T   G   S   H   G   R   Q   W   H

811  CAG GCT GAG CTG GCT GTC AGC ACC TTC TGG CCC AAT GAG TWT CAG GTG CTG TTT GAG
145  Q   A   E   L   A   V   S   T   F   W   P   N   E   X   Q   V   L   F   E

868  GCC CTC ATC TCC CCA GAC CAC AAG GGC TAC ATA GGC TTA GAC GAC ATC TTG CTC TTC
164  A   L   I   S   P   D   H   K   G   Y   I   G   L   D   D   I   L   L   F

925  AGC TAT CCC TGC GCA AAG GCC CCT CAC TTC TCC CGC CTT GGG GAC GTG GAG GTC AAT
183  S   Y   P   C   A   K   A   P   H   F   S   R   L   G   D   V   E   V   N

982  GCA GGC CAG AAC GCA TCC TTC CAA TGC ATG GCA GCA GGC AGA GCC GCA GAG GCA GAA
202  A   G   Q   N   A   S   F   Q   C   M   A   A   G   R   A   A   E   A   E

1039 CAC TTC TTC CTG CAG CGT CAG AGT GGA GTG CTG GTG CCT GCG GCC GGG GTG CGG CAC
221  H   F   F   L   Q   R   Q   S   G   V   L   V   P   A   A   G   V   R   H

1096 ATC AGT CAC CGT CGC TTC CTG GCC ACT TTT CCG CTG GCC TCG GTA GGC CGC TCA GAG
240  I   S   H   R   R   F   L   A   T   F   P   L   A   S   V   G   R   S   E

1153 CAG GAT CTG TAC CGT TGC GTG TCC CAG GCC CCG CGT GGT GCT GGC GTC TCC AAC TTT
259  Q   D   L   Y   R   C   V   S   Q   A   P   R   G   A   G   V   S   N   F

1210 GCA GAG CTC ATC GTC AAA GAG CCT CCC ACC CCC ATC GCG CCC CCA CAG CTG CTG CGT
278  A   E   L   I   V   K   E   P   P   T   P   I   A   P   P   Q   L   L   R

1267 GCA GGC CCC ACC TAC CTC ATT ATC CAG CTC AAC ACC AAC TCC ATC ATT GGC GAC GGG
297  A   G   P   T   Y   L   I   I   Q   L   N   T   N   S   I   I   G   D   G
```

FIG._1B

```
1324 CCG ATC GTG CGC AAG GAG ATC GAG TAC CGC ATG GCA CGG GGC CCG TGG GCC GAG GTG
 316 P   I   V   R   K   E   I   E   Y   R   M   A   R   G   P   W   A   E   V

1381 CAC GCT GTC AAC CTG CAR ACC TAC AAG CTG TGG CAT CTG GAC CCA GAC ACT GAG TAT
 335 H   A   V   N   L   Q   T   Y   K   L   W   H   L   D   P   D   T   E   Y

1438 GAA ATC AGC GTG CTG CTC ACA CGC CCG GGA GAT GGA GGC ACA GGC CGC CCT GGG CCA
 354 E   I   S   V   L   L   T   R   P   G   D   G   G   T   G   R   P   G   P

1495 CCA CTG ATC AGC CGG ACC AAG TGC GCA GAG CCC ACG AGG GCC CCC AAA GGT CTG GCT
 373 P   L   I   S   R   T   K   C   A   E   P   T   R   A   P   K   G   L   A

1552 TTT GCT GAG ATC CAG GCT CGC CAG CTG ACC CTG CAG TGG GAG CCC CTG GGC TAT AAT
 392 F   A   E   I   Q   A   R   Q   L   T   L   Q   W   E   P   L   G   Y   N

1609 GTC ACA CGT TGT CAT ACC TAC GCT GTG TCC CTT TGC TAT CGC TAC ACC CTG GGC GGC
 411 V   T   R   C   H   T   Y   A   V   S   L   C   Y   R   Y   T   L   G   G

1666 AGC CAC AAC CAG ACC ATC CGG GAG TGT GTG AAG ATG GAG CGG GGT GCC AGC CGC TAC
 430 S   H   N   Q   T   I   R   E   C   V   K   M   E   R   G   A   S   R   Y

1723 ACC ATC AAG AAT CTG CTG CCA TTC AGA AAC ATC CAC GTG CGT CTG ATT CTC ACA AAC
 449 T   I   K   N   L   L   P   F   R   N   I   H   V   R   L   I   L   T   N

1780 CCT GAG GGG CGC AAG GAG GGC AAG GAG GTC ACC TTC CAG ACA GAT GAA GAT GTG CCT
 468 P   E   G   R   K   E   G   K   E   V   T   F   Q   T   D   E   D   V   P

1837 GGT GGG ATT GCA GCT GAG TCC CTA ACC TTC ACT CCA CTG GAG GAC ATG ATC TTT CTC
 487 G   G   I   A   A   E   S   L   T   F   T   P   L   E   D   M   I   F   L
```

FIG._1C

```
1894 AAG TGG GAG GAG CCC CAG GAG CCC AAT GGC CTC ATC ACT CAG TAT GAG ATC AGC TAC
 506 K   W   E   E   P   Q   E   P   N   G   L   I   T   Q   Y   E   I   S   Y

1951 CAA AGC ATT GAG TCC TCA GAC CCA GCA GTG AAC GTG CCC GGC CCG AGA CGC ACC ATC
 525 Q   S   I   E   S   S   D   P   A   V   N   V   P   G   P   R   R   T   I

2008 TCC AAA CTC CGG AAT GAG ACT TAC CAC GTC TTC TCC AAC CTG CAT CCC GGC ACC ACG
 544 S   K   L   R   N   E   T   Y   H   V   F   S   N   L   H   P   G   T   T

2065 TAT CTG TTC TCC GTG CGT GCT CGG ACG AGC AAG GGC TTC GGC CAG GCG GCT CTC ACT
 563 Y   L   F   S   V   R   A   R   T   S   K   G   F   G   Q   A   A   L   T

2122 GAG ATA ACC ACC AAC ATC TCA GCT CCC AGC TTT GAT TAT GCC GAC ATG CCG TCA CCC
 582 E   I   T   T   N   I   S   A   P   S   F   D   Y   A   D   M   P   S   P

2179 CTG GGC GAG TCC GAG AAC ACC ATC ACT GTG CTG TTG AGG CCG GCC CAG GGC CGA GGA
 601 L   G   E   S   E   N   T   I   T   V   L   L   R   P   A   Q   G   R   G

2236 GCC CCC ATC AGC GTC TAC CAG GTG GTT GTG GAG GAA GAG CGG CCA CGG CGC TTG CGG
 620 A   P   I   S   V   Y   Q   V   V   V   E   E   E   R   P   R   R   L   R

2293 CGG GAG CCC GGA GCT CAG GAC TGC TTC TCG GTA CCT CTG ACC TTT GAG ACG GCC CTG
 639 R   E   P   G   A   Q   D   C   F   S   V   P   L   T   F   E   T   A   L

2350 GCT CGC GGC CTG GTG CAC TAC TTT GGG GCT GAA CTG GCT GCC AGC AGC CTG CTT GAG
 658 A   R   G   L   V   H   Y   F   G   A   E   L   A   A   S   S   L   L   E

2407 GCC ATG CCC TTC ACC GTG GGT GAC AAC CAG ACC TAT CGT GGC TTC TGG AAC CCA CCG
 677 A   M   P   F   T   V   G   D   N   Q   T   Y   R   G   F   W   N   P   P
```

FIG._1D

```
2464 CTT GAG CCC AGA AAG GCC TAT CTC ATC TAT TTC CAG GCA GCA AGC CAC CTG AAA GGG
 696 L   E   P   R   K   A   Y   L   I   Y   F   Q   A   A   S   H   L   K   G

2521 GAA ACC CGA CTG AAC TGC ATC CGA ATT GCC AGG AAA GCT GCG TGC AAG GAG AGC AAG
 715 E   T   R   L   N   C   I   R   I   A   R   K   A   A   C   K   E   S   K

2578 CGA CCC CTC GAA GTG TCC CAG AGA TCG GAG GAG ATG GGG CTC ATC CTG GGC ATC TGT
 734 R   P   L   E   V   S   Q   R   S   E   E   M   G   L   I   L   G   I   C

2635 GCA GGT GGT CTT GCC GTC CTC ATT CTC CTC CTG GGG GCC ATC ATT GTC ATC ATC CGC
 753 A   G   G   L   A   V   L   I   L   L   L   G   A   I   I   V   I   I   R

2692 AAA GGG AAG CCA GTG AAC ATG ACG AAA GCC ACG GTC AAC TAC CGC CAG GAG AAG ACT
 772 K   G   K   P   V   N   M   T   K   A   T   V   N   Y   R   Q   E   K   T

2749 CAC ATG ATG AGT GCC GTG GAC CGC AGC TTC ACA GAT CAG AGT ACT CTG CAG GAG GAT
 791 H   M   M   S   A   V   D   R   S   F   T   D   Q   S   T   L   Q   E   D

2806 GAG CGG TTG GGT CTG TCC TTT ATG GAT GCT CCT GGC TAT AGT CCT CGT GGA GAC CAG
 810 E   R   L   G   L   S   F   M   D   A   P   G   Y   S   P   R   G   D   Q

2863 CGA AGC GGT GGT GTC ACC GAG GCC AGC AGC CTC CTG GGG GGT TCT CCA AGG CGC CCA
 829 R   S   G   G   V   T   E   A   S   S   L   L   G   G   S   P   R   R   P

2920 TGC GGC CGG AAG GGT TCT CCG TAT CAT ACC GGG CAG CTC CAC CCT GCA GTC CGA GTG
 848 C   G   R   K   G   S   P   Y   H   T   G   Q   L   H   P   A   V   R   V

2977 GCT GAC CTT CTA CAG CAC ATC AAC CAG ATG AAG ACA GCC GAG GGC TAC GGC TTC AAG
 867 A   D   L   L   Q   H   I   N   Q   M   K   T   A   E   G   Y   G   F   K
```

FIG._1E

```
3034 CAG GAG TAC GAG AGT TTC TTT GAG GGC TGG GAC GCC ACC AAG AAG AAA GAC AAG CTC
 886 Q   E   Y   E   S   F   F   E   G   W   D   A   T   K   K   K   D   K   L

3091 AAG GGC GGC CGA CAG GAG CCA GTG TCT GCC TAT GAT CGA CAC CAT GTG AAA CTA CAC
 905 K   G   G   R   Q   E   P   V   S   A   Y   D   R   H   H   V   K   L   H

3148 CCG ATG CTG GCA GAC CCT GAT GCC GAC TAC ATC TCT GCC AAC TAC ATA GAC GGC TAC
 924 P   M   L   A   D   P   D   A   D   Y   I   S   A   N   Y   I   D   G   Y

3205 CAC AGG TCA AAC CAC TTC ATA GCC ACT CAA GGG CCA AAG CCT GAG ATG ATC TAC GAT
 943 H   R   S   N   H   F   I   A   T   Q   G   P   K   P   E   M   I   Y   D

3262 TTC TGG CGC ATG GTG TGG CAG GAA CAG TGT GCG AGC ATC GTC ATG ATC ACC AAG CTG
 962 F   W   R   M   V   W   Q   E   Q   C   A   S   I   V   M   I   T   K   L

3319 GTA GAG GTG GGC AGG GTG AAG TGT TCT CGC TAC TGG CCT GAG GAC TCA GAC ATG TAT
 981 V   E   V   G   R   V   K   C   S   R   Y   W   P   E   D   S   D   M   Y

3376 GGG GAC ATC AAG ATC ACG CTG GTA AAG ACA GAG ACA CTG GCT GAG TAT GTG GTG CGC
1000 G   D   I   K   I   T   L   V   K   T   E   T   L   A   E   Y   V   V   R

3433 ACC TTT GCC CTG GAG CGG AGA GGT TAC TCA GCC CGG CAT GAG GTC CGC CAG TTC CAT
1019 T   F   A   L   E   R   R   G   Y   S   A   R   H   E   V   R   Q   F   H

3490 TTC ACA GCG TGG CCA GAG CAT GGT GTC CCC TAC CAC GCC ACG GGG CTG CTG GCC TTC
1038 F   T   A   W   P   E   H   G   V   P   Y   H   A   T   G   L   L   A   F

3547 ATC CGG CGT GTG AAG GCT TCC ACT CCA CCT GAT GCC GGG CCC ATT GTC ATT CAC TGC
1057 I   R   R   V   K   A   S   T   P   P   D   A   G   P   I   V   I   H   C
```

FIG._1F

```
3604 AGT GCA GGA ACT GGC CGC ACA GGC TGC TAC ATC GTC CTG GAT GTG ATG CTG GAC ATG
1076 S   A   G   T   G   R   T   G   C   Y   I   V   L   D   V   M   L   D   M

3661 GCT GAA TGT GAG GGG GTC GTG GAC ATT TAC AAC TGT GTG AAG ACC CTC TGT TCC CGA
1095 A   E   C   E   G   V   V   D   I   Y   N   C   V   K   T   L   C   S   R

3718 CGG GTC AAC ATG ATC CAG ACG GAG GAA CAA TAT ATC TTC ATC CAC GAT GCA ATC TTG
1114 R   V   N   M   I   Q   T   E   E   Q   Y   I   F   I   H   D   A   I   L

3775 GAG GCC TGC CTG TGT GGG GAG ACC ACC ATC CCT GTC AAC GAG TTC AGG GCC ACC TAC
1133 E   A   C   L   C   G   E   T   T   I   P   V   N   E   F   R   A   T   Y

3832 AGG GAG ATG ATC CGC ATT GAC CCT CAG AGC AAT TCC TCC CAG CTT CGG GAA GAG TTC
1152 R   E   M   I   R   I   D   P   Q   S   N   S   S   Q   L   R   E   E   F

3889 CAG ACG CTG AAC TCG GTC ACG CCG CCG CTG GAT GTG GAG GAG TGT AGC ATT GCC CTG
1171 Q   T   L   N   S   V   T   P   P   L   D   V   E   E   C   S   I   A   L

3946 CTG CCC CGG AAT CGA GAC AAG AAC CGT AGC ATG GAT GTG CTG CCA CCA GAC CGC YGC
1190 L   P   R   N   R   D   K   N   R   S   M   D   V   L   P   P   D   R   X

4003 CTG CCC TTC CTC ATC TCC AGT GAT GGG GAC CCC AAT AAC TAC ATC AAT GCA GCA CTG
1209 L   P   F   L   I   S   S   D   G   D   P   N   N   Y   I   N   A   A   L

4060 ACT GAC AGC TAC ACA CGG AGC GCC GCC TTC ATC GTG ACC CTG CAC CCG CTG CAG AGT
1228 T   D   S   Y   T   R   S   A   A   F   I   V   T   L   H   P   L   Q   S

4117 ACC ACG CCC GAC TTC TGG CGG CTG GTC TAC GAC TAC GGG TGC ACC TCC ATC GTC ATG
1247 T   T   P   D   F   W   R   L   V   Y   D   Y   G   C   T   S   I   V   M
```

FIG._1G

```
4174 CTG AAC CAA CTT AAC CAG TCC AAC TCC GCC TGG CCC TGC TTG CAG TAC TGG CCG GAG
1266 L   N   Q   L   N   Q   S   N   S   A   W   P   C   L   Q   Y   W   P   E

4231 CCA GGC CGA CAG CAG TAT GGG CTC ATG GAG GTG GAG TTT GTG TCT GGC ACA GCA AAC
1285 P   G   R   Q   Q   Y   G   L   M   E   V   E   F   V   S   G   T   A   N

4288 GAG GAT TTG GTG TCC CGA GTG TTC CGG GTG CAG AAC TCT TCT CGG CTG CAG GAG GGT
1304 E   D   L   V   S   R   V   F   R   V   Q   N   S   S   R   L   Q   E   G

4345 CAC CTG CTG GTA CGG CAC TTC CAG TTT CTG CGT TGG TCT GCT TAT CGG GAC ACG CCT
1323 H   L   L   V   R   H   F   Q   F   L   R   W   S   A   Y   R   D   T   P

4402 GAC TCC AGG AAG GCC TTT CTG CAC CTG TTG GCT GAG GTG GAC AAG TGG CAG GCA GAG
1342 D   S   R   K   A   F   L   H   L   L   A   E   V   D   K   W   Q   A   E

4459 AGT GGG GAT GGG CGC ACC GTG GTG CAT TGT CTC AAC GGG GGT GGC CGC AGT GGC ACC
1361 S   G   D   G   R   T   V   V   H   C   L   N   G   G   G   R   S   G   T

4516 TTC TGC GCC TGT GCC ACG GTC TTG GAG ATG ATC CGC TGT CAC AGC CTG GTG GAT GTT
1380 F   C   A   C   A   T   V   L   E   M   I   R   C   H   S   L   V   D   V

4573 TTC TTT GCT GCC AAA ACA CTT CGG AAC TAC AAG CCC AAT ATG GTG GAG ACC ATG GAT
1399 F   F   A   A   K   T   L   R   N   Y   K   P   N   M   V   E   T   M   D

4630 CAG TAT CAT TTC TGC TAC GAC GTG GCC CTG GAG TAC CTG GAG GCT CTG GAG TTG AGA
1418 Q   Y   H   F   C   Y   D   V   A   L   E   Y   L   E   A   L   E   L   R

4687 TAG  C AGGCGCCTGA CCTGGGGCAC CCAGTGAACA CCCAGGGCAT GGCCCATCAT CCCAGATGAR
1437 O
```

FIG._1H

```
4751 GAGGGCCTGT GGCCCCAACT TTGCTCAGCC ATAATTCCAC AGGGACAACA CTGGAACGGA CGGACACTGC
4821 ACCATCTTGG TGACCCCCAC GGGAAGGCTG CAGGCCAAGG AGAAGCTTTG CAAGACTGTA TCAGCCCCAC
4891 CTCTAGAGGG CCCTGCAGAC CTGTGCAGAG AAGCTCGCCT GGACCAAAAT AGCTAGTGCT GGAGAGCACA
4961 GGCCAGGCCC CTCTGCTCCA TCACAGTCCT TGGCCAGAAA TGAATGAGTG TCTGCAGAGA GCACCCATGG
5031 TTTGCACCCA GTATGGTCCT TTCTGCACGT GGTGGAGGCT CACTGGGACT TGGCAGGGGC TGAGTCCCCG
5101 AGAGTCCTGA AGCTGGGACT CTTCCCCGTC TCGCCGGTGG GACCCGCTGA GCATCCTGCA GCTCCATTCT
5171 CCATCCCCAC TGCCCCTACA GACCTGGGGT GCTTTGCTCG CTTTCCTCCT GCTTCTGAGC TTTTCCTGCA
5241 ACAGGACCCG TGCCTCCTTC CTGGGCTCCA TCCCTGCCTG GCCCAGTATA TGCAGAATGA TATACTTCAG
5311 CTCCTTCTTC CCCTGGCCTT TGGGTCTCCA TGGTTCAGTC CTGCTCAGCT TGGGCCTGTG ACAATCCACA
5381 AGGCTGAATC ACAGCCCCTG GGGTTGAGGT CCCTGTGGCT CTTGGTGAGG CTGCCACTGG ATCGGGGCAG
5451 GCTAGAACAG GGCTGGTGTC AGCTCCTAGA GTACAGAGGA AGAAGGGATA CTTTGGAATG GAGGACCAGT
5521 GCTTTTTTTG TTGTTGTTAT TTTGTTATTT TTTTGATGGG AGGGTGGGAA GTTCTCTTTA TAATGGGGTA
5591 GGCCACACCC CCATTTCGTG CCTCAATTTC CCCATCTGTA AACTGTAGAT ATGACTACTG ACCTACCTCA
5661 CAGGGGGCTG TGGGGAGGTG TAAGGTAATG TTTGTAAAGC GCTTTGTAAA TAAATGTGCT CTCTGAATGC
5731 CAAAAAAAAA AAAAAAAAAA AAAAAAAAAA AAAAAAAAA
```

FIG._1I

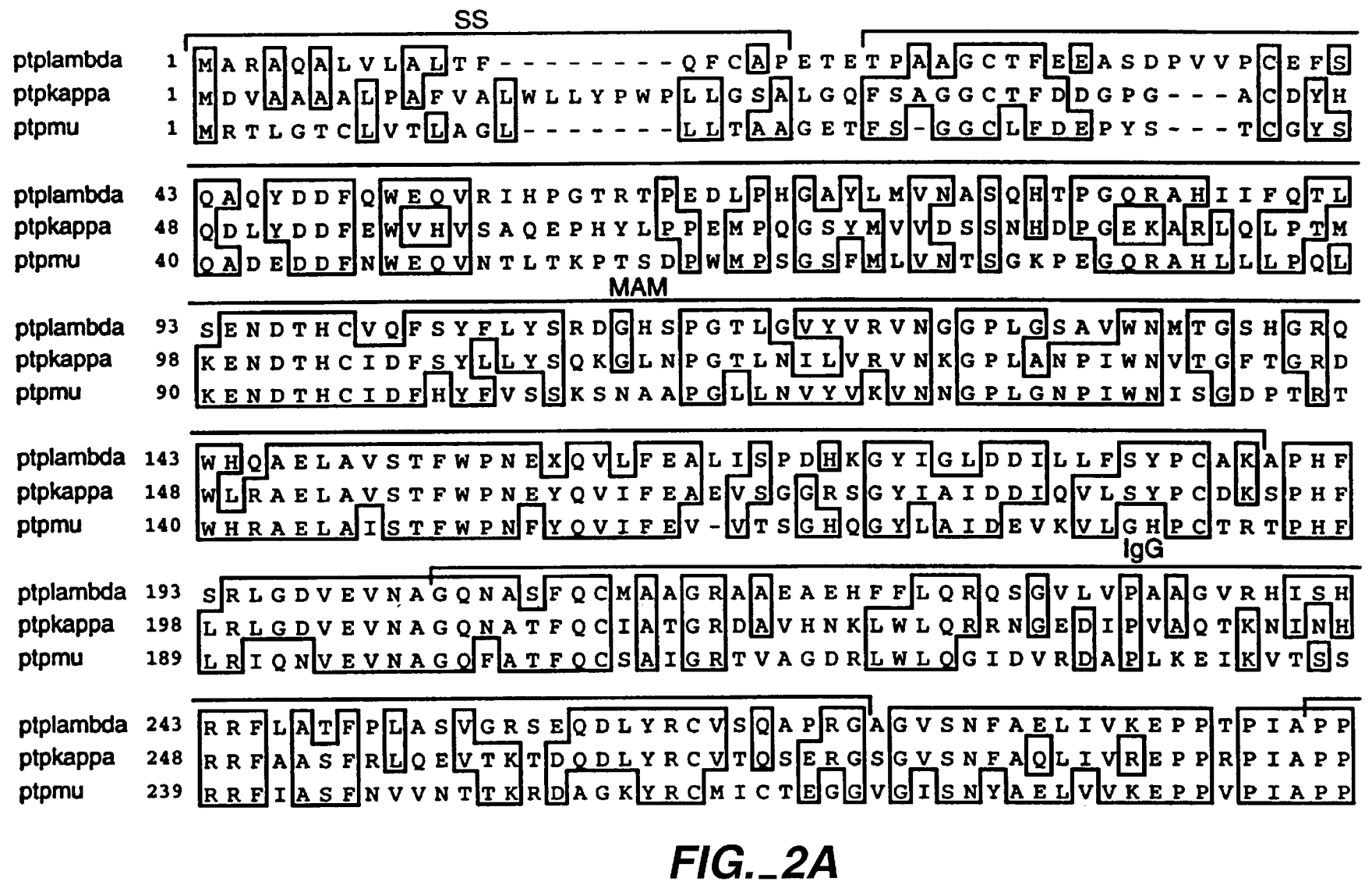

```
SS, MAM, IgG (domain labels)

ptplambda    1  M A R A Q A L V L A L T F - - - - - - - - - Q F C A P E T E T P A A G C T F E E A S D P V V P C E F S
ptpkappa     1  M D V A A A A L P A F V A L W L L Y P W P L L G S A L G Q F S A G G C T F D D G P G - - - A C D Y H
ptpmu        1  M R T L G T C L V T L A G L - - - - - - - - L L T A A G E T F S - G G C L F D E P Y S - - - T C G Y S

ptplambda   43  Q A Q Y D D F Q W E Q V R I H P G T R T P E D L P H G A Y L M V N A S Q H T P G Q R A H I I F Q T L
ptpkappa    48  Q D L Y D D F E W V H V S A Q E P H Y L P P E M P Q G S Y M V V D S S N H D P G E K A R L Q L P T M
ptpmu       40  Q A D E D D F N W E Q V N T L T K P T S D P W M P S G S F M L V N T S G K P E G Q R A H L L L P Q L

ptplambda   93  S E N D T H C V Q F S Y F L Y S R D G H S P G T L G V Y V R V N G G P L G S A V W N M T G S H G R Q
ptpkappa    98  K E N D T H C I D F S Y L L Y S Q K G L N P G T L N I L V R V N K G P L A N P I W N V T G F T G R D
ptpmu       90  K E N D T H C I D F H Y F V S S K S N A A P G L L N V Y V K V N N G P L G N P I W N I S G D P T R T

ptplambda  143  W H Q A E L A V S T F W P N E X Q V L F E A L I S P D H K G Y I G L D D I L L F S Y P C A K A P H F
ptpkappa   148  W L R A E L A V S T F W P N E Y Q V I F E A E V S G G R S G Y I A I D D I Q V L S Y P C D K S P H F
ptpmu      140  W H R A E L A I S T F W P N F Y Q V I F E V - V T S G H Q G Y L A I D E V K V L G H P C T R T P H F

ptplambda  193  S R L G D V E V N A G Q N A S F Q C M A A G R A A E A E H F F L Q R Q S G V L V P A A G V R H I S H
ptpkappa   198  L R L G D V E V N A G Q N A T F Q C I A T G R D A V H N K L W L Q R R N G E D I P V A Q T K N I N H
ptpmu      189  L R I Q N V E V N A G Q F A T F Q C S A I G R T V A G D R L W L Q G I D V R D A P L K E I K V T S S

ptplambda  243  R R F L A T F P L A S V G R S E Q D L Y R C V S Q A P R G A G V S N F A E L I V K E P P T P I A P P
ptpkappa   248  R R F A A S F R L Q E V T K T D Q D L Y R C V T Q S E R G S G V S N F A Q L I V R E P P R P I A P P
ptpmu      239  R R F I A S F N V V N T T K R D A G K Y R C M I C T E G G V G I S N Y A E L V V K E P P V P I A P P
```

FIG._2A

Fn III

```
ptplambda  293  QLLRAGPTYLIIQLNTNSIIGDGPIVRKEIEYRMARGPWAEVHAVNLQTY
ptpkappa   298  QLLGVGPTYLLIQLNANSIIGDGPIILKEVEYRMTSGSWTETHAVNAPTY
ptpmu      289  QLASVGATYLWIQLNANSINGDGPIVAREVEYCTASGSWNDRQPVDSTSY

ptplambda  343  KLWHLDPDTEYEISVLLTRPGDGGTGRPGPPLISRTKCAEPTRAPKGLAF
ptpkappa   348  KLWHLDPDTEYEIRVLLTRPGEGGTGLPGPPLITRTKCAEPMRTPKTLKI
ptpmu      339  KIGHLDPDTEYEISVLLTRPGEGGTGSPGPALRTRTKCADPMRGPRKLEV

ptplambda  393  AEIQARQLTLQWEPLGYNVTRCHTYAVSLCYRYTLGGSHNQTIRECVKME
ptpkappa   398  AEIQARRIAVDWESLGYNITRCHTFNVTICYHY-FRGHNESRAD-CLDMD
ptpmu      389  VEVKSRQITIRWEPFGYNVTRCHSYNLTVHYGYQVGGQEQVREEVSWDTD

ptplambda  443  RGASRYTIKNLLPFRNIHVRLILTNPEGRKEGKEVTFQTDEDVPGGIAAE
ptpkappa   446  PKAPQHVVNHLPPYTNVSLKMILTNPEGRKESEETIIQTDEDVPGPVPVK
ptpmu      439  NSHPQHTITNLSPYTNVSVKLILMNPEGRKESQELTVQTDEDLPGAVPTE

ptplambda  493  SLTFTPLEDMIFLKWEEPQEPNGLITQYEISYQSIESSDPAVNVPGPRRT
ptpkappa   496  SLQGTSFENKIFLNWKEPLEPNGIITQYEVSYSSIRSFDPAVPVAGPPQT
ptpmu      489  SIQGSAFEEKIFLQWREPTQTYGVITLYEITYKAVSSFDPEIDLSNQSGR

ptplambda  543  ISKLRNETYHVFSNLHPGTTYLFSVRARTSKGFGQAALTEITTNISAPSF
ptpkappa   546  VSNLWNSTHHVFMHLHPGTTYQFFIRASTVKGFGPATAINVTTNISAPSL
ptpmu      539  VSKLGNETHFLFFGLYPGTTYSFTIRASTAKGFGPPATNQFTTKISAPSM
```

FIG._2B

```
                  Fn III
ptplambda 593 -DYADMPSPLGESENTITVLLRPAQGRGAPISVYQVVVEEERPRRLREP
ptpkappa  596 PDYEGVDASLNETATTITVLLRPAQAKGAPISAYQIVVEQLHPHRTKREA
ptpmu     589 PAYE-FETPLNQTDNTVTVMLKPAQSRGAPVSVYQIVVEEERPRRTKKTT

ptplambda 642 GAQDCFSVPLTFETALARGLVHYFGAELAASSLLEAMPFTVGDNQTYRGF
ptpkappa  646 GAMECYQVPVTYQNALSGGAPYYFAAELPPGNLPEPAPFTVGDNRTYKGF
ptpmu     638 EILKCYPVPIHFQNASILNSQYYFAAEFPADSLQAAQPFTIGDNKTYNGY

ptplambda 692 WNPPLEPRKAYLIYFQAASHLKGETRLNCIRIARKAACKESKRPLEVSQR
ptpkappa  696 WNPPLAPRKGYNIYFQAMSSVEKETKTQCVRIATKAAATEEPEVIPDPAK
ptpmu     688 WNTPLLPHKSYRIYYQAASRANGETKIDCVRVATKGAVT--PKPVPEPEK
                  TMD
ptplambda 742 SEEMGLILGICAGGLAVLILLLGAIIVIIRKGKPVNMTKATV-NYRQEKT
ptpkappa  746 QTDRVVKIAGISAGILVFILLLLVVIVIVKKSKLAKKRKDAMGNTRQEMT
ptpmu     736 QTDHTVKIAGVIAGILLFVIIFLGVVLVMKKRKLAKKRKETMSSTRQEMT

ptplambda 791 HMMSAVDRSFTDQSTLQEDERLGLSFMDAPGYSPRG--------------
ptpkappa  796 HMVNAMDRSYADQSTLHAEDPLSLTFMDQHNFSPR---------LPNDPL
ptpmu     786 VMVNSMDKSYAEQGT-NCDEAFS--FMGTHNLNGRSVSSPSSFTMKTNTL
                  Cadherin
ptplambda 827 ----------DQRSGGVTEASSLLGGSPRRPCGRKGSPYHTGQLHPAVRV
ptpkappa  837 ---VPTAVL-DENHSATAESSRLLDVPRY-LCEGTESPYQTGQLHPAIRV
ptpmu     833 STSVPNSYYPDETHTMASDTSSLAQPHTYKKREAADVPYQTGQLHPAIRV
```

FIG._2C

```
ptplambda  867  ADLLQHINQMKTAEGYGFKQEYESFFEG----WDATKKKDKLKGGRQEPV
ptpkappa   882  ADLLQHINLMKTSDSYGFKEEYESFFEGQSASWDVAKKDQNRAKNRYGNI
ptpmu      883  ADLLQHITQMKCAEGYGFKEEYESFFEGQSAPWDSAKKDENRMKNRYGNI

ptplambda  913  SAYDRHHVKLHPMLADPDADYISANYI------DGYHRSNHFIATQGPKP
ptpkappa   932  IAYDHSRVILQPVEDDPSSDYINANYIDIWLYRDGYQRPSHYIATQGPVH
ptpmu      933  IAYDHSRVRLQMLEGDNNSDYINGNYI------DGYHRPNHYIATQGPMQ

ptplambda  957  EMIYDFWRMVWQEQCASIVMITKLVEVGRVKCSRYWPEDSDMYGDIKITL
ptpkappa   982  ETVYDFWRMVWQEQSACIVMVTNLVEVGRVKCYKYWPDDTEVYGDFKVTC
ptpmu      977  ETIYDFWRMVWHENTASIIMVTNLVEVGRVKCCKYWPDDTEIYKDIKVTL
                                 PTPase I

ptplambda 1007  VKTETLAEYVVRTFALERRGYSARHEVRQFHFTAWPEHGVPYHATGLLAF
ptpkappa  1032  VEMEPLAEYVVRTFTLERRGYNEIREVKQFHFTGWPDHGVPYHATGLLSF
ptpmu     1027  IDTELLAEYVIRTFAVEKRGIHEIREIRQFHFTGWPDHGVPYHATGLLGF

ptplambda 1057  IRRVKASTPPDAGPIVIHCSAGTGRTGCYIVLDVMLDMAECEGVVDIYNC
ptpkappa  1082  IRRVKLSNPPSAGPIVVHCSAGAGRTGCYIVIDIMLDMAEREGVVDIYNC
ptpmu     1077  VRQVKSKSPPNAGPLVVHCSAGAGRTGCFIVIDIMLDMAEREGVVDIYNC

ptplambda 1107  VKTLCSRRVNMIQTEEQYIFIHDAILEACLCGETTIPVNEFRATYREMIR
ptpkappa  1132  VKALRSRRINMVQTEEQYIFIHDAILEACLCGETAIPVCEFKAAYFDMIR
ptpmu     1127  VRELRSRRVNMVQTEEQYVFIHDAILEACLCGDTSIPASQVRSLYYDMNK
```

FIG._2D

```
ptplambda 1157 I D P Q S N S S Q L R E E F Q T L N S V T P P L D V E E C S I A L L P R N R D K N R S M D V L P P D
ptpkappa  1182 I D S Q T N S S H L K D E F Q T L N S V T P R L Q A E D C S I A C L P R N H D K N R F M D M L P P D
ptpmu     1177 L D P Q T N S S Q I K E E F R T L N M V T P T L R V E D C S I A L L P R N H E K N R C M D I L P P D

ptplambda 1207 R X L P F L I S S D G D P N N Y I N A A L T D S Y T R S A A F I V T L H P L Q S T T P D F W R L V Y
ptpkappa  1232 R C L P F L I T I D G E S S N Y I N A A L M D S Y R Q P A A F I V T Q Y P L P N T V K D F W R L V Y
ptpmu     1227 R C L P F L I T I D G E S S N Y I N A A L M D S Y K Q P S A F I V T Q H P L P N T V K D F W R L V L

ptplambda 1257 D Y G C T S I V M L N Q L N Q S N S A W P C L Q Y W P E P G R Q Q Y G L M E V E F V S G T A N E D L
ptpkappa  1282 D Y G C T S I V M L N E V D L S Q G - - - C P Q Y W P E E G M L R Y G P I Q V E C M S C S M D C D V
ptpmu     1277 D Y H C T S V V M L N D V D P A Q L - - - C P Q Y W P E N G V H R H G P I Q V E F V S A D L E E D I

ptplambda 1307 V S R V F R V Q N S S R L Q E G H L L V R H F Q F L R W S A Y R D T P D S R K A F L H L L A E V D K
ptpkappa  1329 I N R I F R I C N L T R P Q E G Y L M V Q Q F Q Y L G W A S H R E V P G S K R S F L K L I L Q V E K
ptpmu     1324 I S R I F R I Y N A S R P Q D G H R M V Q Q F Q F L G W P M Y R D T P V S K R S F L K L I R Q V D K
                                                                PTPase II

ptplambda 1357 W Q A E - - S G D G R T V V H C L N G G G R S G T F C A C A T V L E M I R C H S L V D V F F A A K T
ptpkappa  1379 W Q E E C E E G E G R T I I H C L N G G G R S G M F C A I G I V V E M V K R Q N V V D V F H A V K T
ptpmu     1374 W Q E E Y N G G E G P T V V H C L N G G G R S G T F C A I S I V C E M L R H Q R T V D V F H A V K T

ptplambda 1405 L R N Y K P N M V E T M D Q Y H F C Y D V A L E Y L E A L E L R
ptpkappa  1429 L R N S K P N M V E A P E Q Y R F C Y D V A L E Y L E S S - - -
ptpmu     1424 L R N N K P N M V D L L D Q Y K F C Y E V A L E Y L N S G - - -
```

FIG._2E

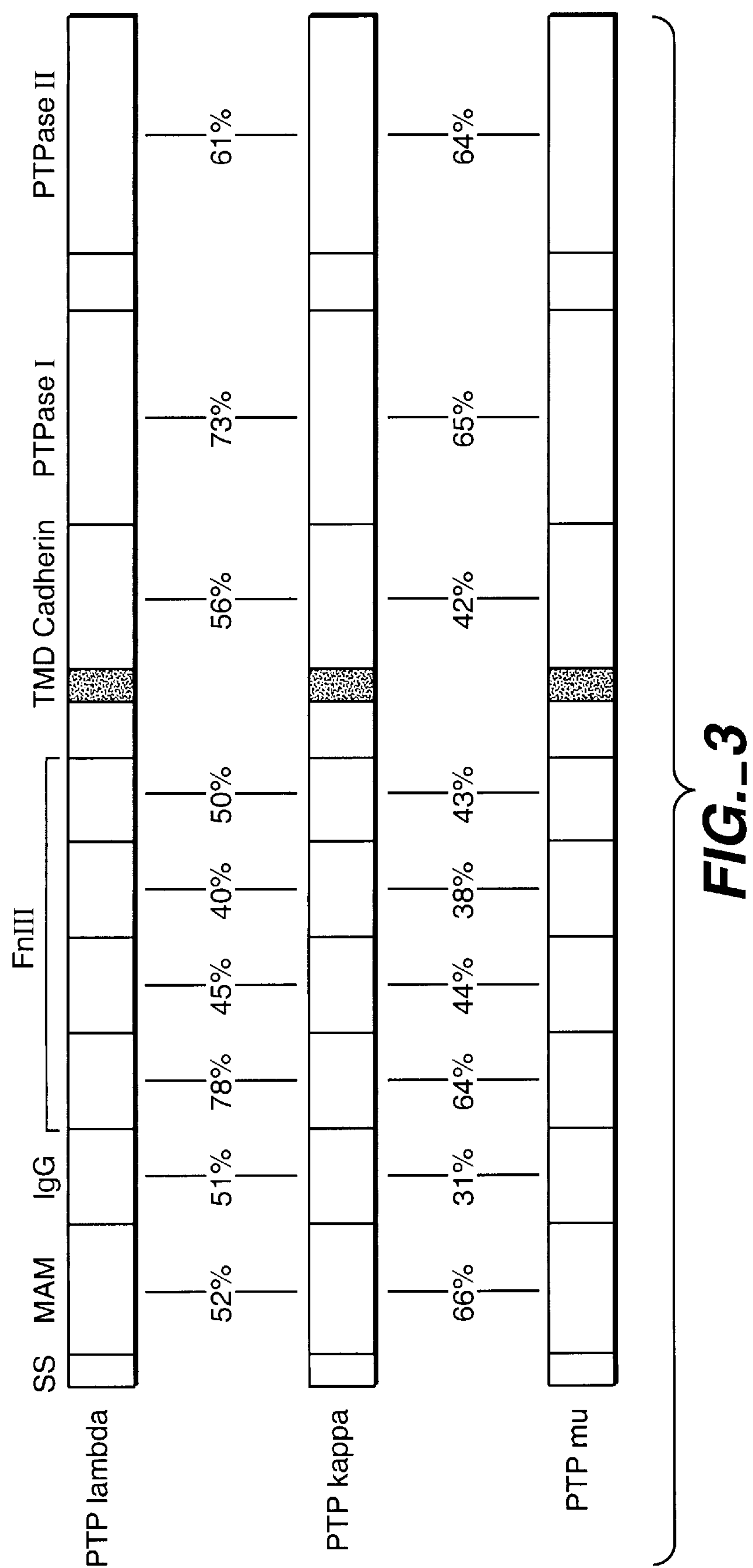
FIG._3

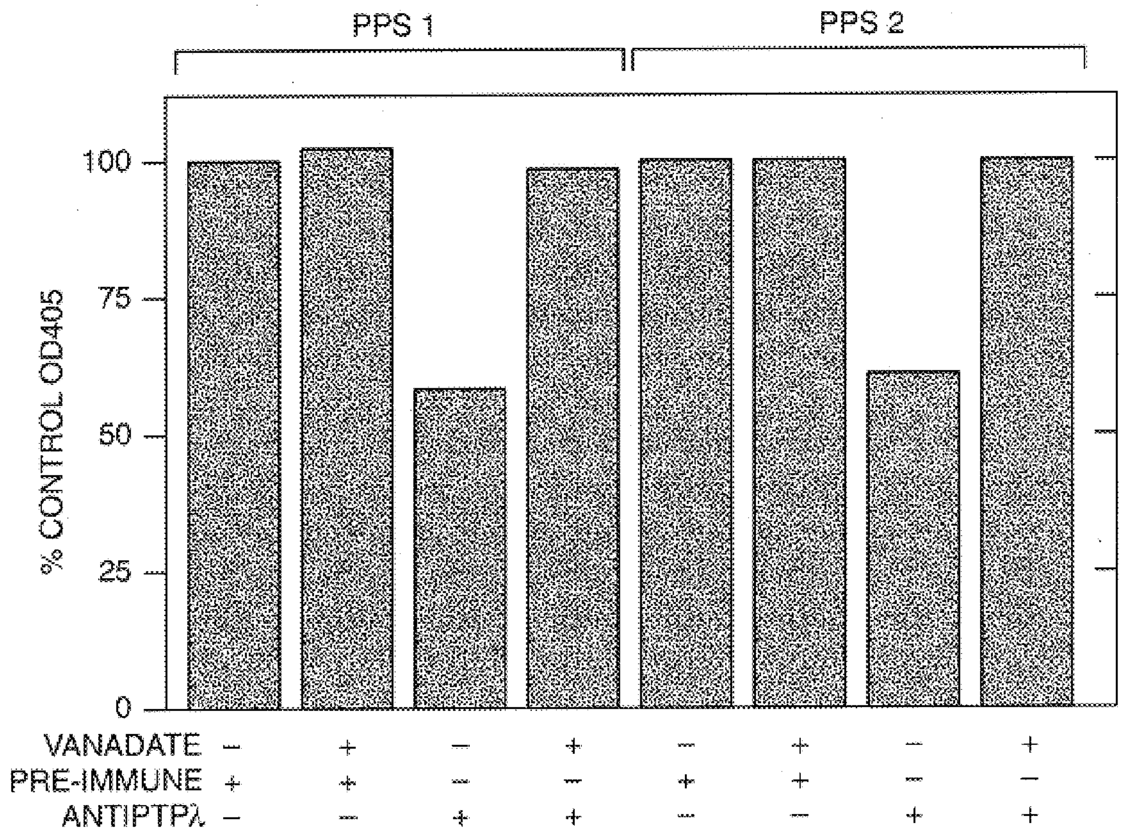
FIG._4
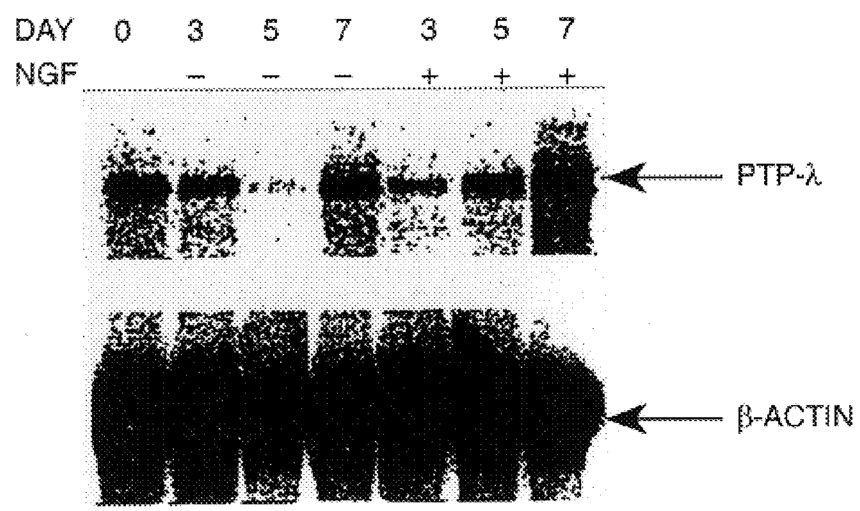
FIG._8

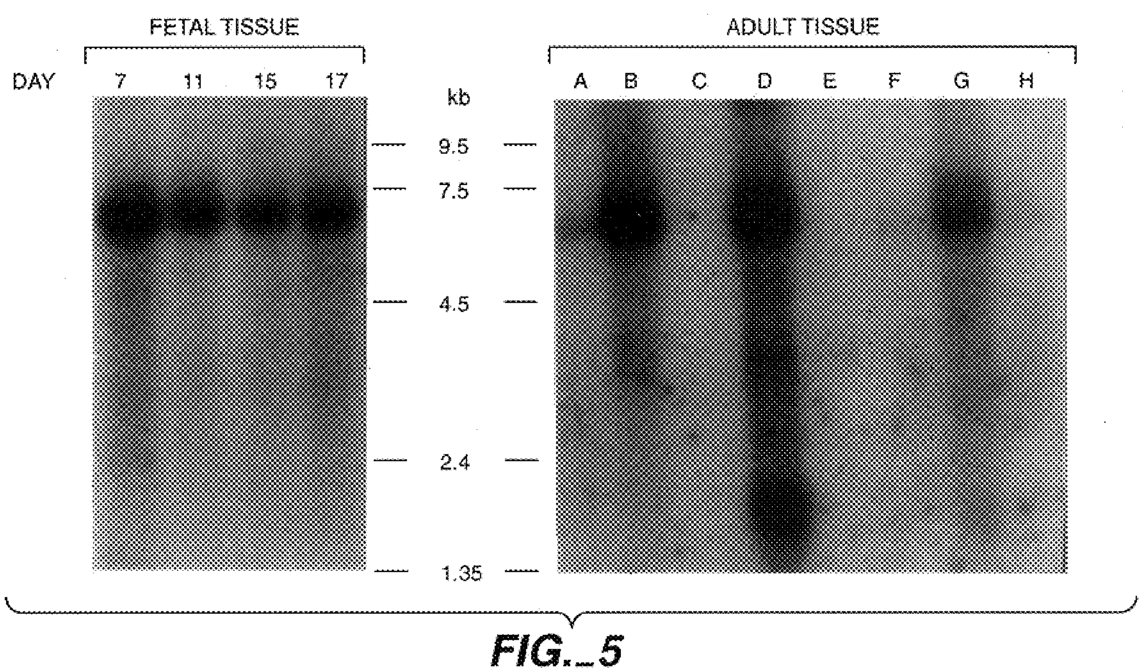
FIG._5

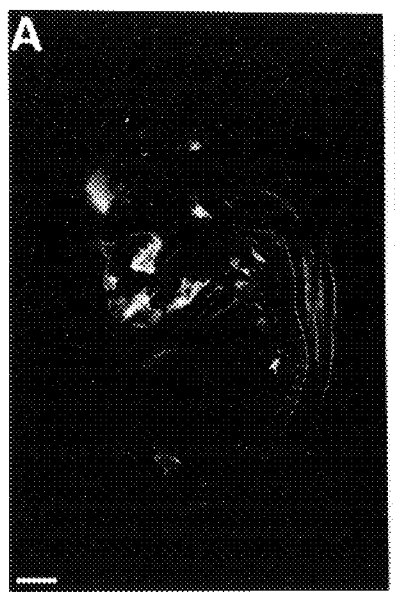
FIG._6A
B
vm
cx
FIG._6B
C
vm
c
p
FIG._6C

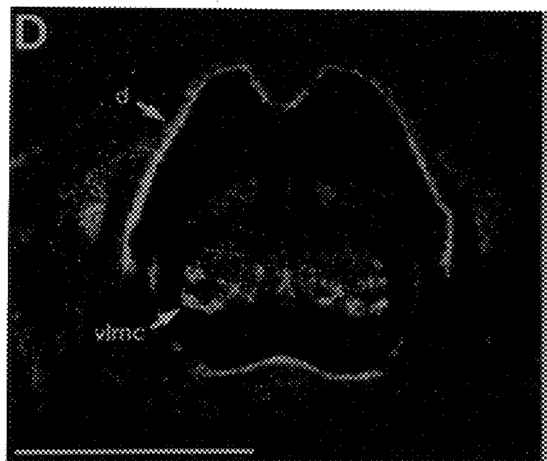
FIG._6D
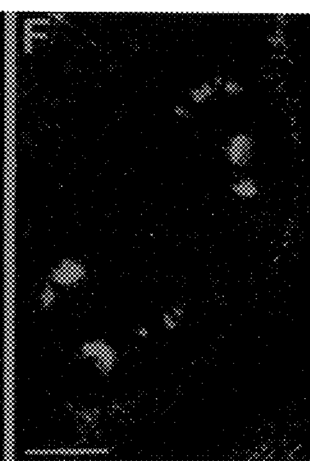
FIG._6F
G
g
FIG._6G

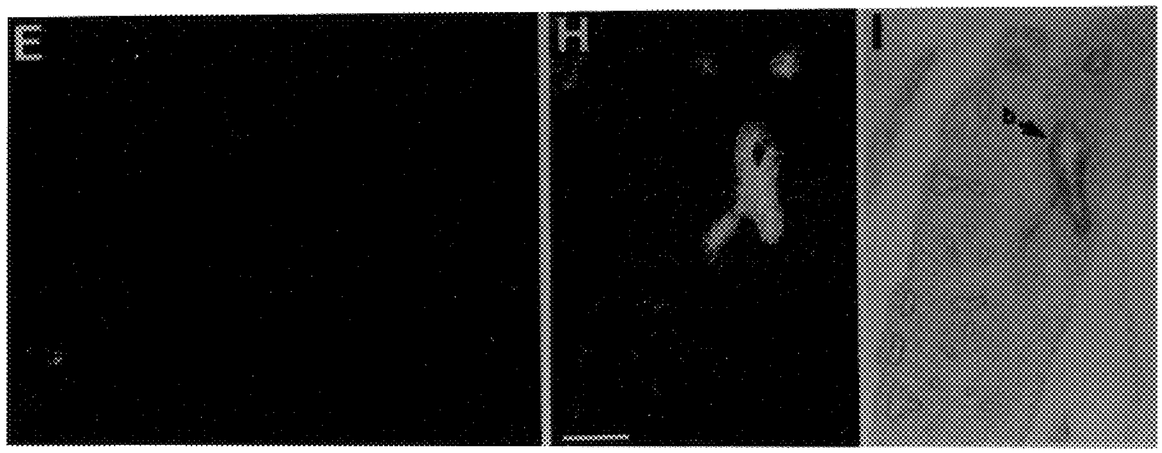
FIG._6E FIG._6H FIG._6I

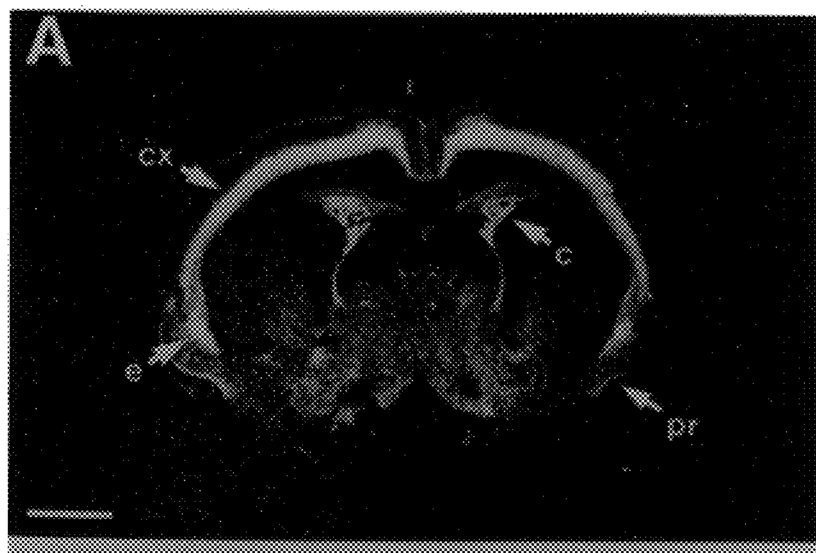
FIG._7A
FIG._7B
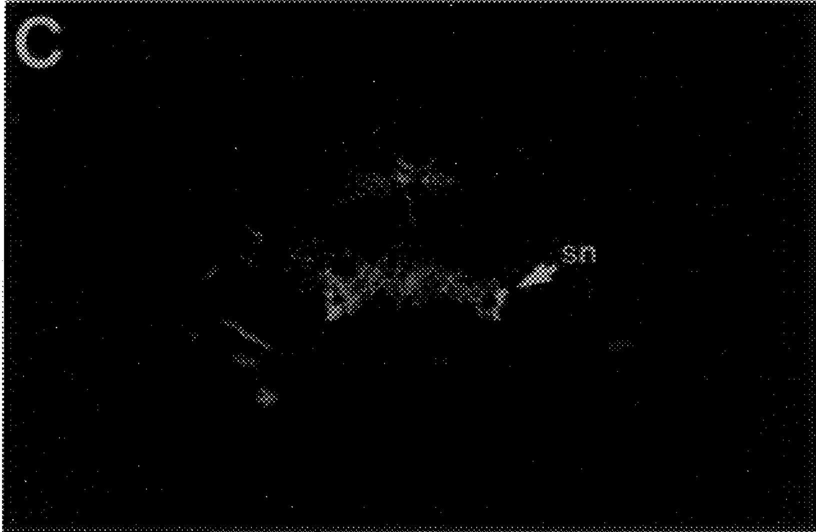
FIG._7C

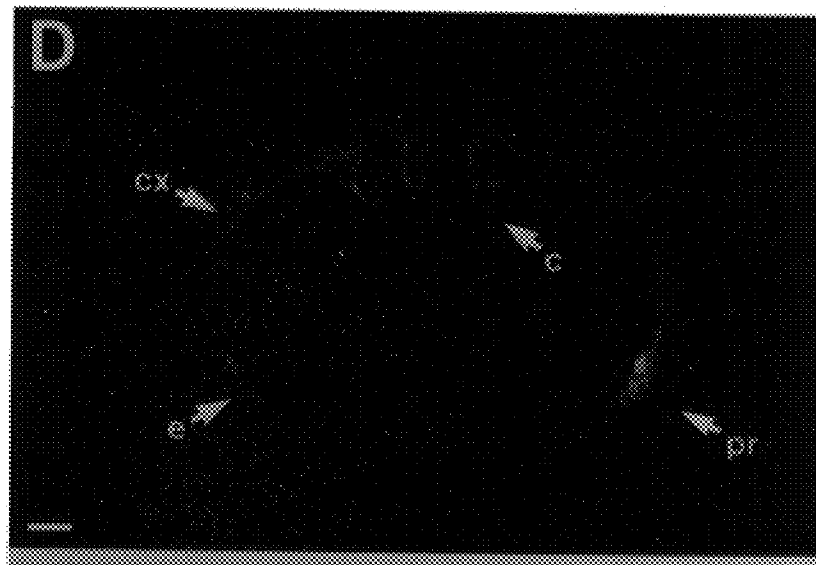
FIG._7D
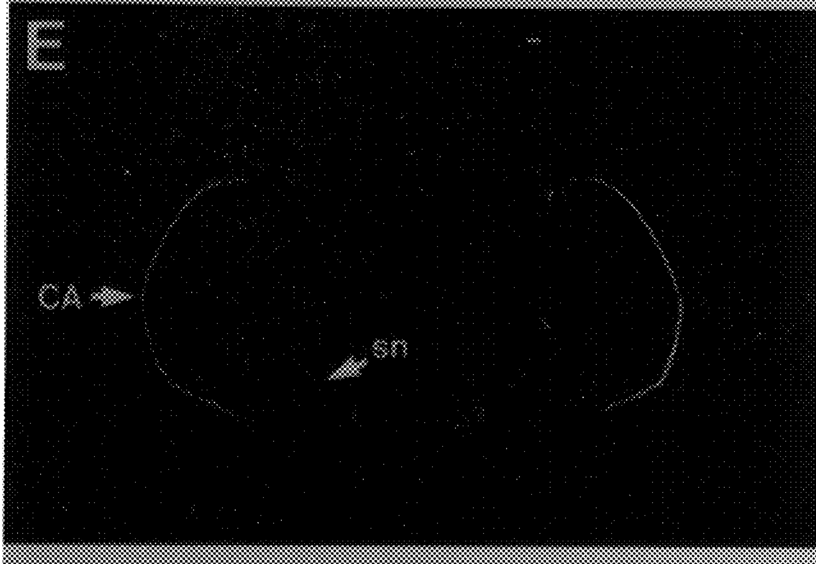
FIG._7E
FIG._7F

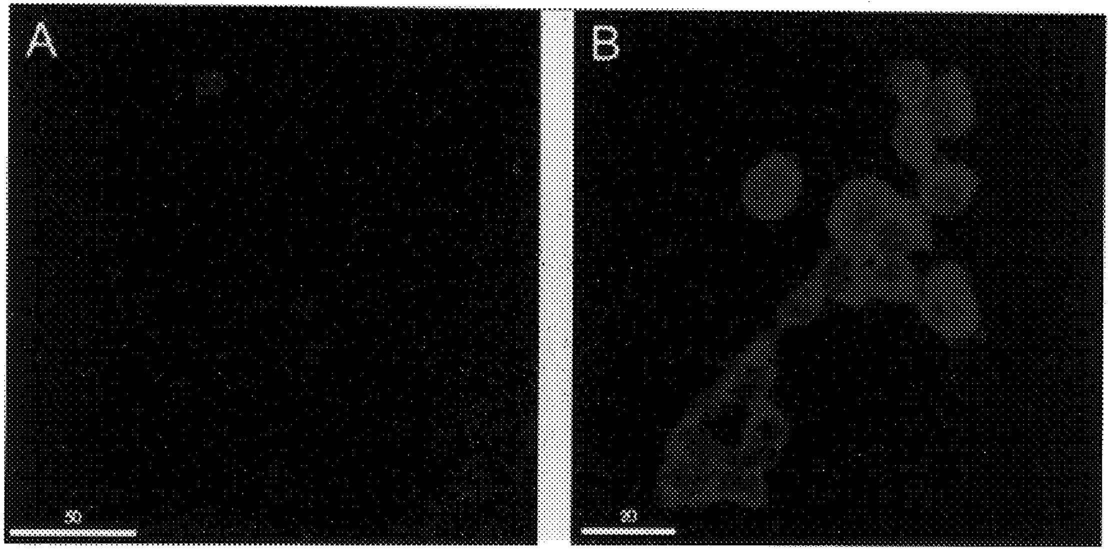
FIG._9A
FIG._9B
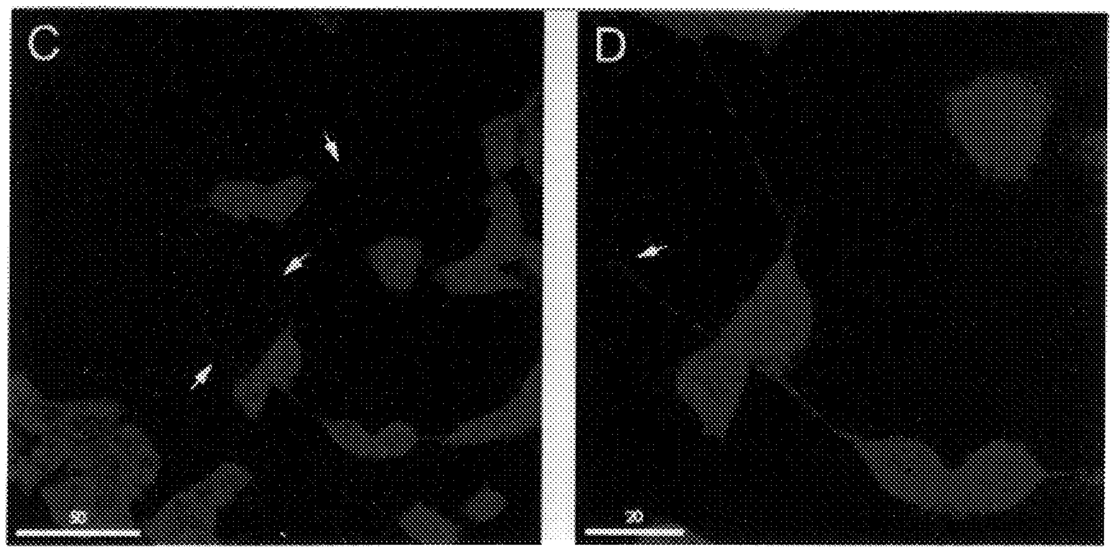
FIG._9C
FIG._9D

SEQUENCE LISTING (1) GENERAL INFORMATION:

(iii) NUMBER OF SEQUENCES: 10

(2) INFORMATION FOR SEQ ID NO:1:

```
    (i) SEQUENCE CHARACTERISTICS:
         (A) LENGTH: 5769 base pairs
         (B) TYPE: nucleic acid
         (C) STRANDEDNESS: single
         (D) TOPOLOGY: linear

   (ii) MOLECULE TYPE: DNA (genomic)

   (ix) FEATURE:
         (A) NAME/KEY: CDS
         (B) LOCATION: 379..4686

   (xi) SEQUENCE DESCRIPTION: SEQ ID NO:1:

GTTGACTACT CAGCTGCCAG AACATCCAAT CTGGCTCCTG CAACTTTAGA CCAACATATT     60

GTGTTTGATC TTCTCCTGAA CAACTTGGGA GATACGTCTG ATCTTCAGCT TGGTACATAC    120

AGTTGCGCAG TGAATGGCAC TTACGTGTTC ATTGTGCACA TGCTAAAGCT GGCATGATTA    180

ATGTTCGACT GCTATGTCAA CCTGATTAAC AATGAGGATG TCTTGGTGTC AGCTATGCCA    240

ACGATGGTGC TCCAGACCGG CGCCAGTCCC GCTCCGCGCG GCACTGTCCA CTACGGCTCC    300

CGCTCGCCTT GGGCTCCCGG TCGGGCTCCG GAGGCGTCGC CTCCCCAGCT GCGGGTCTCC    360

AGGACCTAGG CGGCGGCC ATG GCC CGG GCT CAG GCT CTG GTC CTG GCG CTC      411
                    Met Ala Arg Ala Gln Ala Leu Val Leu Ala Leu
                      1               5                  10

ACC TTC CAG TTC TGC GCG CCT GAG ACC GAG ACT CCC GCA GCT GGC TGC      459
Thr Phe Gln Phe Cys Ala Pro Glu Thr Glu Thr Pro Ala Ala Gly Cys
             15                  20                  25

ACC TTC GAG GAG GCG AGT GAC CCG GTC GTG CCC TGC GAG TTC AGC CAG      507
Thr Phe Glu Glu Ala Ser Asp Pro Val Val Pro Cys Glu Phe Ser Gln
         30                  35                  40

GCT CAG TAT GAC GAC TTC CAA TGG GAG CAA GTG CGG ATC CAC CCC GGC      555
Ala Gln Tyr Asp Asp Phe Gln Trp Glu Gln Val Arg Ile His Pro Gly
     45                  50                  55

ACC CGG ACC CCT GAA GAC CTG CCC CAT GGT GCC TAC TTG ATG GTC AAT      603
Thr Arg Thr Pro Glu Asp Leu Pro His Gly Ala Tyr Leu Met Val Asn
 60                  65                  70                  75

GCT TCT CAG CAT ACC CCA GGT CAG AGG GCC CAC ATC ATC TTC CAG ACC      651
Ala Ser Gln His Thr Pro Gly Gln Arg Ala His Ile Ile Phe Gln Thr
                 80                  85                  90

CTG AGC GAG AAC GAC ACC CAT TGT GTG CAG TTC AGC TAC TTC CTG TAC      699
Leu Ser Glu Asn Asp Thr His Cys Val Gln Phe Ser Tyr Phe Leu Tyr
             95                 100                 105

AGC AGG GAT GGG CAC AGC CCA GGC ACC CTG GGG GTC TAC GTG CGC GTG      747
Ser Arg Asp Gly His Ser Pro Gly Thr Leu Gly Val Tyr Val Arg Val
        110                 115                 120

AAT GGG GGC CCT CTG GGC AGT GCC GTG TGG AAT ATG ACC GGA TCC CAC      795
Asn Gly Gly Pro Leu Gly Ser Ala Val Trp Asn Met Thr Gly Ser His
    125                 130                 135

GGC CGT CAG TGG CAC CAG GCT GAG CTG GCT GTC AGC ACC TTC TGG CCC      843
Gly Arg Gln Trp His Gln Ala Glu Leu Ala Val Ser Thr Phe Trp Pro
140                 145                 150                 155

AAT GAG TWT CAG GTG CTG TTT GAG GCC CTC ATC TCC CCA GAC CAC AAG      891
Asn Glu Xaa Gln Val Leu Phe Glu Ala Leu Ile Ser Pro Asp His Lys
                160                 165                 170

GGC TAC ATA GGC TTA GAC GAC ATC TTG CTC TTC AGC TAT CCC TGC GCA      939
Gly Tyr Ile Gly Leu Asp Asp Ile Leu Leu Phe Ser Tyr Pro Cys Ala
            175                 180                 185

AAG GCC CCT CAC TTC TCC CGC CTT GGG GAC GTG GAG GTC AAT GCA GGC      987
Lys Ala Pro His Phe Ser Arg Leu Gly Asp Val Glu Val Asn Ala Gly
        190                 195                 200

CAG AAC GCA TCC TTC CAA TGC ATG GCA GCA GGC AGA GCC GCA GAG GCA     1035
Gln Asn Ala Ser Phe Gln Cys Met Ala Ala Gly Arg Ala Ala Glu Ala
```

-continued

```
    205                 210                 215

GAA CAC TTC TTC CTG CAG CGT CAG AGT GGA GTG CTG GTG CCT GCG GCC      1083
Glu His Phe Phe Leu Gln Arg Gln Ser Gly Val Leu Val Pro Ala Ala
220                 225                 230                 235

GGG GTG CGG CAC ATC AGT CAC CGT CGC TTC CTG GCC ACT TTT CCG CTG      1131
Gly Val Arg His Ile Ser His Arg Arg Phe Leu Ala Thr Phe Pro Leu
                240                 245                 250

GCC TCG GTA GGC CGC TCA GAG CAG GAT CTG TAC CGT TGC GTG TCC CAG      1179
Ala Ser Val Gly Arg Ser Glu Gln Asp Leu Tyr Arg Cys Val Ser Gln
            255                 260                 265

GCC CCG CGT GGT GCT GGC GTC TCC AAC TTT GCA GAG CTC ATC GTC AAA      1227
Ala Pro Arg Gly Ala Gly Val Ser Asn Phe Ala Glu Leu Ile Val Lys
        270                 275                 280

GAG CCT CCC ACC CCC ATC GCG CCC CCA CAG CTG CTG CGT GCA GGC CCC      1275
Glu Pro Pro Thr Pro Ile Ala Pro Pro Gln Leu Leu Arg Ala Gly Pro
    285                 290                 295

ACC TAC CTC ATT ATC CAG CTC AAC ACC AAC TCC ATC ATT GGC GAC GGG      1323
Thr Tyr Leu Ile Ile Gln Leu Asn Thr Asn Ser Ile Ile Gly Asp Gly
300                 305                 310                 315

CCG ATC GTG CGC AAG GAG ATC GAG TAC CGC ATG GCA CGG GGC CCG TGG      1371
Pro Ile Val Arg Lys Glu Ile Glu Tyr Arg Met Ala Arg Gly Pro Trp
                320                 325                 330

GCC GAG GTG CAC GCT GTC AAC CTG CAR ACC TAC AAG CTG TGG CAT CTG      1419
Ala Glu Val His Ala Val Asn Leu Xaa Thr Tyr Lys Leu Trp His Leu
            335                 340                 345

GAC CCA GAC ACT GAG TAT GAA ATC AGC GTG CTG CTC ACA CGC CCG GGA      1467
Asp Pro Asp Thr Glu Tyr Glu Ile Ser Val Leu Leu Thr Arg Pro Gly
        350                 355                 360

GAT GGA GGC ACA GGC CGC CCT GGG CCA CCA CTG ATC AGC CGG ACC AAG      1515
Asp Gly Gly Thr Gly Arg Pro Gly Pro Pro Leu Ile Ser Arg Thr Lys
    365                 370                 375

TGC GCA GAG CCC ACG AGG GCC CCC AAA GGT CTG GCT TTT GCT GAG ATC      1563
Cys Ala Glu Pro Thr Arg Ala Pro Lys Gly Leu Ala Phe Ala Glu Ile
380                 385                 390                 395

CAG GCT CGC CAG CTG ACC CTG CAG TGG GAG CCC CTG GGC TAT AAT GTC      1611
Gln Ala Arg Gln Leu Thr Leu Gln Trp Glu Pro Leu Gly Tyr Asn Val
                400                 405                 410

ACA CGT TGT CAT ACC TAC GCT GTG TCC CTT TGC TAT CGC TAC ACC CTG      1659
Thr Arg Cys His Thr Tyr Ala Val Ser Leu Cys Tyr Arg Tyr Thr Leu
            415                 420                 425

GGC GGC AGC CAC AAC CAG ACC ATC CGG GAG TGT GTG AAG ATG GAG CGG      1707
Gly Gly Ser His Asn Gln Thr Ile Arg Glu Cys Val Lys Met Glu Arg
        430                 435                 440

GGT GCC AGC CGC TAC ACC ATC AAG AAT CTG CTG CCA TTC AGA AAC ATC      1755
Gly Ala Ser Arg Tyr Thr Ile Lys Asn Leu Leu Pro Phe Arg Asn Ile
    445                 450                 455

CAC GTG CGT CTG ATT CTC ACA AAC CCT GAG GGG CGC AAG GAG GGC AAG      1803
His Val Arg Leu Ile Leu Thr Asn Pro Glu Gly Arg Lys Glu Gly Lys
460                 465                 470                 475

GAG GTC ACC TTC CAG ACA GAT GAA GAT GTG CCT GGT GGG ATT GCA GCT      1851
Glu Val Thr Phe Gln Thr Asp Glu Asp Val Pro Gly Gly Ile Ala Ala
                480                 485                 490

GAG TCC CTA ACC TTC ACT CCA CTG GAG GAC ATG ATC TTT CTC AAG TGG      1899
Glu Ser Leu Thr Phe Thr Pro Leu Glu Asp Met Ile Phe Leu Lys Trp
            495                 500                 505

GAG GAG CCC CAG GAG CCC AAT GGC CTC ATC ACT CAG TAT GAG ATC AGC      1947
Glu Glu Pro Gln Glu Pro Asn Gly Leu Ile Thr Gln Tyr Glu Ile Ser
        510                 515                 520

TAC CAA AGC ATT GAG TCC TCA GAC CCA GCA GTG AAC GTG CCC GGC CCG      1995
Tyr Gln Ser Ile Glu Ser Ser Asp Pro Ala Val Asn Val Pro Gly Pro
```

-continued

```
    525                 530                 535

AGA CGC ACC ATC TCC AAA CTC CGG AAT GAG ACT TAC CAC GTC TTC TCC      2043
Arg Arg Thr Ile Ser Lys Leu Arg Asn Glu Thr Tyr His Val Phe Ser
540                 545                 550                 555

AAC CTG CAT CCC GGC ACC ACG TAT CTG TTC TCC GTG CGT GCT CGG ACG      2091
Asn Leu His Pro Gly Thr Thr Tyr Leu Phe Ser Val Arg Ala Arg Thr
                560                 565                 570

AGC AAG GGC TTC GGC CAG GCG GCT CTC ACT GAG ATA ACC ACC AAC ATC      2139
Ser Lys Gly Phe Gly Gln Ala Ala Leu Thr Glu Ile Thr Thr Asn Ile
            575                 580                 585

TCA GCT CCC AGC TTT GAT TAT GCC GAC ATG CCG TCA CCC CTG GGC GAG      2187
Ser Ala Pro Ser Phe Asp Tyr Ala Asp Met Pro Ser Pro Leu Gly Glu
        590                 595                 600

TCC GAG AAC ACC ATC ACT GTG CTG TTG AGG CCG GCC CAG GGC CGA GGA      2235
Ser Glu Asn Thr Ile Thr Val Leu Leu Arg Pro Ala Gln Gly Arg Gly
    605                 610                 615

GCC CCC ATC AGC GTC TAC CAG GTG GTT GTG GAG GAA GAG CGG CCA CGG      2283
Ala Pro Ile Ser Val Tyr Gln Val Val Val Glu Glu Glu Arg Pro Arg
620                 625                 630                 635

CGC TTG CGG CGG GAG CCC GGA GCT CAG GAC TGC TTC TCG GTA CCT CTG      2331
Arg Leu Arg Arg Glu Pro Gly Ala Gln Asp Cys Phe Ser Val Pro Leu
                640                 645                 650

ACC TTT GAG ACG GCC CTG GCT CGC GGC CTG GTG CAC TAC TTT GGG GCT      2379
Thr Phe Glu Thr Ala Leu Ala Arg Gly Leu Val His Tyr Phe Gly Ala
            655                 660                 665

GAA CTG GCT GCC AGC AGC CTG CTT GAG GCC ATG CCC TTC ACC GTG GGT      2427
Glu Leu Ala Ala Ser Ser Leu Leu Glu Ala Met Pro Phe Thr Val Gly
        670                 675                 680

GAC AAC CAG ACC TAT CGT GGC TTC TGG AAC CCA CCG CTT GAG CCC AGA      2475
Asp Asn Gln Thr Tyr Arg Gly Phe Trp Asn Pro Pro Leu Glu Pro Arg
    685                 690                 695

AAG GCC TAT CTC ATC TAT TTC CAG GCA GCA AGC CAC CTG AAA GGG GAA      2523
Lys Ala Tyr Leu Ile Tyr Phe Gln Ala Ala Ser His Leu Lys Gly Glu
700                 705                 710                 715

ACC CGA CTG AAC TGC ATC CGA ATT GCC AGG AAA GCT GCG TGC AAG GAG      2571
Thr Arg Leu Asn Cys Ile Arg Ile Ala Arg Lys Ala Ala Cys Lys Glu
                720                 725                 730

AGC AAG CGA CCC CTC GAA GTG TCC CAG AGA TCG GAG GAG ATG GGG CTC      2619
Ser Lys Arg Pro Leu Glu Val Ser Gln Arg Ser Glu Glu Met Gly Leu
            735                 740                 745

ATC CTG GGC ATC TGT GCA GGT GGT CTT GCC GTC CTC ATT CTC CTC CTG      2667
Ile Leu Gly Ile Cys Ala Gly Gly Leu Ala Val Leu Ile Leu Leu Leu
        750                 755                 760

GGG GCC ATC ATT GTC ATC ATC CGC AAA GGG AAG CCA GTG AAC ATG ACG      2715
Gly Ala Ile Ile Val Ile Ile Arg Lys Gly Lys Pro Val Asn Met Thr
    765                 770                 775

AAA GCC ACG GTC AAC TAC CGC CAG GAG AAG ACT CAC ATG ATG AGT GCC      2763
Lys Ala Thr Val Asn Tyr Arg Gln Glu Lys Thr His Met Met Ser Ala
780                 785                 790                 795

GTG GAC CGC AGC TTC ACA GAT CAG AGT ACT CTG CAG GAG GAT GAG CGG      2811
Val Asp Arg Ser Phe Thr Asp Gln Ser Thr Leu Gln Glu Asp Glu Arg
                800                 805                 810

TTG GGT CTG TCC TTT ATG GAT GCT CCT GGC TAT AGT CCT CGT GGA GAC      2859
Leu Gly Leu Ser Phe Met Asp Ala Pro Gly Tyr Ser Pro Arg Gly Asp
            815                 820                 825

CAG CGA AGC GGT GGT GTC ACC GAG GCC AGC AGC CTC CTG GGG GGT TCT      2907
Gln Arg Ser Gly Gly Val Thr Glu Ala Ser Ser Leu Leu Gly Gly Ser
        830                 835                 840

CCA AGG CGC CCA TGC GGC CGG AAG GGT TCT CCG TAT CAT ACC GGG CAG      2955
Pro Arg Arg Pro Cys Gly Arg Lys Gly Ser Pro Tyr His Thr Gly Gln
```

```
    845               850               855

CTC CAC CCT GCA GTC CGA GTG GCT GAC CTT CTA CAG CAC ATC AAC CAG     3003
Leu His Pro Ala Val Arg Val Ala Asp Leu Leu Gln His Ile Asn Gln
860                 865                 870                 875

ATG AAG ACA GCC GAG GGC TAC GGC TTC AAG CAG GAG TAC GAG AGT TTC     3051
Met Lys Thr Ala Glu Gly Tyr Gly Phe Lys Gln Glu Tyr Glu Ser Phe
                880                 885                 890

TTT GAG GGC TGG GAC GCC ACC AAG AAG AAA GAC AAG CTC AAG GGC GGC     3099
Phe Glu Gly Trp Asp Ala Thr Lys Lys Lys Asp Lys Leu Lys Gly Gly
            895                 900                 905

CGA CAG GAG CCA GTG TCT GCC TAT GAT CGA CAC CAT GTG AAA CTA CAC     3147
Arg Gln Glu Pro Val Ser Ala Tyr Asp Arg His His Val Lys Leu His
        910                 915                 920

CCG ATG CTG GCA GAC CCT GAT GCC GAC TAC ATC TCT GCC AAC TAC ATA     3195
Pro Met Leu Ala Asp Pro Asp Ala Asp Tyr Ile Ser Ala Asn Tyr Ile
    925                 930                 935

GAC GGC TAC CAC AGG TCA AAC CAC TTC ATA GCC ACT CAA GGG CCA AAG     3243
Asp Gly Tyr His Arg Ser Asn His Phe Ile Ala Thr Gln Gly Pro Lys
940                 945                 950                 955

CCT GAG ATG ATC TAC GAT TTC TGG CGC ATG GTG TGG CAG GAA CAG TGT     3291
Pro Glu Met Ile Tyr Asp Phe Trp Arg Met Val Trp Gln Glu Gln Cys
                960                 965                 970

GCG AGC ATC GTC ATG ATC ACC AAG CTG GTA GAG GTG GGC AGG GTG AAG     3339
Ala Ser Ile Val Met Ile Thr Lys Leu Val Glu Val Gly Arg Val Lys
            975                 980                 985

TGT TCT CGC TAC TGG CCT GAG GAC TCA GAC ATG TAT GGG GAC ATC AAG     3387
Cys Ser Arg Tyr Trp Pro Glu Asp Ser Asp Met Tyr Gly Asp Ile Lys
        990                 995                 1000

ATC ACG CTG GTA AAG ACA GAG ACA CTG GCT GAG TAT GTG GTG CGC ACC     3435
Ile Thr Leu Val Lys Thr Glu Thr Leu Ala Glu Tyr Val Val Arg Thr
    1005                1010                1015

TTT GCC CTG GAG CGG AGA GGT TAC TCA GCC CGG CAT GAG GTC CGC CAG     3483
Phe Ala Leu Glu Arg Arg Gly Tyr Ser Ala Arg His Glu Val Arg Gln
1020                1025                1030                1035

TTC CAT TTC ACA GCG TGG CCA GAG CAT GGT GTC CCC TAC CAC GCC ACG     3531
Phe His Phe Thr Ala Trp Pro Glu His Gly Val Pro Tyr His Ala Thr
                1040                1045                1050

GGG CTG CTG GCC TTC ATC CGG CGT GTG AAG GCT TCC ACT CCA CCT GAT     3579
Gly Leu Leu Ala Phe Ile Arg Arg Val Lys Ala Ser Thr Pro Pro Asp
            1055                1060                1065

GCC GGG CCC ATT GTC ATT CAC TGC AGT GCA GGA ACT GGC CGC ACA GGC     3627
Ala Gly Pro Ile Val Ile His Cys Ser Ala Gly Thr Gly Arg Thr Gly
        1070                1075                1080

TGC TAC ATC GTC CTG GAT GTG ATG CTG GAC ATG GCT GAA TGT GAG GGG     3675
Cys Tyr Ile Val Leu Asp Val Met Leu Asp Met Ala Glu Cys Glu Gly
    1085                1090                1095

GTC GTG GAC ATT TAC AAC TGT GTG AAG ACC CTC TGT TCC CGA CGG GTC     3723
Val Val Asp Ile Tyr Asn Cys Val Lys Thr Leu Cys Ser Arg Arg Val
1100                1105                1110                1115

AAC ATG ATC CAG ACG GAG GAA CAA TAT ATC TTC ATC CAC GAT GCA ATC     3771
Asn Met Ile Gln Thr Glu Glu Gln Tyr Ile Phe Ile His Asp Ala Ile
                1120                1125                1130

TTG GAG GCC TGC CTG TGT GGG GAG ACC ACC ATC CCT GTC AAC GAG TTC     3819
Leu Glu Ala Cys Leu Cys Gly Glu Thr Thr Ile Pro Val Asn Glu Phe
            1135                1140                1145

AGG GCC ACC TAC AGG GAG ATG ATC CGC ATT GAC CCT CAG AGC AAT TCC     3867
Arg Ala Thr Tyr Arg Glu Met Ile Arg Ile Asp Pro Gln Ser Asn Ser
        1150                1155                1160

TCC CAG CTT CGG GAA GAG TTC CAG ACG CTG AAC TCG GTC ACG CCG CCG     3915
Ser Gln Leu Arg Glu Glu Phe Gln Thr Leu Asn Ser Val Thr Pro Pro
```

```
    1165                1170                1175

CTG GAT GTG GAG GAG TGT AGC ATT GCC CTG CTG CCC CGG AAT CGA GAC     3963
Leu Asp Val Glu Glu Cys Ser Ile Ala Leu Leu Pro Arg Asn Arg Asp
1180                1185                1190                1195

AAG AAC CGT AGC ATG GAT GTG CTG CCA CCA GAC CGC YGC CTG CCC TTC     4011
Lys Asn Arg Ser Met Asp Val Leu Pro Pro Asp Arg Xaa Leu Pro Phe
                1200                1205                1210

CTC ATC TCC AGT GAT GGG GAC CCC AAT AAC TAC ATC AAT GCA GCA CTG     4059
Leu Ile Ser Ser Asp Gly Asp Pro Asn Asn Tyr Ile Asn Ala Ala Leu
            1215                1220                1225

ACT GAC AGC TAC ACA CGG AGC GCC GCC TTC ATC GTG ACC CTG CAC CCG     4107
Thr Asp Ser Tyr Thr Arg Ser Ala Ala Phe Ile Val Thr Leu His Pro
        1230                1235                1240

CTG CAG AGT ACC ACG CCC GAC TTC TGG CGG CTG GTC TAC GAC TAC GGG     4155
Leu Gln Ser Thr Thr Pro Asp Phe Trp Arg Leu Val Tyr Asp Tyr Gly
    1245                1250                1255

TGC ACC TCC ATC GTC ATG CTG AAC CAA CTT AAC CAG TCC AAC TCC GCC     4203
Cys Thr Ser Ile Val Met Leu Asn Gln Leu Asn Gln Ser Asn Ser Ala
1260                1265                1270                1275

TGG CCC TGC TTG CAG TAC TGG CCG GAG CCA GGC CGA CAG CAG TAT GGG     4251
Trp Pro Cys Leu Gln Tyr Trp Pro Glu Pro Gly Arg Gln Gln Tyr Gly
                1280                1285                1290

CTC ATG GAG GTG GAG TTT GTG TCT GGC ACA GCA AAC GAG GAT TTG GTG     4299
Leu Met Glu Val Glu Phe Val Ser Gly Thr Ala Asn Glu Asp Leu Val
            1295                1300                1305

TCC CGA GTG TTC CGG GTG CAG AAC TCT TCT CGG CTG CAG GAG GGT CAC     4347
Ser Arg Val Phe Arg Val Gln Asn Ser Ser Arg Leu Gln Glu Gly His
        1310                1315                1320

CTG CTG GTA CGG CAC TTC CAG TTT CTG CGT TGG TCT GCT TAT CGG GAC     4395
Leu Leu Val Arg His Phe Gln Phe Leu Arg Trp Ser Ala Tyr Arg Asp
    1325                1330                1335

ACG CCT GAC TCC AGG AAG GCC TTT CTG CAC CTG TTG GCT GAG GTG GAC     4443
Thr Pro Asp Ser Arg Lys Ala Phe Leu His Leu Leu Ala Glu Val Asp
1340                1345                1350                1355

AAG TGG CAG GCA GAG AGT GGG GAT GGG CGC ACC GTG GTG CAT TGT CTC     4491
Lys Trp Gln Ala Glu Ser Gly Asp Gly Arg Thr Val Val His Cys Leu
                1360                1365                1370

AAC GGG GGT GGC CGC AGT GGC ACC TTC TGC GCC TGT GCC ACG GTC TTG     4539
Asn Gly Gly Gly Arg Ser Gly Thr Phe Cys Ala Cys Ala Thr Val Leu
            1375                1380                1385

GAG ATG ATC CGC TGT CAC AGC CTG GTG GAT GTT TTC TTT GCT GCC AAA     4587
Glu Met Ile Arg Cys His Ser Leu Val Asp Val Phe Phe Ala Ala Lys
        1390                1395                1400

ACA CTT CGG AAC TAC AAG CCC AAT ATG GTG GAG ACC ATG GAT CAG TAT     4635
Thr Leu Arg Asn Tyr Lys Pro Asn Met Val Glu Thr Met Asp Gln Tyr
    1405                1410                1415

CAT TTC TGC TAC GAC GTG GCC CTG GAG TAC CTG GAG GCT CTG GAG TTG     4683
His Phe Cys Tyr Asp Val Ala Leu Glu Tyr Leu Glu Ala Leu Glu Leu
1420                1425                1430                1435

AGA TAGCAGGCGC CTGACCTGGG GCACCCAGTG AACACCCAGG GCATGGCCCA          4736
Arg

TCATCCCAGA TGARGAGGGC CTGTGGCCCC AACTTTGCTC AGCCATAATT CCACAGGGAC   4796

AACACTGGAA CGGACGGACA CTGCACCATC TTGGTGACCC CCACGGGAAG GCTGCAGGCC   4856

AAGGAGAAGC TTTGCAAGAC TGTATCAGCC CCACCTCTAG AGGGCCCTGC AGACCTGTGC   4916

AGAGAAGCTC GCCTGGACCA AAATAGCTAG TGCTGGAGAG CACAGGCCAG GCCCCTCTGC   4976

TCCATCACAG TCCTTGGCCA GAAATGAATG AGTGTCTGCA GAGAGCACCC ATGGTTTGCA   5036

CCCAGTATGG TCCTTTCTGC ACGTGGTGGA GGCTCACTGG GACTTGGCAG GGGCTGAGTC   5096
```

```
CCCGAGAGTC CTGAAGCTGG GACTCTTCCC CGTCTCGCCG GTGGGACCCG CTGAGCATCC   5156

TGCAGCTCCA TTCTCCATCC CCACTGCCCC TACAGACCTG GGGTGCTTTG CTCGCTTTCC   5216

TCCTGCTTCT GAGCTTTTCC TGCAACAGGA CCCGTGCCTC CTTCCTGGGC TCCATCCCTG   5276

CCTGGCCCAG TATATGCAGA ATGATATACT TCAGCTCCTT CTTCCCCTGG CCTTTGGGTC   5336

TCCATGGTTC AGTCCTGCTC AGCTTGGGCC TGTGACAATC CACAAGGCTG AATCACAGCC   5396

CCTGGGGTTG AGGTCCCTGT GGCTCTTGGT GAGGCTGCCA CTGGATCGGG GCAGGCTAGA   5456

ACAGGGCTGG TGTCAGCTCC TAGAGTACAG AGGAAGAAGG GATACTTTGG AATGGAGGAC   5516

CAGTGCTTTT TTTGTTGTTG TTATTTTGTT ATTTTTTTGA TGGGAGGGTG GGAAGTTCTC   5576

TTTATAATGG GGTAGGCCAC ACCCCCATTT CGTGCCTCAA TTTCCCCATC TGTAAACTGT   5636

AGATATGACT ACTGACCTAC CTCACAGGGG GCTGTGGGGA GGTGTAAGGT AATGTTTGTA   5696

AAGCGCTTTG TAAATAAATG TGCTCTCTGA ATGCCAAAAA AAAAAAAAAA AAAAAAAAAA   5756

AAAAAAAAAA AAA                                                      5769
```

(2) INFORMATION FOR SEQ ID NO:2:

(i) SEQUENCE CHARACTERISTICS:
(A) LENGTH: 1436 amino acids
(B) TYPE: amino acid
(D) TOPOLOGY: linear (ii) MOLECULE TYPE: protein (xi) SEQUENCE DESCRIPTION: SEQ ID NO:2:

```
Met Ala Arg Ala Gln Ala Leu Val Leu Ala Leu Thr Phe Gln Phe Cys
  1               5                  10                  15

Ala Pro Glu Thr Glu Thr Pro Ala Ala Gly Cys Thr Phe Glu Glu Ala
             20                  25                  30

Ser Asp Pro Val Val Pro Cys Glu Phe Ser Gln Ala Gln Tyr Asp Asp
         35                  40                  45

Phe Gln Trp Glu Gln Val Arg Ile His Pro Gly Thr Arg Thr Pro Glu
     50                  55                  60

Asp Leu Pro His Gly Ala Tyr Leu Met Val Asn Ala Ser Gln His Thr
 65                  70                  75                  80

Pro Gly Gln Arg Ala His Ile Ile Phe Gln Thr Leu Ser Glu Asn Asp
                 85                  90                  95

Thr His Cys Val Gln Phe Ser Tyr Phe Leu Tyr Ser Arg Asp Gly His
            100                 105                 110

Ser Pro Gly Thr Leu Gly Val Tyr Val Arg Val Asn Gly Gly Pro Leu
        115                 120                 125

Gly Ser Ala Val Trp Asn Met Thr Gly Ser His Gly Arg Gln Trp His
    130                 135                 140

Gln Ala Glu Leu Ala Val Ser Thr Phe Trp Pro Asn Glu Xaa Gln Val
145                 150                 155                 160

Leu Phe Glu Ala Leu Ile Ser Pro Asp His Lys Gly Tyr Ile Gly Leu
                165                 170                 175

Asp Asp Ile Leu Leu Phe Ser Tyr Pro Cys Ala Lys Ala Pro His Phe
            180                 185                 190

Ser Arg Leu Gly Asp Val Glu Val Asn Ala Gly Gln Asn Ala Ser Phe
        195                 200                 205

Gln Cys Met Ala Ala Gly Arg Ala Ala Glu Ala Glu His Phe Phe Leu
    210                 215                 220

Gln Arg Gln Ser Gly Val Leu Val Pro Ala Ala Gly Val Arg His Ile
```

-continued

```
225                 230                 235                 240

Ser His Arg Arg Phe Leu Ala Thr Phe Pro Leu Ala Ser Val Gly Arg
                245                 250                 255

Ser Glu Gln Asp Leu Tyr Arg Cys Val Ser Gln Ala Pro Arg Gly Ala
            260                 265                 270

Gly Val Ser Asn Phe Ala Glu Leu Ile Val Lys Glu Pro Pro Thr Pro
        275                 280                 285

Ile Ala Pro Pro Gln Leu Leu Arg Ala Gly Pro Thr Tyr Leu Ile Ile
    290                 295                 300

Gln Leu Asn Thr Asn Ser Ile Ile Gly Asp Gly Pro Ile Val Arg Lys
305                 310                 315                 320

Glu Ile Glu Tyr Arg Met Ala Arg Gly Pro Trp Ala Glu Val His Ala
                325                 330                 335

Val Asn Leu Xaa Thr Tyr Lys Leu Trp His Leu Asp Pro Asp Thr Glu
            340                 345                 350

Tyr Glu Ile Ser Val Leu Leu Thr Arg Pro Gly Asp Gly Gly Thr Gly
        355                 360                 365

Arg Pro Gly Pro Pro Leu Ile Ser Arg Thr Lys Cys Ala Glu Pro Thr
    370                 375                 380

Arg Ala Pro Lys Gly Leu Ala Phe Ala Glu Ile Gln Ala Arg Gln Leu
385                 390                 395                 400

Thr Leu Gln Trp Glu Pro Leu Gly Tyr Asn Val Thr Arg Cys His Thr
                405                 410                 415

Tyr Ala Val Ser Leu Cys Tyr Arg Tyr Thr Leu Gly Gly Ser His Asn
            420                 425                 430

Gln Thr Ile Arg Glu Cys Val Lys Met Glu Arg Gly Ala Ser Arg Tyr
        435                 440                 445

Thr Ile Lys Asn Leu Leu Pro Phe Arg Asn Ile His Val Arg Leu Ile
    450                 455                 460

Leu Thr Asn Pro Glu Gly Arg Lys Glu Gly Lys Glu Val Thr Phe Gln
465                 470                 475                 480

Thr Asp Glu Asp Val Pro Gly Gly Ile Ala Ala Glu Ser Leu Thr Phe
                485                 490                 495

Thr Pro Leu Glu Asp Met Ile Phe Leu Lys Trp Glu Glu Pro Gln Glu
            500                 505                 510

Pro Asn Gly Leu Ile Thr Gln Tyr Glu Ile Ser Tyr Gln Ser Ile Glu
        515                 520                 525

Ser Ser Asp Pro Ala Val Asn Val Pro Gly Pro Arg Arg Thr Ile Ser
    530                 535                 540

Lys Leu Arg Asn Glu Thr Tyr His Val Phe Ser Asn Leu His Pro Gly
545                 550                 555                 560

Thr Thr Tyr Leu Phe Ser Val Arg Ala Arg Thr Ser Lys Gly Phe Gly
                565                 570                 575

Gln Ala Ala Leu Thr Glu Ile Thr Thr Asn Ile Ser Ala Pro Ser Phe
            580                 585                 590

Asp Tyr Ala Asp Met Pro Ser Pro Leu Gly Glu Ser Glu Asn Thr Ile
        595                 600                 605

Thr Val Leu Leu Arg Pro Ala Gln Gly Arg Gly Ala Pro Ile Ser Val
    610                 615                 620

Tyr Gln Val Val Val Glu Glu Glu Arg Pro Arg Arg Leu Arg Arg Glu
625                 630                 635                 640

Pro Gly Ala Gln Asp Cys Phe Ser Val Pro Leu Thr Phe Glu Thr Ala
                645                 650                 655
```

-continued

```
Leu Ala Arg Gly Leu Val His Tyr Phe Gly Ala Glu Leu Ala Ala Ser
            660                 665                 670

Ser Leu Leu Glu Ala Met Pro Phe Thr Val Gly Asp Asn Gln Thr Tyr
        675                 680                 685

Arg Gly Phe Trp Asn Pro Pro Leu Glu Pro Arg Lys Ala Tyr Leu Ile
    690                 695                 700

Tyr Phe Gln Ala Ala Ser His Leu Lys Gly Glu Thr Arg Leu Asn Cys
705                 710                 715                 720

Ile Arg Ile Ala Arg Lys Ala Ala Cys Lys Glu Ser Lys Arg Pro Leu
                725                 730                 735

Glu Val Ser Gln Arg Ser Glu Glu Met Gly Leu Ile Leu Gly Ile Cys
            740                 745                 750

Ala Gly Gly Leu Ala Val Leu Ile Leu Leu Leu Gly Ala Ile Ile Val
        755                 760                 765

Ile Ile Arg Lys Gly Lys Pro Val Asn Met Thr Lys Ala Thr Val Asn
    770                 775                 780

Tyr Arg Gln Glu Lys Thr His Met Met Ser Ala Val Asp Arg Ser Phe
785                 790                 795                 800

Thr Asp Gln Ser Thr Leu Gln Glu Asp Glu Arg Leu Gly Leu Ser Phe
                805                 810                 815

Met Asp Ala Pro Gly Tyr Ser Pro Arg Gly Asp Gln Arg Ser Gly Gly
            820                 825                 830

Val Thr Glu Ala Ser Ser Leu Leu Gly Gly Ser Pro Arg Arg Pro Cys
        835                 840                 845

Gly Arg Lys Gly Ser Pro Tyr His Thr Gly Gln Leu His Pro Ala Val
    850                 855                 860

Arg Val Ala Asp Leu Leu Gln His Ile Asn Gln Met Lys Thr Ala Glu
865                 870                 875                 880

Gly Tyr Gly Phe Lys Gln Glu Tyr Glu Ser Phe Phe Glu Gly Trp Asp
                885                 890                 895

Ala Thr Lys Lys Lys Asp Lys Leu Lys Gly Gly Arg Gln Glu Pro Val
            900                 905                 910

Ser Ala Tyr Asp Arg His His Val Lys Leu His Pro Met Leu Ala Asp
        915                 920                 925

Pro Asp Ala Asp Tyr Ile Ser Ala Asn Tyr Ile Asp Gly Tyr His Arg
    930                 935                 940

Ser Asn His Phe Ile Ala Thr Gln Gly Pro Lys Pro Glu Met Ile Tyr
945                 950                 955                 960

Asp Phe Trp Arg Met Val Trp Gln Glu Gln Cys Ala Ser Ile Val Met
                965                 970                 975

Ile Thr Lys Leu Val Glu Val Gly Arg Val Lys Cys Ser Arg Tyr Trp
            980                 985                 990

Pro Glu Asp Ser Asp Met Tyr Gly Asp Ile Lys Ile Thr Leu Val Lys
        995                 1000                1005

Thr Glu Thr Leu Ala Glu Tyr Val Val Arg Thr Phe Ala Leu Glu Arg
    1010                1015                1020

Arg Gly Tyr Ser Ala Arg His Glu Val Arg Gln Phe His Phe Thr Ala
1025                1030                1035                1040

Trp Pro Glu His Gly Val Pro Tyr His Ala Thr Gly Leu Leu Ala Phe
                1045                1050                1055

Ile Arg Arg Val Lys Ala Ser Thr Pro Pro Asp Ala Gly Pro Ile Val
            1060                1065                1070

Ile His Cys Ser Ala Gly Thr Gly Arg Thr Gly Cys Tyr Ile Val Leu
        1075                1080                1085
```

```
Asp Val Met Leu Asp Met Ala Glu Cys Glu Gly Val Val Asp Ile Tyr
    1090                1095                1100

Asn Cys Val Lys Thr Leu Cys Ser Arg Arg Val Asn Met Ile Gln Thr
1105                1110                1115                1120

Glu Glu Gln Tyr Ile Phe Ile His Asp Ala Ile Leu Glu Ala Cys Leu
                1125                1130                1135

Cys Gly Glu Thr Thr Ile Pro Val Asn Glu Phe Arg Ala Thr Tyr Arg
            1140                1145                1150

Glu Met Ile Arg Ile Asp Pro Gln Ser Asn Ser Ser Gln Leu Arg Glu
        1155                1160                1165

Glu Phe Gln Thr Leu Asn Ser Val Thr Pro Pro Leu Asp Val Glu Glu
    1170                1175                1180

Cys Ser Ile Ala Leu Leu Pro Arg Asn Arg Asp Lys Asn Arg Ser Met
1185                1190                1195                1200

Asp Val Leu Pro Pro Asp Arg Xaa Leu Pro Phe Leu Ile Ser Ser Asp
                1205                1210                1215

Gly Asp Pro Asn Asn Tyr Ile Asn Ala Ala Leu Thr Asp Ser Tyr Thr
            1220                1225                1230

Arg Ser Ala Ala Phe Ile Val Thr Leu His Pro Leu Gln Ser Thr Thr
        1235                1240                1245

Pro Asp Phe Trp Arg Leu Val Tyr Asp Tyr Gly Cys Thr Ser Ile Val
    1250                1255                1260

Met Leu Asn Gln Leu Asn Gln Ser Asn Ser Ala Trp Pro Cys Leu Gln
1265                1270                1275                1280

Tyr Trp Pro Glu Pro Gly Arg Gln Gln Tyr Gly Leu Met Glu Val Glu
                1285                1290                1295

Phe Val Ser Gly Thr Ala Asn Glu Asp Leu Val Ser Arg Val Phe Arg
            1300                1305                1310

Val Gln Asn Ser Ser Arg Leu Gln Glu Gly His Leu Leu Val Arg His
        1315                1320                1325

Phe Gln Phe Leu Arg Trp Ser Ala Tyr Arg Asp Thr Pro Asp Ser Arg
    1330                1335                1340

Lys Ala Phe Leu His Leu Leu Ala Glu Val Asp Lys Trp Gln Ala Glu
1345                1350                1355                1360

Ser Gly Asp Gly Arg Thr Val Val His Cys Leu Asn Gly Gly Gly Arg
                1365                1370                1375

Ser Gly Thr Phe Cys Ala Cys Ala Thr Val Leu Glu Met Ile Arg Cys
            1380                1385                1390

His Ser Leu Val Asp Val Phe Phe Ala Ala Lys Thr Leu Arg Asn Tyr
        1395                1400                1405

Lys Pro Asn Met Val Glu Thr Met Asp Gln Tyr His Phe Cys Tyr Asp
    1410                1415                1420

Val Ala Leu Glu Tyr Leu Glu Ala Leu Glu Leu Arg
1425                1430                1435
```

(2) INFORMATION FOR SEQ ID NO:3:

(i) SEQUENCE CHARACTERISTICS:
(A) LENGTH: 1457 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:3:

```
Met Asp Val Ala Ala Ala Ala Leu Pro Ala Phe Val Ala Leu Trp Leu
1               5                   10                  15

Leu Tyr Pro Trp Pro Leu Leu Gly Ser Ala Leu Gly Gln Phe Ser Ala
            20                  25                  30

Gly Gly Cys Thr Phe Asp Asp Gly Pro Gly Ala Cys Asp Tyr His Gln
        35                  40                  45

Asp Leu Tyr Asp Asp Phe Glu Trp Val His Val Ser Ala Gln Glu Pro
    50                  55                  60

His Tyr Leu Pro Pro Glu Met Pro Gln Gly Ser Tyr Met Val Val Asp
65                  70                  75                  80

Ser Ser Asn His Asp Pro Gly Glu Lys Ala Arg Leu Gln Leu Pro Thr
                85                  90                  95

Met Lys Glu Asn Asp Thr His Cys Ile Asp Phe Ser Tyr Leu Leu Tyr
            100                 105                 110

Ser Gln Lys Gly Leu Asn Pro Gly Thr Leu Asn Ile Leu Val Arg Val
        115                 120                 125

Asn Lys Gly Pro Leu Ala Asn Pro Ile Trp Asn Val Thr Gly Phe Thr
    130                 135                 140

Gly Arg Asp Trp Leu Arg Ala Glu Leu Ala Val Ser Thr Phe Trp Pro
145                 150                 155                 160

Asn Glu Tyr Gln Val Ile Phe Glu Ala Glu Val Ser Gly Gly Arg Ser
                165                 170                 175

Gly Tyr Ile Ala Ile Asp Asp Ile Gln Val Leu Ser Tyr Pro Cys Asp
            180                 185                 190

Lys Ser Pro His Phe Leu Arg Leu Gly Asp Val Glu Val Asn Ala Gly
        195                 200                 205

Gln Asn Ala Thr Phe Gln Cys Ile Ala Thr Gly Arg Asp Ala Val His
    210                 215                 220

Asn Lys Leu Trp Leu Gln Arg Arg Asn Gly Glu Asp Ile Pro Val Ala
225                 230                 235                 240

Gln Thr Lys Asn Ile Asn His Arg Arg Phe Ala Ala Ser Phe Arg Leu
                245                 250                 255

Gln Glu Val Thr Lys Thr Asp Gln Asp Leu Tyr Arg Cys Val Thr Gln
            260                 265                 270

Ser Glu Arg Gly Ser Gly Val Ser Asn Phe Ala Gln Leu Ile Val Arg
        275                 280                 285

Glu Pro Pro Arg Pro Ile Ala Pro Pro Gln Leu Leu Gly Val Gly Pro
    290                 295                 300

Thr Tyr Leu Leu Ile Gln Leu Asn Ala Asn Ser Ile Ile Gly Asp Gly
305                 310                 315                 320

Pro Ile Ile Leu Lys Glu Val Glu Tyr Arg Met Thr Ser Gly Ser Trp
                325                 330                 335

Thr Glu Thr His Ala Val Asn Ala Pro Thr Tyr Lys Leu Trp His Leu
            340                 345                 350

Asp Pro Asp Thr Glu Tyr Glu Ile Arg Val Leu Leu Thr Arg Pro Gly
        355                 360                 365

Glu Gly Gly Thr Gly Leu Pro Gly Pro Pro Leu Ile Thr Arg Thr Lys
    370                 375                 380

Cys Ala Glu Pro Met Arg Thr Pro Lys Thr Leu Lys Ile Ala Glu Ile
385                 390                 395                 400

Gln Ala Arg Arg Ile Ala Val Asp Trp Glu Ser Leu Gly Tyr Asn Ile
                405                 410                 415

Thr Arg Cys His Thr Phe Asn Val Thr Ile Cys Tyr His Tyr Phe Arg
            420                 425                 430
```

```
Gly His Asn Glu Ser Arg Ala Asp Cys Leu Asp Met Asp Pro Lys Ala
        435                 440                 445

Pro Gln His Val Val Asn His Leu Pro Pro Tyr Thr Asn Val Ser Leu
    450                 455                 460

Lys Met Ile Leu Thr Asn Pro Glu Gly Arg Lys Glu Ser Glu Glu Thr
465                 470                 475                 480

Ile Ile Gln Thr Asp Glu Asp Val Pro Gly Pro Val Pro Val Lys Ser
                485                 490                 495

Leu Gln Gly Thr Ser Phe Glu Asn Lys Ile Phe Leu Asn Trp Lys Glu
            500                 505                 510

Pro Leu Glu Pro Asn Gly Ile Ile Thr Gln Tyr Glu Val Ser Tyr Ser
        515                 520                 525

Ser Ile Arg Ser Phe Asp Pro Ala Val Pro Val Ala Gly Pro Pro Gln
    530                 535                 540

Thr Val Ser Asn Leu Trp Asn Ser Thr His His Val Phe Met His Leu
545                 550                 555                 560

His Pro Gly Thr Thr Tyr Gln Phe Phe Ile Arg Ala Ser Thr Val Lys
                565                 570                 575

Gly Phe Gly Pro Ala Thr Ala Ile Asn Val Thr Thr Asn Ile Ser Ala
            580                 585                 590

Pro Ser Leu Pro Asp Tyr Glu Gly Val Asp Ala Ser Leu Asn Glu Thr
        595                 600                 605

Ala Thr Thr Ile Thr Val Leu Leu Arg Pro Ala Gln Ala Lys Gly Ala
    610                 615                 620

Pro Ile Ser Ala Tyr Gln Ile Val Val Glu Gln Leu His Pro His Arg
625                 630                 635                 640

Thr Lys Arg Glu Ala Gly Ala Met Glu Cys Tyr Gln Val Pro Val Thr
                645                 650                 655

Tyr Gln Asn Ala Leu Ser Gly Gly Ala Pro Tyr Tyr Phe Ala Ala Glu
            660                 665                 670

Leu Pro Pro Gly Asn Leu Pro Glu Pro Ala Pro Phe Thr Val Gly Asp
        675                 680                 685

Asn Arg Thr Tyr Lys Gly Phe Trp Asn Pro Pro Leu Ala Pro Arg Lys
    690                 695                 700

Gly Tyr Asn Ile Tyr Phe Gln Ala Met Ser Ser Val Glu Lys Glu Thr
705                 710                 715                 720

Lys Thr Gln Cys Val Arg Ile Ala Thr Lys Ala Ala Ala Thr Glu Glu
                725                 730                 735

Pro Glu Val Ile Pro Asp Pro Ala Lys Gln Thr Asp Arg Val Val Lys
            740                 745                 750

Ile Ala Gly Ile Ser Ala Gly Ile Leu Val Phe Ile Leu Leu Leu Leu
        755                 760                 765

Val Val Ile Val Ile Val Lys Lys Ser Lys Leu Ala Lys Lys Arg Lys
    770                 775                 780

Asp Ala Met Gly Asn Thr Arg Gln Glu Met Thr His Met Val Asn Ala
785                 790                 795                 800

Met Asp Arg Ser Tyr Ala Asp Gln Ser Thr Leu His Ala Glu Asp Pro
                805                 810                 815

Leu Ser Leu Thr Phe Met Asp Gln His Asn Phe Ser Pro Arg Leu Pro
            820                 825                 830

Asn Asp Pro Leu Val Pro Thr Ala Val Leu Asp Glu Asn His Ser Ala
        835                 840                 845

Thr Ala Glu Ser Ser Arg Leu Leu Asp Val Pro Arg Tyr Leu Cys Glu
```

```
    850                 855                 860

Gly Thr Glu Ser Pro Tyr Gln Thr Gly Gln Leu His Pro Ala Ile Arg
865                 870                 875                 880

Val Ala Asp Leu Leu Gln His Ile Asn Leu Met Lys Thr Ser Asp Ser
                885                 890                 895

Tyr Gly Phe Lys Glu Glu Tyr Glu Ser Phe Phe Glu Gly Gln Ser Ala
            900                 905                 910

Ser Trp Asp Val Ala Lys Lys Asp Gln Asn Arg Ala Lys Asn Arg Tyr
        915                 920                 925

Gly Asn Ile Ile Ala Tyr Asp His Ser Arg Val Ile Leu Gln Pro Val
    930                 935                 940

Glu Asp Asp Pro Ser Ser Asp Tyr Ile Asn Ala Asn Tyr Ile Asp Ile
945                 950                 955                 960

Trp Leu Tyr Arg Asp Gly Tyr Gln Arg Pro Ser His Tyr Ile Ala Thr
                965                 970                 975

Gln Gly Pro Val His Glu Thr Val Tyr Asp Phe Trp Arg Met Val Trp
            980                 985                 990

Gln Glu Gln Ser Ala Cys Ile Val Met Val Thr Asn Leu Val Glu Val
        995                 1000                1005

Gly Arg Val Lys Cys Tyr Lys Tyr Trp Pro Asp Asp Thr Glu Val Tyr
    1010                1015                1020

Gly Asp Phe Lys Val Thr Cys Val Glu Met Glu Pro Leu Ala Glu Tyr
1025                1030                1035                1040

Val Val Arg Thr Phe Thr Leu Glu Arg Arg Gly Tyr Asn Glu Ile Arg
                1045                1050                1055

Glu Val Lys Gln Phe His Phe Thr Gly Trp Pro Asp His Gly Val Pro
            1060                1065                1070

Tyr His Ala Thr Gly Leu Leu Ser Phe Ile Arg Arg Val Lys Leu Ser
        1075                1080                1085

Asn Pro Pro Ser Ala Gly Pro Ile Val Val His Cys Ser Ala Gly Ala
    1090                1095                1100

Gly Arg Thr Gly Cys Tyr Ile Val Ile Asp Ile Met Leu Asp Met Ala
1105                1110                1115                1120

Glu Arg Glu Gly Val Val Asp Ile Tyr Asn Cys Val Lys Ala Leu Arg
                1125                1130                1135

Ser Arg Arg Ile Asn Met Val Gln Thr Glu Glu Gln Tyr Ile Phe Ile
            1140                1145                1150

His Asp Ala Ile Leu Glu Ala Cys Leu Cys Gly Glu Thr Ala Ile Pro
        1155                1160                1165

Val Cys Glu Phe Lys Ala Ala Tyr Phe Asp Met Ile Arg Ile Asp Ser
    1170                1175                1180

Gln Thr Asn Ser Ser His Leu Lys Asp Glu Phe Gln Thr Leu Asn Ser
1185                1190                1195                1200

Val Thr Pro Arg Leu Gln Ala Glu Asp Cys Ser Ile Ala Cys Leu Pro
                1205                1210                1215

Arg Asn His Asp Lys Asn Arg Phe Met Asp Met Leu Pro Pro Asp Arg
            1220                1225                1230

Cys Leu Pro Phe Leu Ile Thr Ile Asp Gly Glu Ser Ser Asn Tyr Ile
        1235                1240                1245

Asn Ala Ala Leu Met Asp Ser Tyr Arg Gln Pro Ala Ala Phe Ile Val
    1250                1255                1260

Thr Gln Tyr Pro Leu Pro Asn Thr Val Lys Asp Phe Trp Arg Leu Val
1265                1270                1275                1280
```

```
Tyr Asp Tyr Gly Cys Thr Ser Ile Val Met Leu Asn Glu Val Asp Leu
                1285                1290                1295

Ser Gln Gly Cys Pro Gln Tyr Trp Pro Glu Glu Gly Met Leu Arg Tyr
            1300                1305                1310

Gly Pro Ile Gln Val Glu Cys Met Ser Cys Ser Met Asp Cys Asp Val
        1315                1320                1325

Ile Asn Arg Ile Phe Arg Ile Cys Asn Leu Thr Arg Pro Gln Glu Gly
    1330                1335                1340

Tyr Leu Met Val Gln Gln Phe Gln Tyr Leu Gly Trp Ala Ser His Arg
1345                1350                1355                1360

Glu Val Pro Gly Ser Lys Arg Ser Phe Leu Lys Leu Ile Leu Gln Val
                1365                1370                1375

Glu Lys Trp Gln Glu Glu Cys Glu Glu Gly Glu Gly Arg Thr Ile Ile
            1380                1385                1390

His Cys Leu Asn Gly Gly Gly Arg Ser Gly Met Phe Cys Ala Ile Gly
        1395                1400                1405

Ile Val Val Glu Met Val Lys Arg Gln Asn Val Val Asp Val Phe His
    1410                1415                1420

Ala Val Lys Thr Leu Arg Asn Ser Lys Pro Asn Met Val Glu Ala Pro
1425                1430                1435                1440

Glu Gln Tyr Arg Phe Cys Tyr Asp Val Ala Leu Glu Tyr Leu Glu Ser
                1445                1450                1455

Ser
```

(2) INFORMATION FOR SEQ ID NO:4:

(i) SEQUENCE CHARACTERISTICS:
(A) LENGTH: 1452 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:4:

```
Met Arg Thr Leu Gly Thr Cys Leu Val Thr Leu Ala Gly Leu Leu Leu
1               5                   10                  15

Thr Ala Ala Gly Glu Thr Phe Ser Gly Gly Cys Leu Phe Asp Glu Pro
            20                  25                  30

Tyr Ser Thr Cys Gly Tyr Ser Gln Ala Asp Glu Asp Asp Phe Asn Trp
        35                  40                  45

Glu Gln Val Asn Thr Leu Thr Lys Pro Thr Ser Asp Pro Trp Met Pro
    50                  55                  60

Ser Gly Ser Phe Met Leu Val Asn Thr Ser Gly Lys Pro Glu Gly Gln
65                  70                  75                  80

Arg Ala His Leu Leu Leu Pro Gln Leu Lys Glu Asn Asp Thr His Cys
                85                  90                  95

Ile Asp Phe His Tyr Phe Val Ser Ser Lys Ser Asn Ala Ala Pro Gly
            100                 105                 110

Leu Leu Asn Val Tyr Val Lys Val Asn Asn Gly Pro Leu Gly Asn Pro
        115                 120                 125

Ile Trp Asn Ile Ser Gly Asp Pro Thr Arg Thr Trp His Arg Ala Glu
    130                 135                 140

Leu Ala Ile Ser Thr Phe Trp Pro Asn Phe Tyr Gln Val Ile Phe Glu
145                 150                 155                 160

Val Val Thr Ser Gly His Gln Gly Tyr Leu Ala Ile Asp Glu Val Lys
                165                 170                 175
```

```
Val Leu Gly His Pro Cys Thr Arg Thr Pro His Phe Leu Arg Ile Gln
            180                 185                 190

Asn Val Glu Val Asn Ala Gly Gln Phe Ala Thr Phe Gln Cys Ser Ala
        195                 200                 205

Ile Gly Arg Thr Val Ala Gly Asp Arg Leu Trp Leu Gln Gly Ile Asp
    210                 215                 220

Val Arg Asp Ala Pro Leu Lys Glu Ile Lys Val Thr Ser Ser Arg Arg
225                 230                 235                 240

Phe Ile Ala Ser Phe Asn Val Val Asn Thr Thr Lys Arg Asp Ala Gly
                245                 250                 255

Lys Tyr Arg Cys Met Ile Cys Thr Glu Gly Gly Val Gly Ile Ser Asn
            260                 265                 270

Tyr Ala Glu Leu Val Val Lys Glu Pro Pro Val Pro Ile Ala Pro Pro
        275                 280                 285

Gln Leu Ala Ser Val Gly Ala Thr Tyr Leu Trp Ile Gln Leu Asn Ala
    290                 295                 300

Asn Ser Ile Asn Gly Asp Gly Pro Ile Val Ala Arg Glu Val Glu Tyr
305                 310                 315                 320

Cys Thr Ala Ser Gly Ser Trp Asn Asp Arg Gln Pro Val Asp Ser Thr
                325                 330                 335

Ser Tyr Lys Ile Gly His Leu Asp Pro Asp Thr Glu Tyr Glu Ile Ser
            340                 345                 350

Val Leu Leu Thr Arg Pro Gly Glu Gly Gly Thr Gly Ser Pro Gly Pro
        355                 360                 365

Ala Leu Arg Thr Arg Thr Lys Cys Ala Asp Pro Met Arg Gly Pro Arg
    370                 375                 380

Lys Leu Glu Val Val Glu Val Lys Ser Arg Gln Ile Thr Ile Arg Trp
385                 390                 395                 400

Glu Pro Phe Gly Tyr Asn Val Thr Arg Cys His Ser Tyr Asn Leu Thr
                405                 410                 415

Val His Tyr Gly Tyr Gln Val Gly Gly Gln Glu Gln Val Arg Glu Glu
            420                 425                 430

Val Ser Trp Asp Thr Asp Asn Ser His Pro Gln His Thr Ile Thr Asn
        435                 440                 445

Leu Ser Pro Tyr Thr Asn Val Ser Val Lys Leu Ile Leu Met Asn Pro
    450                 455                 460

Glu Gly Arg Lys Glu Ser Gln Glu Leu Thr Val Gln Thr Asp Glu Asp
465                 470                 475                 480

Leu Pro Gly Ala Val Pro Thr Glu Ser Ile Gln Gly Ser Ala Phe Glu
                485                 490                 495

Glu Lys Ile Phe Leu Gln Trp Arg Glu Pro Thr Gln Thr Tyr Gly Val
            500                 505                 510

Ile Thr Leu Tyr Glu Ile Thr Tyr Lys Ala Val Ser Ser Phe Asp Pro
        515                 520                 525

Glu Ile Asp Leu Ser Asn Gln Ser Gly Arg Val Ser Lys Leu Gly Asn
    530                 535                 540

Glu Thr His Phe Leu Phe Phe Gly Leu Tyr Pro Gly Thr Thr Tyr Ser
545                 550                 555                 560

Phe Thr Ile Arg Ala Ser Thr Ala Lys Gly Phe Gly Pro Pro Ala Thr
                565                 570                 575

Asn Gln Phe Thr Thr Lys Ile Ser Ala Pro Ser Met Pro Ala Tyr Glu
            580                 585                 590

Phe Glu Thr Pro Leu Asn Gln Thr Asp Asn Thr Val Thr Val Met Leu
```

```
        595                 600                 605

Lys Pro Ala Gln Ser Arg Gly Ala Pro Val Ser Val Tyr Gln Ile Val
    610                 615                 620

Val Glu Glu Glu Arg Pro Arg Arg Thr Lys Lys Thr Thr Glu Ile Leu
625                 630                 635                 640

Lys Cys Tyr Pro Val Pro Ile His Phe Gln Asn Ala Ser Ile Leu Asn
                645                 650                 655

Ser Gln Tyr Tyr Phe Ala Ala Glu Phe Pro Ala Asp Ser Leu Gln Ala
            660                 665                 670

Ala Gln Pro Phe Thr Ile Gly Asp Asn Lys Thr Tyr Asn Gly Tyr Trp
        675                 680                 685

Asn Thr Pro Leu Leu Pro His Lys Ser Tyr Arg Ile Tyr Tyr Gln Ala
    690                 695                 700

Ala Ser Arg Ala Asn Gly Glu Thr Lys Ile Asp Cys Val Arg Val Ala
705                 710                 715                 720

Thr Lys Gly Ala Val Thr Pro Lys Pro Val Pro Glu Pro Glu Lys Gln
                725                 730                 735

Thr Asp His Thr Val Lys Ile Ala Gly Val Ile Ala Gly Ile Leu Leu
            740                 745                 750

Phe Val Ile Ile Phe Leu Gly Val Val Leu Val Met Lys Lys Arg Lys
        755                 760                 765

Leu Ala Lys Lys Arg Lys Glu Thr Met Ser Ser Thr Arg Gln Glu Met
    770                 775                 780

Thr Val Met Val Asn Ser Met Asp Lys Ser Tyr Ala Glu Gln Gly Thr
785                 790                 795                 800

Asn Cys Asp Glu Ala Phe Ser Phe Met Gly Thr His Asn Leu Asn Gly
                805                 810                 815

Arg Ser Val Ser Ser Pro Ser Ser Phe Thr Met Lys Thr Asn Thr Leu
            820                 825                 830

Ser Thr Ser Val Pro Asn Ser Tyr Tyr Pro Asp Glu Thr His Thr Met
        835                 840                 845

Ala Ser Asp Thr Ser Ser Leu Ala Gln Pro His Thr Tyr Lys Lys Arg
    850                 855                 860

Glu Ala Ala Asp Val Pro Tyr Gln Thr Gly Gln Leu His Pro Ala Ile
865                 870                 875                 880

Arg Val Ala Asp Leu Leu Gln His Ile Thr Gln Met Lys Cys Ala Glu
                885                 890                 895

Gly Tyr Gly Phe Lys Glu Glu Tyr Glu Ser Phe Phe Glu Gly Gln Ser
            900                 905                 910

Ala Pro Trp Asp Ser Ala Lys Lys Asp Glu Asn Arg Met Lys Asn Arg
        915                 920                 925

Tyr Gly Asn Ile Ile Ala Tyr Asp His Ser Arg Val Arg Leu Gln Met
    930                 935                 940

Leu Glu Gly Asp Asn Asn Ser Asp Tyr Ile Asn Gly Asn Tyr Ile Asp
945                 950                 955                 960

Gly Tyr His Arg Pro Asn His Tyr Ile Ala Thr Gln Gly Pro Met Gln
                965                 970                 975

Glu Thr Ile Tyr Asp Phe Trp Arg Met Val Trp His Glu Asn Thr Ala
            980                 985                 990

Ser Ile Ile Met Val Thr Asn Leu Val Glu Val Gly Arg Val Lys Cys
        995                 1000                1005

Cys Lys Tyr Trp Pro Asp Asp Thr Glu Ile Tyr Lys Asp Ile Lys Val
    1010                1015                1020
```

-continued

```
Thr Leu Ile Asp Thr Glu Leu Leu Ala Glu Tyr Val Ile Arg Thr Phe
1025                1030                1035                1040

Ala Val Glu Lys Arg Gly Ile His Glu Ile Arg Glu Ile Arg Gln Phe
                1045                1050                1055

His Phe Thr Gly Trp Pro Asp His Gly Val Pro Tyr His Ala Thr Gly
            1060                1065                1070

Leu Leu Gly Phe Val Arg Gln Val Lys Ser Lys Ser Pro Pro Asn Ala
        1075                1080                1085

Gly Pro Leu Val Val His Cys Ser Ala Gly Ala Gly Arg Thr Gly Cys
    1090                1095                1100

Phe Ile Val Ile Asp Ile Met Leu Asp Met Ala Glu Arg Glu Gly Val
1105                1110                1115                1120

Val Asp Ile Tyr Asn Cys Val Arg Glu Leu Arg Ser Arg Arg Val Asn
                1125                1130                1135

Met Val Gln Thr Glu Glu Gln Tyr Val Phe Ile His Asp Ala Ile Leu
            1140                1145                1150

Glu Ala Cys Leu Cys Gly Asp Thr Ser Ile Pro Ala Ser Gln Val Arg
        1155                1160                1165

Ser Leu Tyr Tyr Asp Met Asn Lys Leu Asp Pro Gln Thr Asn Ser Ser
    1170                1175                1180

Gln Ile Lys Glu Glu Phe Arg Thr Leu Asn Met Val Thr Pro Thr Leu
1185                1190                1195                1200

Arg Val Glu Asp Cys Ser Ile Ala Leu Leu Pro Arg Asn His Glu Lys
                1205                1210                1215

Asn Arg Cys Met Asp Ile Leu Pro Pro Asp Arg Cys Leu Pro Phe Leu
            1220                1225                1230

Ile Thr Ile Asp Gly Glu Ser Ser Asn Tyr Ile Asn Ala Ala Leu Met
        1235                1240                1245

Asp Ser Tyr Lys Gln Pro Ser Ala Phe Ile Val Thr Gln His Pro Leu
    1250                1255                1260

Pro Asn Thr Val Lys Asp Phe Trp Arg Leu Val Leu Asp Tyr His Cys
1265                1270                1275                1280

Thr Ser Val Val Met Leu Asn Asp Val Asp Pro Ala Gln Leu Cys Pro
                1285                1290                1295

Gln Tyr Trp Pro Glu Asn Gly Val His Arg His Gly Pro Ile Gln Val
            1300                1305                1310

Glu Phe Val Ser Ala Asp Leu Glu Glu Asp Ile Ile Ser Arg Ile Phe
        1315                1320                1325

Arg Ile Tyr Asn Ala Ser Arg Pro Gln Asp Gly His Arg Met Val Gln
    1330                1335                1340

Gln Phe Gln Phe Leu Gly Trp Pro Met Tyr Arg Asp Thr Pro Val Ser
1345                1350                1355                1360

Lys Arg Ser Phe Leu Lys Leu Ile Arg Gln Val Asp Lys Trp Gln Glu
                1365                1370                1375

Glu Tyr Asn Gly Gly Glu Gly Pro Thr Val Val His Cys Leu Asn Gly
            1380                1385                1390

Gly Gly Arg Ser Gly Thr Phe Cys Ala Ile Ser Ile Val Cys Glu Met
        1395                1400                1405

Leu Arg His Gln Arg Thr Val Asp Val Phe His Ala Val Lys Thr Leu
    1410                1415                1420

Arg Asn Asn Lys Pro Asn Met Val Asp Leu Leu Asp Gln Tyr Lys Phe
1425                1430                1435                1440

Cys Tyr Glu Val Ala Leu Glu Tyr Leu Asn Ser Gly
                1445                1450
```

(2) INFORMATION FOR SEQ ID NO:5:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: protein (ix) FEATURE:
(A) NAME/KEY: Active-site
(B) LOCATION: 1..2
(D) OTHER INFORMATION: /note= "Let 'X' located at position 1 represent either Histidine or Aspartic Acid"

(ix) FEATURE:
(A) NAME/KEY: Modified-site
(B) LOCATION: 6..7
(D) OTHER INFORMATION: /note= "Let 'X' located at position 6 represent either Isoleucine or Valine."

(xi) SEQUENCE DESCRIPTION: SEQ ID NO:5:

Xaa Phe Trp Arg Met Xaa Trp
1 5

(2) INFORMATION FOR SEQ ID NO:6:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 11..12
(D) OTHER INFORMATION: /note= "Let the 'N' at position 11 represent Inosine."

(ix) FEATURE:
(A) NAME/KEY: misc_feature
(B) LOCATION: 17..18
(D) OTHER INFORMATION: /note= "Let the 'N' at position 17 represent Inosine."

(xi) SEQUENCE DESCRIPTION: SEQ ID NO:6:

AYTTYTGGMG NATGRTNTGG 20

(2) INFORMATION FOR SEQ ID NO:7:

(i) SEQUENCE CHARACTERISTICS:
(A) LENGTH: 7 amino acids
(B) TYPE: amino acid
(C) STRANDEDNESS:
(D) TOPOLOGY: linear (ii) MOLECULE TYPE: protein (ix) FEATURE:
(A) NAME/KEY: Modified-site
(B) LOCATION: 4..5
(D) OTHER INFORMATION: /note= "Let 'X' located at position 4 represent either Phenylalanine or Histidine."

(xi) SEQUENCE DESCRIPTION: SEQ ID NO:7:

Trp Pro Asp Xaa Gly Val Pro
1 5

```
(2) INFORMATION FOR SEQ ID NO:8:

     (i) SEQUENCE CHARACTERISTICS:
          (A) LENGTH: 17 base pairs
          (B) TYPE: nucleic acid
          (C) STRANDEDNESS: single
          (D) TOPOLOGY: linear

    (ii) MOLECULE TYPE: DNA (genomic)

    (ix) FEATURE:
          (A) NAME/KEY: misc_feature
          (B) LOCATION: 3..4
          (D) OTHER INFORMATION: /note= "Let 'N' located at position
                           3 represent Inosine."

    (ix) FEATURE:
          (A) NAME/KEY: misc_feature
          (B) LOCATION: 12..13
          (D) OTHER INFORMATION: /note= "Let 'N' located at position
                           12 represent Inosine."

    (xi) SEQUENCE DESCRIPTION: SEQ ID NO:8:

GGNACRWRRT CNGGCCA                                                   17


(2) INFORMATION FOR SEQ ID NO:9:

     (i) SEQUENCE CHARACTERISTICS:
          (A) LENGTH: 11 amino acids
          (B) TYPE: amino acid
          (C) STRANDEDNESS:
          (D) TOPOLOGY: linear

    (ii) MOLECULE TYPE: protein

    (xi) SEQUENCE DESCRIPTION: SEQ ID NO:9:

Asp Gly Asp Phe Glu Glu Ile Pro Glu Glu Tyr
1               5                   10


(2) INFORMATION FOR SEQ ID NO:10:

     (i) SEQUENCE CHARACTERISTICS:
          (A) LENGTH: 12 amino acids
          (B) TYPE: amino acid
          (C) STRANDEDNESS:
          (D) TOPOLOGY: linear

    (ii) MOLECULE TYPE: protein

    (xi) SEQUENCE DESCRIPTION: SEQ ID NO:10:

Glu Gly Pro Trp Leu Glu Glu Glu Glu Glu Ala Tyr
1               5                   10
```

κ/μ-LIKE PROTEIN TYROSINE PHOSPHATASE, PTP λ

This is a division of application Ser. No. 08/652,971 filed May 24, 1996, now U.S. Pat. No. 5,814,507.

FIELD OF THE INVENTION

This present invention concerns novel receptor protein tyrosine phosphatase polypeptides. More particularly, the present invention concerns a novel receptor protein tyrosine phosphatase designated herein as PTP λ.

BACKGROUND OF THE INVENTION

An extraordinary number of cellular processes are regulated by the tyrosine phosphorylation of a diversity of proteins. Tyrosine phosphorylation is induced by a plethora of receptor-like molecules as well as by a wide range of intracellular enzymes. The effects of tyrosine phosphorylation are numerous, and they modulate a range of developmental as well as other cellular operations. Of course, the importance of tyrosine phosphorylation is underlined by the need for mechanisms which carefully regulate the levels of these events. Thus, protein tyrosine kinases represent positive mediators of tyrosine phosphorylation, while protein tyrosine phosphatases (PTPs) induce the removal of phosphate from tyrosine. The balance of the levels of tyrosine phosphate is thus mediated by the relative activities of these two types of enzymes. It is therefore clear that the mechanisms which regulate cellular function via tyrosine phosphorylation require specific proteins which mediate both the upregulation as well as the downregulation of the levels of this modified amino acid.

PTPs represent a growing family of enzymes that are found in both receptor as well as non-receptor forms (Tonks, *Semin. Cell. Biol.* 4:373–453 (1993), Walton et al., *Ann. Rev. Biochem.* 62:101–120 (1993) and Sun et al., *Trends Biochem. Sci.* 19(11):480–485 (1994)). Non-receptor PTPs are a highly diverse kindred, and they contain a number of motifs, in addition to the enzymatically active PTP domain, that serve to regulate the region of the cell occupied by these proteins as well as the substrate specificity of these enzymes. The receptor PTPs are also a highly diverse group that are unified by the inclusion of a transmembrane domain which disposes them to the plasma membrane of the cell. Recently, the receptor PTPs have been subdivided into 8 types based upon their domain content (Brady-Kalnay et al., *Curr. Opin. Cell. Biol.* 7(5):650–657 (1995)). These subtypes all contain one or two PTPase domains on their cytoplasmic sides, with a variety of extracellular motifs including heavily O-glycosylated mucin-like domains (for example, CD45), chondroitin sulfate domains (for example, PTP γ) and short, highly glycosylated segments (for example, PTP α). The largest family of PTPs is the family which contains various motifs related to those found in adhesion molecules. These motifs include immunoglobulin-like (IgG) domains and fibronectin type III (FnIII) regions similar to those found in cell adhesion molecules such as ICAM, N-CAM and Ng-CAM (Rao et al., *J. Cell. Biol.* 118:937–949 (1992)). In addition, a subset of these adhesion-like PTPs, including the PTPs κ and μ, contain a third domain termed the MAM, for meprin/A5/PTP μ, motif (Beckman et al., *Trends Biochem. Sci.* 18:40–41 (1993)). The MAM motif has been previously shown to be involved with cell-cell recognition in neurons (Jiang et al., *J. Biol. Chem.* 267:9185–9193 (1992), Takagi et al., *Neuron* 7:295–307 (1991) and Hirata et al., *Neurosci. Res.* 17:159–169 (1993)). Interestingly, recent data suggest that three of these adhesion-like PTPs appear to be involved with neuronal pathfinding during Drosophila development (Desai et al, *Cell* 84:599–609 (1996) and Kreuger et al., *Cell* 84:611–622 (1996)). Together, these structural data are consistent with the conjecture that receptor PTPs encompass a diverse family of enzymatically active proteins which contain a number of interesting cell surface motifs potentially involved with the sensing of the extracellular environment.

PTPs κ and μ are the receptors that are most well characterized as adhesion molecules (Brady-Kalnay et al., supra, Jiang et al., *Mol. Cell. Biol.,* 13:2942–2951 (1993) and Gebbink et al., *Febs. Lett.* 290(1–2):123–130 (1991)). Both of these PTPs have been demonstrated to mediate homotypic adhesion. Thus, a diversity of assays, including cell- as well as molecule-based, have demonstrated that the extracellular domain of these enzymes can bind with high specificity in a homophilic manner (Brady-Kalnay et al., *J. Cell. Biol.* 268:961–972 (1993), Gebbink et al., *J. Biol. Chem.* 268:16101–16104 (1993) and Sap et al., *Mol. Cell. Biol.* 14:1–9 (1994)). Interestingly, mixing experiments have revealed that these closely related PTPs will not bind to each other in a heterophilic mode, suggesting that the extracellular domain is meant to recognize other cells specifically expressing identical receptors, a situation highly reminiscent of the cadherin homotypic adhesion system (Kemler et al., *Trends Genet.* 9:317–321 (1993)). While the extracellular domains required for this homotypic binding remain controversial, it appears likely that both the MAM motif as well as the IgG region are involved with homophilic interactions (Brady-Kalnay et al., *J. Biol. Chem.* 269:28472–28477 (1994) and Zondag et al., *J. Biol. Chem.* 270(24):14247–14250 (1995)). While these data suggest that these homophilic adhesion enzymes are involved with the recognition of other cells expressing similar types of receptors, other data have suggested that this recognition event may play a role in the attachment of such cells to each other. Thus, Tonks and colleagues have recently demonstrated that the receptor PTP μ specifically associates with the catenin/cadherin complex of homotypic cell adhesion molecules (Brady-Kalnay et al, *J. Cell. Biol.* 130(4):977–986 (1995)). They also demonstrated that treatment of cells with the PTP inhibitor pervanadate resulted in the upregulation of tyrosine phosphorylation of cadherins and catenins, a result which suggested a role for a PTP, potentially PTP μ, in the maintenance of the cadherin/catenin complex in an underphosphorylated state. Interestingly, previous work suggested that the level of tyrosine phosphorylation of this complex was correlated with the adhesive capacity of the cadherins (Beherns et al., *J. Cell. Biol.* 120:757–766 (1993)), a result which is consistent with the hypothesis that the adhesion between cells mediated by the cadherins might be regulated by their tyrosine phosphorylation levels as determined by homotypic interactions between receptor PTPs such as κ and μ.

The finding that PTPs κ and μ mediated homotypic adhesion, together with the somewhat restricted tissue distribution of these PTPs (Jiang et al., (1993) supra and Gebbink et al., (1991) supra), has suggested that additional members of this family of adhesive enzymes might exist. Here we report the cloning and characterization of the third member of this receptor PTP family, termed PTP λ. The PTP λ polypeptide reported here contains structural motifs that are very similar to those found in PTP κ and μ. In addition, this novel PTP λ receptor reveals a tissue distribution that is divergent from that previously described for the other members of this family.

SUMMARY OF THE INVENTION

We have analyzed a large number of PTPs from a primitive murine hematopoietic cell population using consensus PCR. From this population we have cloned a novel receptor protein tyrosine phosphorylase polypeptide which is related to the receptor PTPs κ and μ. We have designated this novel protein tyrosine phosphorylase as the "PTP λ". Unlike other known receptor PTP polypeptides, PTP λ is predominantly expressed in mammalian adult brain, lung and kidney tissues but predominantly lacks expression in mammalian adult liver tissue.

Accordingly, the present invention concerns an isolated receptor protein tyrosine phosphatase polypeptide (PTP) λ, which (1) is predominantly expressed in adult mammalian brain, lung and kidney tissue; and (2) predominantly lacks expression in adult mammalian liver tissue, wherein said polypeptide is capable of dephosphorylating phosphorylated tyrosine residues.

The present invention also concerns derivatives of these novel PTP polypeptides which substantially retain the ability to dephosphorylate phosphorylated tyrosine residues.

A preferred group of the PTP polypeptides of the present invention includes a polypeptide comprising the amino acid sequence shown in FIG. 1 (SEQ ID NO:2); a further mammalian homologue of amino acid sequence shown in FIG. 1 and a derivative of any of the above polypeptides which substantially retain the ability to dephosphorylate tyrosine residues.

In another aspect, the present invention is directed to agonists and antagonists of the above novel PTP polypeptides.

In yet another aspect, the present invention concerns isolated nucleic acid molecules encoding the novel PTP polypeptides disclosed herein.

In a further aspect, the invention concerns vectors comprising nucleic acid encoding the novel PTP polypeptides herein, operably linked to control sequences recognized by a host cell transformed with the vector, and to cells transformed with such vectors.

In a still further aspect of the present invention, there are provided antibodies capable of specific binding to the novel PTP polypeptides of this invention, and hybridoma cell lines producing such antibodies. The antibodies may be agonist antibodies, which stimulate the ability of the novel PTP polypeptides of the present invention to dephosphorylate tyrosines, or antagonist antibodies, which block this activity.

In yet a further aspect of the present invention, there is provided methods for producing the PTP polypeptides of the present invention comprising transforming a host cell with nucleic acid encoding said polypeptide, culturing the transformed cell and recovering said polypeptide from the cell culture.

The present invention further concerns an assay for identifying an antagonist or an agonist of a novel PTP polypeptide of the present invention, which comprises contacting a phosphatase domain of the PTP polypeptide with a candidate antagonist or agonist, and monitoring the ability of the phosphatase domain to dephosphorylate tyrosine residues.

BRIEF DESCRIPTION OF THE DRAWINGS

FIGS. 1A–1D. The cDNA and derived protein sequence of PTP λ. Illustrated is the cDNA (SEQ ID NO:1) and derived protein sequence (SEQ ID NO:2) of the full length PTP λ clone homologous to a small PCR fragment derived from hematopoietic progenitor cells using consensus PTP primers. Amino acids are presented by their standard one-letter designations.

FIGS. 2A–2B. Homology between PTP λ, PTP κ and PTP μ. Illustrated as boxed residues are the amino acid homologies between the PTP λ (ptplambda) (SEQ ID NO:2), PTP κ (ptpkappa) (SEQ ID NO:3) and PTP μ (ptpmu) (SEQ ID NO:4) polypeptides. Amino acids are presented by their standard one-letter designations. Also shown above the amino acid sequences are the domains predicted previously from PTP κ and PTP μ. These domains include the signal sequence (SS), the MAM (mePrin, A5, PTP μ), immunoglobulin-like (IgG), fibronectin type III-like (FnIII), transmembrane domain (TMD), cadherin-like (Cadherin) and dual phosphatase domains (PTPase I and PTPase II).

FIG. 3. Comparative domain structures of PTP λ, PTP κ and PTP μ. Illustrated are the percent amino acid homologies between the various domains of the PTP λ, PTP κ and PTP μ polypeptides. These domains include the signal sequence (SS), the MAM (mePrin, A5, PTP μ), immunoglobulin-like (IgG), fibronectin type III-like (FnIII), transmembrane domain (TMD), cadherin-like (Cadherin) and dual phosphatase domains (PTPase I and PTPase II).

FIG. 4. Tyrosine phosphatase activity of PTP λ immunoprecipitates from PC 12 cells. Lysates of PC 12 cells were immunoprecipitated with either preimmune antibody (Preimmune) or antibody directed against the cytoplasmic domain of the PTP λ polypeptide (AntiPTP λ). The immunoprecipitates were incubated with two different immobilized tyrosine phosphorylated peptides (PPS1 and PPS2) using a commercially available tyrosine phosphatase assay kit. Immunoprecipitates were done either in the absence or presence of the tyrosine phosphatase inhibitor vanadate. Tyrosine phosphatase activity was determined by examining the residual binding of an anti-phosphotyrosine antibody to the immobilized peptide, so that a decreased $OD_{405}$ correlates with tyrosine phosphatase activity.

FIG. 5. Northern blot analysis of PTP λ expression. Commercially available northern blots were probed with a $^{32}P$-labeled fragment of PTP λ using standard hybridization conditions. The blot on the left illustrates the PTP λ transcript in RNA obtained from murine embryos at the developmental day shown in the figure. The blot on the right illustrates an analysis of the PTP λ transcript in RNA from a. heart, b. brain, c. spleen, d. lung, e. liver, f. skeletal muscle, g. kidney and h. testis.

FIG. 6. PTP λ mRNA Expression In the E15.5 Rat Embryo. Emulsion autoradiographs of a sagittal embryo section (A), and higher magnifications of embryonic midbrain (C), spinal cord (D), kidney (F), and lung hybridized with a $^{33}P$-UTP labeled PTP λ antisense probe are shown. Opposed to the darkfield autoradiographs are the corresponding lightfield images of the sagittal embryo section (B), kidney (G), and lung (I). Hybridization using a PTP λ sense strand control probe is shown in an E15.5 embryonic spinal cord section (E). (A,B,C,D,E) Bar, 1.0 mm; (F,G,H,I) Bar, 0.2 mm.

FIG. 7. PTP λ mRNA Expression in P1 and Adult Rat Brain. Emulsion autoradiographs of coronal sections of P1 rat brain (A,B,C) and adult rat brain (D,E) hybridized with a $^{33}P$-UTP labeled PTP λ antisense probe are shown. Coronal sections of the P1 brain are at the level of the septum (A), hippocampus (B), and substantia nigra (C). For the adult animal, coronal brain sections are at the level of the septum (D) and the hippocampus and substantia nigra (E). Hybridization using a PTP λ sense strand control probe is shown in an adult coronal section at the level of the substantia nigra (F). (A,B,C) Bar, 1.0 mm; (D,E,F) Bar, 1.0 mm.

FIG. 8. Expression of PTP λ in PC 12 cells. Illustrated is the PTP λ transcript observed in RNA of PC 12 cells either untreated (−) or treated (+) with 10 ng/ml of nerve growth factor (NGF) for the days shown at the top of the figure. The lower blot shows the βactin signal obtained for each of the RNAs.

FIG. 9. Immunofluorescence analysis of PTP λ expression in PC 12 cells. PC 12 cells were either left untreated or treated with 10 ng/ml nerve growth factor (NGF) for 7 days to induce neurite formation. At the end of this time, the cells were permeabilized and stained with either pre-immune serum or antibodies directed against the intracellular domain of PTP λ. Cells were washed and observed by confocal fluorescence microscopy. Panel A shows the results without NGF band with pre-immune serum. Panel B shows the results without NGF and with anti-PTP λ serum. Panel C shows the results with NGF and anti-PTP λ serum. Panel D shows the results obtained with NGF and anti-PTP λ serum at a higher magnification than in Panel C. The arrows show positively stained extended neurites.

DETAILED DESCRIPTION OF THE INVENTION

A. Definitions

The phrases "receptor protein tyrosine phosphatase λ", "protein tyrosine phosphatase λ" and "PTP λ" are used interchangeably and refer to a native membrane-bound protein tyrosine phosphatase polypeptide which (1) is predominantly expressed in adult mammalian brain, lung and kidney tissue and (2) predominantly lacks expression in adult mammalian liver tissue, wherein the polypeptide is capable of dephosphorylating phosphorylated tyrosine residues. The above terms are also intended to encompass functional derivatives of such native tyrosine phosphatases.

The term "native tyrosine phosphatase" in this context refers to a naturally occurring tyrosine phosphatase polypeptide, having the described properties, of any human or non-human animal species, with or without the initiating methionine, whether purified from the native source, synthesized, produced by recombinant DNA technology or by any combination of these and/or other methods. Native PTP λ specifically includes the native murine PTP λ protein shown in FIG. 1 (SEQ ID NO:2).

A "functional derivative" of a polypeptide is a compound having a qualitative biological activity in common with the native polypeptide. Thus, a functional derivative of a native PTP λ polypeptide is a compound that has a qualitative biological activity in common with a native PTP λ polypeptide, for example, as being capable of dephosphorylating phosphorylated tyrosine residues. "Functional derivatives" include, but are not limited to, fragments of native polypeptides from any animal species (including humans), derivatives of native (human and non-human) polypeptides and their fragments, glycosylation variants of a native polypeptide, and peptide and non-peptide analogs of native polypeptides, provided that they have a biological activity in common with a respective native polypeptide. "Fragments" comprise regions within the sequence of a mature native polypeptide. The term "derivative" is used to define amino acid sequence variants, and covalent modifications of a native polypeptide. "Non-peptide analogs" are organic compounds which display substantially the same surface as peptide analogs of the native polypeptides. Thus, the non-peptide analogs of the native PTP λ of the present invention are organic compounds which display substantially the same surface as peptide analogs of the native PTP λ. Such compounds interact with other molecules in a similar fashion as the peptide analogs, and mimic a biological activity of a native PTP λ of the present invention.

The polypeptide functional derivatives of the native PTP λ of the present invention preferably have at least about 65%, more preferably at least about 75%, even more preferably at least about 85%, most preferably at least about 95% overall sequence homology with the amino acid sequence shown in FIG. 1 (SEQ ID NO:2) and substantially retain the ability to dephosphorylate phosphorylated tyrosine residues.

The term "biological activity" in the context of the definition of functional derivatives is defined as the possession of at least one adhesive, regulatory or effector function qualitatively in common with a native polypeptide (e.g. PTP λ). The functional derivatives of the native PTP λ of the present invention are unified by their qualitative ability to dephosphorylate phosphorylated tyrosine residues. Preferably, the functional derivatives of the native PTP λ polypeptides of the present invention qualitatively retain at least one of the following biological properties of the native molecules: mediation of cell adhesion, and involvement in neural pathfinding.

The terms "covalent modification" and "covalent derivatives" are used interchangeably and include, but are not limited to, modifications of a native polypeptide or a fragment thereof with an organic proteinaceous or non-proteinaceous derivatizing agent, fusions to heterologous polypeptide sequences, and post-translational modifications. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl, tyrosine or threonyl residues, methylation of the α-amino groups of lysine, arginine, and histidine side chains [T. E. Creighton, *Proteins: Structure and Molecular Properties*, W.H. Freeman & Co., San Francisco, pp. 79–86 (1983)]. Covalent derivatives/modifications specifically include fusion proteins comprising native PTP λ sequences of the present invention and their amino acid sequence variants, such as immunoadhesins, and N-terminal fusions to heterologous signal sequences.

"Predominantly expressed", "predominant expression" and grammatical equivalents thereof is defined as a level of expression of a nucleic acid encoding an amino acid sequence which is easily detectable using northern blot analysis under stringent conditions.

"Identity" or "homology" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology. Methods and computer programs for the alignment are well known in the art.

The term "agonist" is used to refer to peptide and non-peptide analogs of the native PTP λ of the present invention and to antibodies specifically binding native PTP λ provided that they retain at least one biological activity of a native PTP λ. Preferably, the agonists of the present invention retain the qualitative ability to dephosphorylate phosphorylated tyrosine residues.

The term "antagonist" is used to refer to a molecule inhibiting a biological activity of a native PTP λ of the present invention. Preferably, the antagonists herein inhibit the ability of the PTP λ of the present invention to dephosphorylate tyrosines. Preferred antagonists essentially completely block tyrosine dephosphorylation caused by PTP λ.

Ordinarily, the terms "amino acid" and "amino acids" refer to all naturally occurring L-α-amino acids. In some embodiments, however, D-amino acids may be present in the polypeptides or peptides of the present invention in order to facilitate conformational restriction. For example, in order to facilitate disulfide bond formation and stability, a D amino acid cysteine may be provided at one or both termini of a peptide functional derivative or peptide antagonist of the native PTP λ of the present invention. The amino acids are identified by either the single-letter or three-letter designations:

| | | | | | |
|---|---|---|---|---|---|
| Asp | D | aspartic acid | Ile | I | isoleucine |
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

These amino acids may be classified according to the chemical composition and properties of their side chains. They are broadly classified into two groups, charged and uncharged. Each of these groups is divided into subgroups to classify the amino acids more accurately:

I. Charged Amino Acids

Acidic Residues: aspartic acid, glutamic acid

Basic Residues: lysine, arginine, histidine

II. Uncharged Amino Acids

Hydrophilic Residues: serine, threonine, asparagine, glutamine

Aliphatic Residues: glycine, alanine, valine, leucine, isoleucine

Non-polar Residues: cysteine, methionine, proline

Aromatic Residues: phenylalanine, tyrosine, tryptophan

The term "amino acid sequence variant" refers to molecules with some differences in their amino acid sequences as compared to a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

"Antibodies (Abs)" and "immunoglobulin (Igs)" are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one and ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., *J. Mol. Biol.* 186, 651–663 [1985]; Novotny and Haber, *Proc. Natl. Acad. Sci. USA* 82, 4592–4596 [1985]).

The term "variable" refers to the fact that certain portions of the variable domains differ extensively in sequence among antibodies and are used in the binding and specificity of each particular antibody for its particular antigen. However, the variability is not evenly distributed through the variable domains of antibodies. It is concentrated in three segments called complementarity determining regions (CDRs) or hypervariable regions both in the light chain and the heavy chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat, E. A. et al., *Sequences of Proteins of Immunological Interest*, National Institute of Health, Bethesda, Md. [1991]). The constant domains are not involved directly in binding an antibody to an antigen, but exhibit various effector functions, such as participation of the antibody in antibody-dependent cellular toxicity.

Papain digestion of antibodies produces two identical antigen binding fragments, called Fab fragments, each with a single antigen binding site, and a residual "Fc" fragment, whose name reflects its ability to crystallize readily. Pepsin treatment yields an $F(ab')_2$ fragment that has two antigen combining sites and is still capable of cross-linking antigen.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other, chemical couplings of antibody fragments are also known.

The light chains of antibodies (immunoglobulins) from any vertebrate species can be assigned to one of two clearly distinct types, called kappa ($\kappa$) and lambda ($\lambda$), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g. IgG-1, IgG-2, IgG-3, and IgG-4; IgA-1 and IgA-2. The heavy chain constant domains that correspond to the different classes of immunoglobulins are called $\alpha$, delta, epsilon, $\gamma$, and $\mu$, respectively. The subunit structures and three-dimensional configurations of different classes of immunoglobulins are well known.

The term "antibody" is used in the broadest sense and specifically covers single monoclonal antibodies (including agonist and antagonist antibodies), antibody compositions with polyepitopic specificity, as well as antibody fragments (e.g., Fab, $F(ab')_2$, and Fv), so long as they exhibit the desired biological activity.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature* 256:495 (1975), or may be made by recombinant DNA methods [see, e.g. U.S. Pat. No. 4,816,567 (Cabilly et al.)].

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 (Cabilly et al.; Morrison et al., *Proc. Natl. Acad. Sci. USA* 81, 6851–6855 [1984]).

"Humanized" forms of non-human (e.g. murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see: Jones et al., *Nature* 321, 522–525 [1986]; Reichmann et al., *Nature* 332, 323–329 [1988]; EP-B-239 400 published Sep. 30, 1987; Presta, *Curr. Op. Struct. Biol.* 2 593–596 [1992]; and EP-B-451 216 published Jan. 24, 1996).

In the context of the present invention the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological property, as screened for in the originally transformed cell, are included.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

Nucleic acid is "operably linked" when it is placed into a functional relationship with another nucleic acid sequence.

For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

"Immunoadhesins" or "PTP λ—immunoglobulin chimeras" are chimeric antibody-like molecules that combine the functional domain(s) of a binding protein (usually a receptor, a cell-adhesion molecule or a ligand) with the an immunoglobulin sequence. The most common example of this type of fusion protein combines the hinge and Fc regions of an immunoglobulin (Ig) with domains of a cell-surface receptor that recognizes a specific ligand. This type of molecule is called an "immunoadhesin", because it combines "immune" and "adhesion" functions; other frequently used names are "Ig-chimera", "Ig-" or "Fc-fusion protein", or "receptor-globulin."

"Oligonucleotides" are short-length, single- or double-stranded polydeoxynucleotides that are chemically synthesized by known methods [such as phosphotriester, phosphite, or phosphoramidite chemistry, using solid phase techniques such as those described in EP 266,032, published May 4, 1988, or via deoxynucleoside H-phosphonate intermediates as described by Froehler et al., *Nucl. Acids Res.* 14, 5399 (1986). They are then purified on polyacrylamide gels.

Hybridization is preferably performed under "stringent conditions" which means (1) employing low ionic strength and high temperature for washing, for example, 0.015 sodium chloride/0.0015 M sodium citrate/0.1% sodium dodecyl sulfate at 50° C., or (2) employing during hybridization a denaturing agent, such as formamide, for example, 50% (vol/vol) formamide with 0.1% bovine serum albumin/ 0.1% Ficoll/0.1% polyvinylpyrrolidone/50 nM sodium phosphate buffer at pH 6.5 with 750 mM sodium chloride, 75 mM sodium citrate at 42° C. Another example is use of 50% formamide, 5×SSC (0.75 M NaCl, 0.075 M sodium citrate), 50 mM sodium phosphate (pH 6/8), 0.1% sodium pyrophosphate, 5×Denhardt's solution, sonicated salmon sperm DNA (50 $\mu$g/ml), 0.1% SDS, and 10% dextran sulfate at 42° C., with washes at 42° C. in 0.2×SSC and 0.1% SDS. Yet another example is hybridization using a buffer of 10% dextran sulfate, 2×SSC (sodium chloride/sodium citrate) and 50% formamide at 55° C., followed by a high-stringency wash consisting of 0.1×SSC containing EDTA at 55° C.

"Transformation" means introducing DNA into an organism so that the DNA is replicable, either as an extrachromosomal element or by chromosomal integration. Depending on the host cell used, transformation is done using standard techniques appropriate to such cells. The calcium treatment employing calcium chloride, as described by Cohen, S. N., *Proc. Natl. Acad. Sci.* (*USA*), 69, 2110 (1972) and Mandel et al. *J. Mol. Biol.* 53, 154 (1970), is generally used for prokaryotes or other cells that contain substantial cell-wall barriers. For mammalian cells without such cell walls, the calcium phosphate precipitation method of Graham, F. and van der Eb, A., *Virology,* 52, 456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen, P., et al. *J. Bact.,* 130, 946 (1977) and Hsiao, C. L., et al. *Proc. Natl. Acad. Sci.* (*USA*) 76, 3829 (1979). However, other methods for introducing DNA into cells such as by nuclear injection, electroporation or by protoplast fusion may also be used.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., *Nucleic Acids Res.* 9, 6103–6114 (1981) and D. Goeddel et al., *Nucleic Acids Res.* 8, 4057 (1980).

"Ligation" refers to the process of forming phosphodiester bonds between two double stranded nucleic acid fragments (T. Maniatis et al. 1982, supra, p. 146). Unless otherwise provided, ligation may be accomplished using known buffers and conditions with 10 units of T4 DNA ligase ("ligase") per 0.5 mg of approximately equimolar amounts of the DNA fragments to be ligated.

"Preparation" of DNA from transformants means isolating plasmid DNA from microbial culture. Unless otherwise provided, the alkaline/SDS method of Maniatis et al. 1982, supra, p. 90, may be used.

B. Production of PTP λ by recombinant DNA technology

1. Identification and isolation of nucleic acid encoding PTP λ

The native PTP λ proteins of the present invention may be isolated from cDNA or genomic libraries. For example, a suitable cDNA library can be constructed by obtaining polyadenylated mRNA from cells known to express the desired PTP λ protein, and using the mRNA as a template to synthesize double stranded cDNA. Suitable sources of the mRNA are murine primitive hematopoietic cells and PC12 cells. mRNA encoding the native PTP λ of the present invention is expressed, for example, in tissues derived from adult brain, lung, kidney, heart, skeletal muscle and testis. The gene encoding the novel PTP λ polypeptide of the present invention can also be obtained from a genomic library, such as a human genomic cosmid library, or a mouse-derived embryonic cell (ES) genomic library.

Libraries, either cDNA or genomic, are then screened with probes designed to identify the gene of interest or the protein encoded by it. For cDNA expression libraries, suitable probes include monoclonal and polyclonal antibodies that recognize and specifically bind to a PTP λ polypeptide. For cDNA libraries, suitable probes include carefully selected oligonucleotide probes (usually of about 20–80 bases in length) that encode known or suspected portions of a PTP λ polypeptide from the same or different species, and/or complementary or homologous cDNAs or fragments thereof that encode the same or a similar gene. Appropriate probes for screening genomic DNA libraries include, without limitation, oligonucleotides, cDNAs, or fragments thereof that encode the same or a similar gene, and/or homologous genomic DNAs or fragments thereof. Screening the cDNA or genomic library with the selected probe may be conducted using standard procedures as described in Chapters 10–12 of Sambrook et al., *Molecular Cloning: A Laboratory Manual*, New York, Cold Spring Harbor Laboratory Press, 1989.

If DNA encoding an enzyme of the present invention is isolated by using carefully selected oligonucleotide sequences to screen cDNA libraries from various tissues, the oligonucleotide sequences selected as probes should be sufficient in length and sufficiently unambiguous that false positives are minimized. The actual nucleotide sequence(s) is/are usually designed based on regions which have the least codon redundance. The oligonucleotides may be degenerate at one or more positions. The use of degenerate oligonucleotides is of particular importance where a library is screened from a species in which preferential codon usage is not known.

The oligonucleotide must be labeled such that it can be detected upon hybridization to DNA in the library being screened. The preferred method of labeling is to use ATP (e.g., $\gamma^{32}P$) and polynucleotide kinase to radiolabel the 5' end of the oligonucleotide. However, other methods may be used to label the oligonucleotide, including, but not limited to, biotinylation or enzyme labeling.

cDNAs encoding PTP λ can also be identified and isolated by other known techniques of recombinant DNA technology, such as by direct expression cloning, or by using the polymerase chain reaction (PCR) as described in U.S. Pat. No. 4,683,195, issued Jul. 28, 1987, in section 14 of Sambrook et al., supra, or in Chapter 15 of *Current Protocols in Molecular Biology*, Ausubel et al. eds., Greene Publishing Associates and Wiley-lnterscience 1991. The use of the PCR technique for obtaining cDNA encoding murine PTP λ is also illustrated in the examples.

Once cDNA encoding a PTP λ enzyme from one species has been isolated, cDNAs from other species can also be obtained by cross-species hybridization. According to this approach, human or other mammalian cDNA or genomic libraries are probed by labeled oligonucleotide sequences selected from known PTP λ sequences (such as murine PTP λ) in accord with known criteria, among which is that the sequence should be sufficient in length and sufficiently unambiguous that false positives are minimized. Typically, a $^{32}P$-labeled oligonucleotide having about 30 to 50 bases is sufficient, particularly if the oligonucleotide contains one or more codons for methionine or tryptophan. Isolated nucleic acid will be DNA that is identified and separated from contaminant nucleic acid encoding other polypeptides from the source of nucleic acid. Hybridization is preferably performed under "stringent conditions", as herein above defined.

Once the sequence is known, the gene encoding a particular PTP λ polypeptide can also be obtained by chemical synthesis, following one of the methods described in Engels and Uhlmann, *Agnew. Chem. Int. Ed. Engl.* 28, 716 (1989). These methods include triester, phosphite, phosphoramidite and H-phosphonate methods, PCR and other autoprimer methods, and oligonucleotide syntheses on solid supports.

2. Cloning and expression of nucleic acid encoding PTP λ

Once the nucleic acid encoding PTP λ is available, it is generally ligated into a replicable expression vector for further cloning (amplification of the DNA), or for expression.

Expression and cloning vectors are well known in the art and contain a nucleic acid sequence that enables the vector to replicate in one or more selected host cells. The selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA of expression of DNA) and the host cell for which it is compatible. The vector components generally include, but are not limited to, one or more of the following: a signal sequence, an origin of replication, one or more marker genes, an enhancer element, a promoter, and a transcription termination sequence. Construction of suitable vectors containing one or more of the above listed components, the desired coding and control sequences, employs standard ligation techniques. Isolated plasmids or DNA fragments are cleaved, tailored, and religated in the form desired to generate the plasmids required. For analysis to confirm correct sequences in plasmids constructed, the ligation mixtures are commonly used to transform *E. coli* cells, e.g. *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9, 309 (1981) or by the method of Maxam et al., *Methods in Enzymology* 65, 499 (1980).

The polypeptides of the present invention may be expressed in a variety of prokaryotic and eukaryotic host cells. Suitable prokaryotes include gram negative or gram positive organisms, for example *E. coli* or bacilli. A preferred cloning host is *E. coli* 294 (ATCC 31,446) although other gram negative or gram positive prokaryotes such as *E. coli* B, *E. coli* X1776 (ATCC 31,537), *E. coli* W3110 (ATCC 27,325), Pseudomonas species, or *Serratia Marcesans* are suitable.

In addition to prokaryotes, eukaryotic microbes such as filamentous fungi or yeast are suitable hosts for vectors herein. *Saccharomyces cerevisiae*, or common baker's yeast, is the most commonly used among lower eukaryotic host microorganisms. However, a number of other genera, species and strains are commonly available and useful herein, such as *S. pombe* [Beach and Nurse, *Nature* 290, 140 (1981)], *Kluyveromyces lactis* [Louvencourt et al., *J. Bacteriol.* 737 (1983)]; *yarrowia* (EP 402,226); *Pichia pastoris* (EP 183,070), *Trichoderma reesia* (EP 244,234), *Neurospora crassa* [Case et al., *Proc. Natl. Acad. Sci. USA* 76, 5259–5263 (1979)]; and Aspergillus hosts such as *A. nidulans* [Ballance et al., *Biochem. Biophys. Res. Commun.* 112, 284–289 (1983); Tilburn et al., *Gene* 26, 205–221 (1983); Yelton et al., *Proc. Natl. Acad. Sci. USA* 81, 1470–1474 (1984)] and *A. niger* [Kelly and Hynes, *EMBO J.* 4, 475–479 (1985)].

Suitable host cells may also derive from multicellular organisms. Such host cells are capable of complex processing and glycosylation activities. In principle, any higher eukaryotic cell culture is workable, whether from vertebrate or invertebrate culture, although cells from mammals such as humans are preferred. Examples of invertebrate cells include plants and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified. See, e.g. Luckow et al., *Bio/Technology* 6, 47–55 (1988); Miller et al., in *Genetic Engineering*, Setlow, J. K. et al., eds., Vol. 8 (Plenum Publishing, 1986), pp. 277–279; and Maeda et al., *Nature* 315, 592–594 (1985). A variety of such viral strains are publicly available, e.g. the L-1 variant of *Autographa californica* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which has been previously manipulated to contain the PTP λ DNA. During incubation of the plant cell culture with *A. tumefaciens*, the DNA encoding a PTP λ polypeptide is transferred to the plant cell host such that it is transfected, and will, under appropriate conditions, express the PTP λ DNA. In addition, regulatory and signal sequences compatible with plant cells are available, such as the nopaline synthase promoter and polyadenylation signal sequences. Depicker et al., *J. Mol. Appl. Gen.* 1, 561 (1982). In addition, DNA segments isolated from the upstream region of the T-DNA 780 gene are capable of activating or increasing transcription levels of plant-expressible genes in recombinant DNA-containing plant tissue. See EP 321,196 published Jun. 21, 1989.

However, interest has been greatest in vertebrate cells, and propagation of vertebrate cells in culture (tissue culture) is per se well known. See *Tissue Culture*, Academic Press, Kruse and Patterson, editors (1973). Examples of useful mammalian host cell lines are monkey kidney CV1 line transformed by SV40 (COS-7, ATCC CRL 1651); human embryonic kidney cell line [293 or 293 cells subcloned for growth in suspension culture, Graham et al, *J. Gen. Virol.* 36, 59 (1977)]; baby hamster kidney cells 9BHK, ATCC CCL 10); Chinese hamster ovary cells/DHFR [CHO, Urlaub and Chasin, *Proc. Natl. Acad. Sci. USA* 77, 4216 (1980)]; mouse sertolli cells [TM4, Mather, *Biol. Reprod.* 23, 243–251 (1980)]; monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL75); human liver cells (Hep G2, HB 8065); mouse mammary tumor (MMT 060562, ATCC CCL51); TRI cells [Mather et al., *Annals N.Y. Acad. Sci.* 383, 44068 (1982)]; MRC 5 cells; FS4 cells; and a human hepatoma cell line (Hep G2). Preferred host cells are human embryonic kidney 293 and Chinese hamster ovary cells.

Particularly useful in the practice of this invention are expression vectors that provide for the transient expression in mammalian cells of DNA encoding a PTP λ polypeptide. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient systems, comprising a suitable expression vector and a host cell, allow for the convenient positive identification of polypeptides encoded by clones DNAs, as well as for the rapid screening of such polypeptides for desired biological or physiological properties. Thus, transient expression systems are particularly useful in the invention for purposes of identifying analogs and variants of a PTP λ polypeptide.

Other methods, vectors, and host cells suitable for adaptation to the synthesis of the PTP λ polypeptides in recombinant vertebrate cell culture are described in Getting et al., *Nature* 293, 620–625 (1981); Mantel et al., *Nature* 281, 40–46 (1979); Levinson et al.; EP 117,060 and EP 117,058. Particularly useful plasmids for mammalian cell culture expression of the PTP λ polypeptides are pRK5 (EP 307, 247) or pSVI6B (PCT Publication No. WO 91/08291).

Other cloning and expression vectors suitable for the expression of the PTP λ polypeptides of the present invention in a variety of host cells are, for example, described in EP 457,758 published Nov. 27, 1991. A large variety of expression vectors are now commercially available. An exemplary commercial yeast expression vector is pPIC.9 (Invitrogen), while an commercially available expression vector suitable for transformation of *E. coli* cells is PET15b (Novagen).

C. Culturing the host cells

Prokaryote cells used to produce the PTP λ polypeptides of this invention are cultured in suitable media as describe generally in Sambrook et al., supra.

Mammalian cells can be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham and Wallace, *Meth. Enzymol.* 58, 44 (1979); Barnes and Sato, *Anal. Biochem.* 102, 255 (1980), U.S. Pat. Nos. 4,767,704; 4,657, 866; 4,927,762; or 4,560,655; WO 90/03430; WO 87/00195 or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug) trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH and the like, suitably are those previously used with the host cell selected for cloning or expression, as the case may be, and will be apparent to the ordinary artisan.

The host cells referred to in this disclosure encompass cells in in vitro cell culture as well as cells that are within a host animal or plant.

It is further envisioned that the PTP λ polypeptides of this invention may be produced by homologous recombination, or with recombinant production methods utilizing control elements introduced into cells already containing DNA encoding the particular PTP λ polypeptide.

D. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA* 77, 5201–5205 (1980)], dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as a site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to the surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hse et al., *Am. J. Clin. Pharm.* 75, 734–738 (1980).

Antibodies useful for immunohistochemical staining and/or assay of sample fluids may be either monoclonal or polyclonal, and may be prepared in any animal. Conveniently, the antibodies may be prepared against a native PTP λ polypeptide, or against a synthetic peptide based on the DNA sequence provided herein as described further hereinbelow.

E. Amino Acid Sequence Variants of Native PTP λ Polypeptides

Amino acid sequence variants of native PTP λ polypeptides are prepared by methods known in the art by introducing appropriate nucleotide changes into a PTP λ DNA, or by in vitro synthesis of the desired polypeptide. There are two principal variables in the construction of amino acid sequence variants: the location of the mutation site and the nature of the mutation. With the exception of naturally-occurring alleles, which do not require the manipulation of the DNA sequence encoding the PTP λ polypeptide, the amino acid sequence variants of PTP λ polypeptides are preferably constructed by mutating the DNA, either to arrive at an allele or an amino acid sequence variant that does not occur in nature.

One group of the mutations will be created within at least one of the phosphatase domains (PTPaseI and/or PTPaseII) of a native PTP λ protein. In view of the involvement of these domains in the enzymatic activity of PTP λ, amino acid alterations within these domains are expected to result in marked changes in the enzymatic properties of the native proteins. Non-conservative substitutions might ultimately result in PTP λ variants which lose the ability to dephosphatase tyrosines and will, therefore, be useful as antagonists of native PTP λ. PTP λ variants mutated to enhance the enzymatic activity of the native proteins may also be obtained, and will find use, for example, as potent mediators of cell adhesion.

Similarly, amino acid alterations in the MAM of IgG domains of the native PTP λ proteins are expected to affect the ability of these receptors to mediate homotypic cell adhesion, and the specificity of the homophilic interaction mediated.

Alternatively or in addition, amino acid alterations can be made at sites that differ in PTP λ proteins from various species, or in highly conserved regions, depending on the goal to be achieved. Sites at such locations will typically be modified in series, e.g. by (1) substituting first with conservative choices and then with more radical selections depending upon the results achieved, (2) deleting the target residue or residues, or (3) inserting residues of the same or different class adjacent to the located site, or combinations of options 1–3. One helpful technique is called "alanine scanning" (Cunningham and Wells, *Science* 244, 1081–1085 [1989]). The replacement of sequence motifs within the MAM, IgG, FNIII or PTPase domains of the native PTP λ proteins of the present invention by sequences from native PTP κ and/or PTP μ receptors is expected to result in variants having altered specificities.

In yet another group of the variant PTP λ polypeptides of the present invention, one or more of the functionally less significant domains may be deleted or inactivated. For example, the deletion or inactivation of the transmembrane domain yields soluble variants of the native protein. Alternatively, or in addition, the cytoplasmic domain may be deleted, truncated or otherwise altered.

Naturally-occurring amino acids are divided into groups based on common side chain properties:

(1) hydrophobic: norleucine, met, ala, val, leu, ile;

(2) neutral hydrophobic: cys, ser, thr;

(3) acidic: asp, glu;

(4) basic: asn, gin, his, lys, arg;

(5) residues that influence chain orientation: gly, pro; and (6) aromatic: trp, tyr, phe.

Conservative substitutions involve exchanging a member within one group for another member within the same group, whereas nonconservative substitutions will entail exchanging a member of one of these classes for another. Substantial changes in function or immunological identity are made by selecting substitutions that are less conservative, i.e. differ more significantly in their effect on maintaining (a) the structure of the polypeptide backbone in the area of substitution, for example as a sheet or helical conformation, (b) the charge or hydrophobicity of the molecule at the target site or (c) the bulk of the side chain. The substitutions which in general are expected to produce the greatest changes in the properties of the novel native PTP λ polypeptides of the present invention will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g. glycine.

Amino acid sequence deletions generally range from about 1 to 30 residues, more preferably about 1 to 10 residues, and typically are contiguous. Typically, the transmembrane and cytoplasmic domains, or only the cytoplasmic domains are deleted. However, deletion from the C-terminal to any other suitable N-terminal to the transmembrane region which preserves the biological activity or immunological cross-reactivity of a native PTP λ is suitable.

A preferred class of substitutional and/or deletional variants of the present invention are those involving a transmembrane region of a novel PTP λ molecule. Transmembrane regions are highly hydrophobic or lipophilic domains that are the proper size to span the lipid bilayer of the cellular membrane. They are believed to anchor the PTP λ protein in the cell membrane and allow for homotypic complex formation. Inactivation of the transmembrane domain, typically by deletion or substitution of transmembrane domain hydroxylation residues, will facilitate recovery and formulation by reducing its cellular or membrane lipid affinity and improving its aqueous solubility. If the transmembrane and cytoplasmic domains are deleted one avoids the introduction of potentially immunogenic epitopes, whether by exposure of otherwise intracellular polypeptides that might be recognized by the body as foreign or by insertion of heterologous polypeptides that are potentially immunogenic. Inactivation of the membrane binding function is accomplished by deletion of sufficient residues to produce a substantially hydrophilic hydropathy profile at this site or by substituting with heterologous residues which accomplish the same result.

A principle advantage of the transmembrane inactivated variants of the PTP λ polypeptides of the present invention is that they may be secreted into the culture medium of recombinant hosts. These variants are soluble in body fluids such as blood and do not have an appreciable affinity for cell membrane lipids, thus considerably simplifying their recovery from recombinant cell culture. As a general proposition, such soluble variants will not have a functional transmembrane domain and preferably will not have a functional cytoplasmic domain. For example, the transmembrane domain may be substituted by any amino acid sequence, e.g. a random or predetermined sequences of about 5 to 50 serine, threonine, lysine, arginine, glutamine, aspartic acid and like hydrophilic residues, which altogether exhibit a hydrophilic hydropathy profile. Like the deletional (truncated) soluble variants, these variants are secreted into the culture medium of recombinant hosts.

Amino acid insertions include amino- and/or carboxyl-terminal fusions ranging in length from one residue to polypeptides containing a hundred or more residues, as well as intrasequence insertions of single or multiple amino acid residues. Intrasequence insertions (i.e. insertions within the PTP λ protein amino acid sequence) may range generally from about 1 to 10 residues, more preferably 1 to 5 residues, more preferably 1 to 3 residues. Examples of terminal insertions include PTP λ polypeptides with an N-terminal methionyl residue, an artifact of its direct expression in bacterial recombinant cell culture, and fusion of a heterologous N-terminal signal sequence to the N-terminus of the PTP λ molecule to facilitate the secretion of the mature PTP λ from recombinant host cells. Such signal sequences will generally be obtained from, and thus homologous to, the intended host cell species. Suitable sequences include STII or lpp for *E. coli*, alpha factor for yeast, and viral signals such as herpes gD for mammalian cells.

Other insertional variants of the native PTP λ molecules include the fusion of the N- or C-terminus of the PTP λ molecule to immunogenic polypeptides, e.g. bacterial polypeptides such as beta-lactamase or an enzyme encoded by the *E. coli* trp locus, or yeast protein, and C-terminal fusions with proteins having a long half-life such as immunoglobulin regions (preferably immunoglobulin constant regions), albumin, or ferritin, as described in WO 89/02922 published on Apr. 6, 1989.

Further insertional variants are immunologically active derivatives of the novel PTP λ polypeptides, which comprise the PTP polypeptide and a polypeptide containing an epitope of an immunologically competent extraneous polypeptide, i.e. a polypeptide which is capable of eliciting an immune response in the animal to which the fusion is to be administered or which is capable of being bound by an antibody raised against an extraneous polypeptide. Typical examples of such immunologically competent polypeptides are allergens, autoimmune epitopes, or other potent immunogens or antigens recognized by pre-existing antibodies in the fusion recipient, including bacterial polypeptides such as trpLE, β- galactosidase, viral polypeptides such as herpes gD protein, and the like.

Immunogenic fusions are produced by cross-linking in vitro or by recombinant cell culture transformed with DNA encoding an immunogenic polypeptide. It is preferable that the immunogenic fusion be one in which the immunogenic sequence is joined to or inserted into a novel PTP λ molecule or fragment thereof by (a) peptide bond(s). These products therefore consist of a linear polypeptide chain containing the PTP λ epitope and at least one epitope foreign to the PTP λ polypeptide. It will be understood that it is within the scope of this invention to introduce the epitopes anywhere within a PTP λ molecule of the present invention or a fragment thereof. These immunogenic insertions are particularly useful when formulated into a pharmacologically acceptable carrier and administered to a subject in order to raise antibodies against the PTP λ molecule, which antibodies in turn are useful as diagnostics, in tissue-typing, or in purification of the novel PTP λ polypeptides by immunoaffinity techniques known per se. Alternatively, in the purification of the PTP λ polypeptides of the present invention, binding partners for the fused extraneous polypeptide, e.g. antibodies, receptors or ligands, are used to adsorb the fusion from impure admixtures, after which the fusion is eluted and, if desired, the novel PTP λ is recovered from the fusion, e.g. by enzymatic cleavage.

Since it is often difficult to predict in advance the characteristics of a variant PTP λ polypeptide, it will be appreciated that some screening will be needed to select the optimum variant.

After identifying the desired mutation(s), the gene encoding a PTP λ variant can, for example, be obtained by chemical synthesis as hereinabove described. More preferably, DNA encoding a PTP λ amino acid sequence variant is prepared by site-directed mutagenesis of DNA that encodes an earlier prepared variant or a nonvariant version of the PTP λ. Site-directed (site-specific) mutagenesis allows the production of PTP λ variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the techniques of site-specific mutagenesis are well known in the art, as exemplified by publications such as, Edelman et al., *DNA* 2, 183 (1983). As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, A. Walton, ed., Elsevier, Amsterdam (1981). This and other phage vectors are commercially available and their use is well known to those skilled in the art. A versatile and efficient procedure for the construction of oligodeoxyribonucleotide directed site-specific mutations in DNA fragments using M13-derived vectors was published by Zoller, M. J. and Smith, M., *Nucleic Acids Res.* 10, 6487–6500 [1982]). Also, plasmid vectors that contain a single-stranded phage origin of replication (Veira et al., *Meth. Enzymol.* 153, 3 [1987]) may be employed to obtain single-stranded DNA. Alternatively, nucleotide substitutions are introduced by synthesizing the appropriate DNA fragment in vitro, and amplifying it by PCR procedures known in the art.

The PCR technique may also be used in creating amino acid sequence variants of a PTP λ polypeptide. In a specific example of PCR mutagenesis, template plasmid DNA (1 $\mu$) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp$^R$ kits (obtained from Perkin-Elmer Cetus, Norwalk, Conn. and Emeryville, Calif.), and 25 pmole of each oligonucleotide primer, to a final volume of 50 $\mu$l. The reaction mixture is overlayered with 35 $\mu$l mineral oil. The reaction is denatured for 5 minutes at 100° C., placed briefly on ice, and then 1 μl *Thermus aquaticus* (Taq) DNA polymerase (5 units/ul), purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows:

2 min. 55° C., 30 sec. 72° C., then 19 cycles of the following:

30 sec. 94° C., 30 sec. 55° C., and 30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to appropriate treatments for insertion into a vector.

Another method for preparing variants, cassette mutagenesis, is based on the technique described by Wells et al. [*Gene* 34, 315 (1985)].

Additionally, the so-called phagemid display method may be useful in making amino acid sequence variants of native or variant PTP λ polypeptides or their fragments. This method involves (a) constructing a replicable expression vector comprising a first gene encoding a receptor to be mutated, a second gene encoding at least a portion of a natural or wild-type phage coat protein wherein the first and second genes are heterologous, and a transcription regulatory element operably linked to the first and second genes, thereby forming a gene fusion encoding a fusion protein; (b) mutating the vector at one or more selected positions within the first gene thereby forming a family of related plasmids; (c) transforming suitable host cells with the plasmids; (d) infecting the transformed host cells with a helper phage having a gene encoding the phage coat protein; (e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; (f) contacting the phagemid particles with a suitable antigen so that at least a portion of the phagemid particles bind to the antigen; and (g) separating the phagemid particles that bind from those that do not. Steps (d) through (g) can be repeated one or more times. Preferably in this method the plasmid is under tight control of the transcription regulatory element, and the culturing conditions are adjusted so that the amount or number of phagemid particles displaying more than one copy of the fusion protein on the surface of the particle is less than about 1%. Also, preferably, the amount of phagemid particles displaying more than one copy of the fusion protein is less than 10% of the amount of phagemid particles displaying a single copy of the fusion protein. Most preferably, the amount is less than 20%. Typically in this method, the expression vector will further contain a secretory signal sequence fused to the DNA encoding each subunit of the polypeptide and the transcription regulatory element will be a promoter system. Preferred promoter systems are selected from lac Z, $\lambda_{PL}$, tac, T7 polymerase, tryptophan, and alkaline phosphatase promoters and combinations thereof. Also, normally the method will employ a helper phage selected from M13K07, M13R408, M13-VCS, and Phi X 174. The preferred helper phage is M13K07, and the preferred coat protein is the M13 Phage gene III coat protein. The preferred host is *E. coli*, and protease-deficient strains of *E. coli.*

Further details of the foregoing and similar mutagenesis techniques are found in general textbooks, such as, for example, Sambrook et al., supra, and *Current Protocols in Molecular Biology*, Ausubel et al. eds., supra.

F. Glycosylation Variants

Glycosylation variants are included within the scope of the present invention. They include variants completely lacking in glycosylation (unglycosylated), variants having at least one less glycosylated site than the native form (deglycosylated) as well as variants in which the glycosylation has been changed. Included are deglycosylated and unglycosylated amino acid sequences variants, deglycosylated and unglycosylated native PTP λ, and other glycosylation variants. For example, substitutional or deletional mutagenesis may be employed to eliminate the N- or O-linked glycosylation sites in the a native or variant PTP λ molecule of the present invention, e.g. the asparagine residue may be deleted or substituted for another basic residue such as lysine or histidine. Alternatively, flanking residues making up the glycosylation site may be substituted or deleted, even though the asparagine residues remain unchanged, in order to prevent glycosylation by eliminating the glycosylation recognition site.

Additionally, unglycosylated PTP λ polypeptides which have the glycosylation sites of a native molecule may be produced in recombinant prokaryotic cell culture because prokaryotes are incapable of introducing glycosylation into polypeptides.

Glycosylation variants may be produced by selecting appropriate host cells or by in vitro methods. Yeast and insect cells, for example, introduce glycosylation which varies significantly from that of mammalian systems. Similarly, mammalian cells having a different species (e.g. hamster, murine, porcine, bovine or ovine), or tissue origin (e.g. lung, liver, lymphoid, mesenchymal or epidermal) than the source of the PTP λ polypeptide are routinely screened for the ability to introduce variant glycosylation as characterized for example by elevated levels of mannose or variant ratios of mannose, fucose, sialic acid, and other sugars typically found in mammalian glycoproteins. In vitro processing of the PTP λ typically is accomplished by enzymatic hydrolysis, e.g. neuraminidase digestion.

G. Covalent Modification of PTP λ Polypeptides

Covalent modifications of PTP λ polypeptides are included within the scope herein. Such modifications are traditionally introduced by reacting targeted amino acid residues of the PTP λ polypeptides with an organic derivatizing agent that is capable of reacting with selected sides or terminal residues, or by harnessing mechanisms of post-translational modifications that function in selected recombinant host cells. The resultant covalent derivatives are useful in programs directed at identifying residues important for biological activity, for immunoassays of the PTP λ polypeptide, or for the preparation of anti-PTP λ antibodies for immunoaffinity purification of the recombinant. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R'—N═C═N—R') such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl, threonyl or tyrosyl residues, methylation of the α-amino groups of lysine, arginine, and histidine side chains (T. E. Creighton, *Proteins: Structure and Molecular Properties*, W. H. Freeman & Co., San Francisco, pp. 79–86 [1983]), acetylation of the N-terminal amine, and amidation of any C-terminal carboxyl group. The molecules may further be covalently linked to nonproteinaceous polymers, e.g. polyethylene glycol, polypropylene glycol or polyoxyalkylenes, in the manner set forth in U.S. Ser. No. 07/275,296 or U.S. Pat. Nos. 4,640,835; 4,496,689; 4,301,144; 4,670,417; 4,791,192 or 4,179,337.

Derivatization with bifunctional agents is useful for preparing intramolecular aggregates of PTP λ polypeptides with polypeptides as well as for cross-linking the PTP λ polypeptide to a water insoluble support matrix or surface for use in assays or affinity purification. In addition, a study of interchain cross-links will provide direct information on conformational structure. Commonly used cross-linking agents include 1,1-bis(diazoacetyl)-2-phenylethane, glutaraldehyde, N-hydroxysuccinimide esters, homobifunctional imidoesters, and bifunctional maleimides. Derivatizing agents such as methyl-3-[(p-azidophenyl)dithio] propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl, threonyl or tyrosyl residues, methylation of the α-amino groups of lysine, arginine, and histidine side chains [T. E. Creighton, *Proteins: Structure and Molecular Properties*, W.H. Freeman & Co., San Francisco, pp. 79–86 (1983)].

Further derivatives of the PTP λ polypeptides herein are the so-called "immunoadhesins", which are chimeric antibody-like molecules combining the functional domain(s) of a binding protein (usually a receptor, a cell-adhesion molecule or a ligand) with the an immunoglobulin sequence. The most common example of this type of fusion protein combines the hinge and Fc regions of an immunoglobulin (Ig) with domains of a cell-surface receptor that recognizes a specific ligand. This type of molecule is called an "immunoadhesin", because it combines "immune" and "adhesion" functions; other frequently used names are "Ig-chimera", "Ig-" or "Fc-fusion protein", or "receptor-globulin."

To date, more than fifty immunoadhesins have been reported in the art. Immunoadhesins reported in the literature include, for example, fusions of the T cell receptor (Gascoigne et al., *Proc. Natl. Acad. Sci. USA* 84, 2936–2940 [1987]); CD4 (Capon et al., *Nature* 337, 525–531 [1989]; Traunecker et al., *Nature* 339, 68–70 [1989]; Zettmeissl et al., *DNA Cell Biol. USA* 9, 347–353 [1990]; Byrn et al., *Nature* 344, 667–670 [1990]); L-selectin (homing receptor) (Watson et al., *J. Cell. Biol.* 110, 2221–2229 [1990]; Watson et al., *Nature* 349, 164–167 [1991]); E-selectin [Mulligan et al., *J. Immunol.* 151, 6410–17 [1993]; Jacob et al., *Biochemistry* 34, 1210–1217 [1995]); P-selectin (Mulligan et al., supra; Hollenbaugh et al., *Biochemistry* 34, 5678–84 [1995]); ICAM-1 (Stauton et al., *J. Exp. Med.* 176, 1471–1476 [1992]; Martin et al., *J. Virol.* 67, 3561–68 [1993]; Roep et al., *Lancet* 343, 1590–93 [1994]); ICAM-2 (Damle et al., *J. Immunol.* 148, 665–71 [1992]); ICAM-3 (Holness et al., *J. Biol. Chem.* 270, 877–84 [1995]); LFA-3 (Kanner et al., *J. Immunol.* 148, 2-23-29 [1992]); L1 glycoprotein (Doherty et al., *Neuron* 14, 57–66 [1995]); TNF-R1 (Ashkenazi et al., *Proc. Natl. Acad. Sci. USA* 88, 10535–539 [1991]; Lesslauer et al., *Eur. J. Immunol.* 21, 2883–86 [1991]; Peppel et al., *J. Exp. Med.* 174, 1483–1489 [1991]); TNF-R2 (Zack et al., *Proc. Natl. Acad. Sci. USA* 90, 2335–39 [1993]; Wooley et al., *J. Immunol.* 151, 6602–07 [1993]); CD44 [Aruffo et al., *Cell* 61, 1303–1313 (1990)]; CD28 and B7 [Linsley et al., *J. Exp. Med.* 173, 721–730 (1991)]; CTLA-4 [Lisley et al., *J. Exp. Med.* 174, 561–569 (1991)]; CD22 [Stamenkovic et al., *Cell* 66. 1133–1144 (1991)]; NP receptors [Bennett et al., J. Biol. Chem. 266, 23060–23067 (1991)]; IgE receptor α [Ridgway and Gorman, *J. Cell. Biol.* 115, abstr. 1448 (1991)]; HGF receptor [Mark, M. R. et al., 1992, *J. Biol. Chem.* submitted]; IFN-γR α- and β-chain [Marsters et al., *Proc. Natl. Acad. Sci. USA* 92, 5401–05 [1995]); trk-A, -B, and -C (Shelton et al., *J. Neurosci.* 15, 477–91 [1995]); IL-2 (Landolfi, *J. Immunol.* 146, 915–19 [1991]); IL-10 (Zheng et al., *J. Immunol.* 154, 5590–5600 [1995]).

The simplest and most straightforward immunoadhesin design combines the binding region(s) of the 'adhesin' protein with the hinge and Fc regions of an immunoglobulin heavy chain. Ordinarily, when preparing the PTP λ-immunoglobulin chimeras of the present invention, nucleic acid encoding the desired PTP λ polypeptide will be fused C-terminally to nucleic acid encoding the N-terminus of an immunoglobulin constant domain sequence, however N-terminal fusions are also possible. Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The precise site at which the fusion is made is not critical; particular sites are well known and may be selected in order to optimize the biological activity, secretion or binding characteristics of the PTP λ-immunoglobulin chimeras.

In a preferred embodiment, the sequence of a native, mature PTP λ polypeptide, or a soluble (transmembrane domain-inactivated) form thereof, is fused to the N-terminus of the C-terminal portion of an antibody (in particular the Fc domain), containing the effector functions of an immunoglobulin, e.g. IgG-1. It is possible to fuse the entire heavy chain constant region to the PTP λ sequence. However, more preferably, a sequence beginning in the hinge region just upstream of the papain cleavage site (which defines IgG Fc chemically; residue 216, taking the first residue of heavy chain constant region to be 114 [Kobet et al., supra], or analogous sites of other immunoglobulins) is used in the fusion. In a particularly preferred embodiment, the PTP λ sequence (full length or soluble) is fused to the hinge region and CH2 and CH3 or CH1, hinge, CH2 and CH3 domains of an IgG-1, IgG-2, or IgG-3 heavy chain. The precise site at which the fusion is made is not critical, and the optimal site can be determined by routine experimentation.

In some embodiments, the PTP λ-immunoglobulin chimeras are assembled as multimers, and particularly as homodimers or -tetramers (WO 91/08298). Generally, these assembled immunoglobulins will have known unit structures. A basic four chain structural unit is the form in which IgG, IgD, and IgE exist. A four unit is repeated in the higher molecular weight immunoglobulins; IgM generally exists as a pentamer of basic four units held together by disulfide bonds. IgA globulin, and occasionally IgG globulin, may also exist in multimeric form in serum. In the case of multimer, each four unit may be the same or different.

Various exemplary assembled PTP λ-immunoglobulin chimeras within the scope herein are schematically diagramed below:

(a) $AC_L$-$AC_L$;

(b) $AC_H$-[$AC_H$, $AC_L$-$AC_H$, $AC_L$-$V_HC_H$, or $V_LC_L$-$AC_H$];

(c) $AC_L$-$AC_H$-[$AC_L$-$AC_H$, $AC_L$-$V_HC_H$, $V_LC_L$-$AC_H$, or $V_LC_L$-$V_HC_H$];

(d) $AC_L$-$V_HC_H$-[$AC_H$, or $AC_L$-$V_HC_H$, or $V_LC_L$-$AC_H$];

(e) $V_LC_L$-$AC_H$-[$AC_L$-$V_HC_H$, or $V_LC_L$-$AC_H$]; and (f) $[A\text{-}Y]_n$-$[V_LC_L\text{-}V_HC_H]_2$, wherein each A represents identical or different novel PTP λ polypeptide amino acid sequences;

$V_L$ is an immunoglobulin light chain variable domain;

$V_H$ is an immunoglobulin heavy chain variable domain;

$C_L$ is an immunoglobulin light chain constant domain;

$C_H$ is an immunoglobulin heavy chain constant domain;

n is an integer greater than 1;

Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed as being present in the ordinary locations which they occupy in the immunoglobulin molecules.

Alternatively, the PTP λ amino acid sequences can be inserted between immunoglobulin heavy chain and light chain sequences such that an immunoglobulin comprising a chimeric heavy chain is obtained. In this embodiment, the PTP λ polypeptide sequences are fused to the 3' end of an immunoglobulin heavy chain in each arm of an immunoglobulin, either between the hinge and the CH2 domain, or between the CH2 and CH3 domains. Similar constructs have been reported by Hoogenboom, H. R. et al., *Mol. Immunol.* 28, 1027–1037 (1991).

Although the presence of an immunoglobulin light chain is not required in the immunoadhesins of the present invention, an immunoglobulin light chain might be present either covalently associated to a PTP λ-immunoglobulin heavy chain fusion polypeptide, or directly fused to the PTP λ polypeptide. In the former case, DNA encoding an immunoglobulin light chain is typically coexpressed with the DNA encoding the PTP λ-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Method suitable for the preparation of such structures are, for example, disclosed in U.S. Pat. No. 4,816,567 issued Mar. 28, 1989.

In a preferred embodiment, the immunoglobulin sequences used in the construction of the immunoadhesins of the present invention are from an IgG immunoglobulin heavy chain constant domain. For human immunoadhesins, the use of human IgG-1 and IgG-3 immunoglobulin sequences is preferred. A major advantage of using IgG-1 is that IgG-1 immunoadhesins can be purified efficiently on immobilized protein A. In contrast, purification of IgG-3 requires protein G, a significantly less versatile medium. However, other structural and functional properties of immunoglobulins should be considered when choosing the Ig fusion partner for a particular immunoadhesin construction. For example, the IgG-3 hinge is longer and more flexible, so it can accommodate larger 'adhesin' domains that may not fold or function properly when fused to IgG-1. While IgG immunoadhesins are typically mono- or bivalent, other Ig subtypes like IgA and IgM may give rise to dimeric or pentameric structures, respectively, of the basic Ig homodimer unit. Multimeric immunoadhesins are advantageous in that they can bind their respective targets with greater avidity than their IgG-based counterparts. Reported examples of such structures are CD4-IgM (Traunecker et al., supra); ICAM-IgM (Martin et al., *J. Virol.* 67, 3561–68 [1993]); and CD2-IgM (Arulanandam et al., *J. Exp. Med.* 177, 1439–50 [1993]).

For PTP λ-lg immunoadhesins, which are designed for in vivo application, the pharmacokinetic properties and the effector functions specified by the Fc region are important as well. Although IgG-1, IgG-2 and IgG-4 all have in vivo half-lives of 21 days, their relative potencies at activating the complement system are different. IgG-4 does not activate complement, and IgG-2 is significantly weaker at complement activation than IgG-1. Moreover, unlike IgG-1, IgG-2 does not bind to Fc receptors on mononuclear cells or neutrophils. While IgG-3 is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG-1 has only four serologically-defined allotypic sites, two of which (G1m and 2) are located in the Fc region; and one of these sites G1m1, is non-immunogenic. In contrast, there are 12 serologically-defined allotypes in IgG-3, all of which are in the Fc region; only three of these sites (G3m5, 11 and 21) have one allotype which is nonimmunogenic. Thus, the potential immunogenicity of a γ3 immunoadhesin is greater than that of a γ1 immunoadhesin.

PTP λ-Ig immunoadhesins are most conveniently constructed by fusing the cDNA sequence encoding the PTP λ portion in-frame to an Ig cDNA sequence. However, fusion to genomic Ig fragments can also be used (see, e.g. Gascoigne et al., *Proc. Natl. Acad. Sci. USA* 84, 2936–2940 [1987]; Aruffo et al., *Cell* 61, 1303–1313 [1990]; Stamenkovic et al., *Cell* 66, 1133–1144 [1991]). The latter type of fusion requires the presence of Ig regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques.

Other derivatives comprise the novel peptides of this invention covalently bonded to a nonproteinaceous polymer. The nonproteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol.

The PTP λ polypeptides may be linked to various nonproteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

The PTP λ polypeptides may be entrapped in microcapsules prepared, for example, by coacervation techniques or by interfacial polymerization, in colloidal drug delivery systems (e.g. liposomes, albumin microspheres, microemulsions, nano-particles and nanocapsules), or in macroemulsions. Such techniques are disclosed in *Remington's Pharmaceutical Sciences,* 16th Edition, Oslo, A., Ed. (1980).

H. Anti-PTP λ Antibody Preparation (i) Polyclonal antibodies

Polyclonal antibodies to a PTP λ molecule generally are raised in animals by multiple subcutaneous (sc) or intraperitoneal (ip) injections of the PTP λ and an adjuvant. It may be useful to conjugate the PTP λ or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

Animals are immunized against the immunogenic conjugates or derivatives by combining 1 mg or 1 μg of conjugate (for rabbits or mice, respectively) with 3 volumes of Freud's complete adjuvant and injecting the solution intradermally at multiple sites. One month later the animals are boosted with 1/5 to 1/10 the original amount of conjugate in Freud's complete adjuvant by subcutaneous injection at multiple sites. 7 to 14 days later the animals are bled and the serum is assayed for anti-PTP λ antibody titer. Animals are boosted until the titer plateaus. Preferably, the animal boosted with the conjugate of the same PTP λ, but conjugated to a different protein and/or through a different cross-linking reagent. Conjugates also can be made in recombinant cell culture as protein fusions. Also, aggregating agents such as alum are used to enhance the immune response.

(ii) Monoclonal antibodies

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies.

For example, the anti-PTP λ monoclonal antibodies of the present invention may be made using the hybridoma method first described by Kohler & Milstein, Nature 256:495 (1975), or may be made by recombinant DNA methods [Cabilly, et al., U.S. Pat. No. 4,816,567].

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-PTP λ monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a PTP λ polypeptide and another antigen-combining site having specificity for a different antigen.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin; biotin; radioactive isotopic labels, such as, e.g., $^{125}I$, $^{32}P$, $^{14}C$, or $^{3}H$, or an enzyme, such as alkaline phosphatase, beta-galactosidase or horseradish peroxidase.

Any method known in the art for separately conjugating the antibody to the detectable moiety may be employed, including those methods described by Hunter, et al., *Nature* 144:945 (1962); David, et al., *Biochemistry* 13:1014 (1974); Pain, et al., *J. Immunol. Meth.* 40:219 (1981); and Nygren, *J. Histochem. and Cytochem.* 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques*, pp. 147–158 (CRC Press, Inc., 1987).

(iii) Humanized antibodies

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature* 321, 522–525 (1986);

Riechmann et al., *Nature* 332, 323–327 (1988); Verhoeyen et al., *Science* 239, 1534–1536 (1988)], by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed Aug. 21, 1992, which is a continuation-in-part of application Ser. No. 07/715,272 filed Jun. 14, 1991.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al, *Proc. Natl. Acad. Sci. USA* 90, 2551–255 (1993); Jakobovits et al., *Nature* 362, 255–258 (1993).

(iv) Bispecific antibodies

Bispecific antibodies are monoclonal, preferably human or humanized, antibodies that have binding specificities for at least two different antigens. In the present case, one of the binding specificities is for a PTP λ polypeptide, the other one is for any other antigen. Methods for making bispecific antibodies are known in the art.

Traditionally, the recombinant production of bispecific antibodies is based on the coexpression of two immunoglobulin heavy chain-light chain pairs, where the two heavy chains have different specificities (Millstein and Cuello, *Nature* 305, 537–539 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO 93/08829 (published May 13, 1993), and in Traunecker et al., *EMBO* 10, 3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, and second and third constant regions of an immunoglobulin heavy chain (CH2 and CH3). It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in PCT application WO 94/04690 published Mar. 3, 1994.

For further details of generating bispecific antibodies see, for example, Sureshet al., *Methods in Ezymology* 121, 210 (1986).

(v) Heteroconjugate antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

I. Peptide and Non-Peptide Analogs of PTP λ Polypeptides

Peptide analogs of the PTP λ polypeptides of the present invention are modeled based upon the three-dimensional structure of the native polypeptides. Peptides may be synthesized by well known techniques such as the solid-phase synthetic techniques initially described in Merrifield, *J. Am. Chem. Soc.* 15, 2149–2154 (1963). Other peptide synthesis techniques are, for examples, described in Bodanszky et al., Peptide Synthesis, John Wiley & Sons, 2nd Ed., 1976, as well as in other reference books readily available for those skilled in the art. A summary of peptide synthesis techniques may be found in Stuart and Young, Solid Phase Peptide Synthelia, Pierce Chemical Company, Rockford, Ill. (1984). Peptides may also be prepared by recombinant DNA technology, using a DNA sequence encoding the desired peptide.

In addition to peptide analogs, the present invention also contemplates non-peptide (e.g. organic) compounds which display substantially the same surface as the peptide analogs of the present invention, and therefore interact with other molecules in a similar fashion.

J. Use of the PTP λ Polypeptides

The PTP λ polypeptides of the present invention are useful for a variety of purposes. For example, the PTP λ polypeptides of the present invention are useful in the identification and purification of the PTP λ ligand, for which a possible location is the brain. The purification may be performed by using the native receptor(s) or immunoadhesins, comprising a fusion of the extracellular domain of the receptor(s) to an immunoglobulin heavy chain constant region. The ligands are expected to be useful in the treatment of paralytic-type diseases.

An increased level of expression of the PTP λ receptors of the present invention may be useful in reducing metastasis of various tumors of the lung and other organs. The expression of the receptor may be upregulated by anti-PTP λ antibodies, which are capable of cross-linking and thereby activating the receptors. Non-antibody cross-liking agents may also be employed for this purpose.

The PTP λ polypeptides of the present invention are also useful as molecular markers of the tissues in which they are specifically expressed. As such, the PTP λ polypeptide is useful for tissue typing of specific mammalian tissues.

Native PTP λ polypeptides and their functional equivalents are also useful in screening assays designed to identify agonists or antagonists of native PTP λ polypeptides. Such assays may take the form of any conventional cell-type or biochemical binding assay, and can be performed in a variety of assay formats well known to those skilled in the art. An example is the so called "two-hybrid" assay format using the Matchmaker Two-Hybrid System (Clontech) according to the manufacturers instructions.

The native PTP λ polypeptides of the present invention are also useful as protein molecular weight markers for protein gels.

Nucleic acids encoding the PTP λ polypeptides of the present invention are also useful in providing hybridization probes for searching cDNA and genomic libraries for the coding sequence of other PTP λ polypeptides analogs in other species.

Antagonists of the PTP λ polypeptide of the present invention are useful for inhibiting the biological activity of the enzyme, thereby inhibiting the biological effects of tyrosine dephosphorylation. Agonists of the PTP λ polypeptide are useful for increasing or simulating the biological effects of the native PTP λ polypeptide.

K. Materials and Methods

1. RNA Isolation and Polymerase Chain Reaction

Messenger RNA was isolated from the non-adherent $Lin^{lo}CD34^{hi}$ fraction of fetal yolk sac cells (Micro-FastTrack, InVitrogene). Poly A RNA was reverse transcribed with random hexamers (Promega) and Molony murine Leukemia virus reverse transcriptase (SuperScript II, GIBCO BRL). One quarter of this cDNA was amplified by PCR using degenerate mixed oligonucleotide primers. Sense and anti-sense primers corresponding to the amino acid sequences (H/D)FWRM(I/V)W (SEQ ID NO:5) (5'-A(C/T)TT(C/T)TGG(A/C)GIATG(A/G)TITGG-3') (SEQ ID NO:6) and WPD(F/H)GVP (SEQ ID NO:7) (5'-GGIAC(G/A)(T/A)(G/A)(G/A)TCIG GCCA-3') (SEQ ID NO:8) respectively were used. PCR was carried out in 1×Taq DNA polymerase buffer (GIBCO BRL) plus 0.2 mM of each dNTP, 10% DMSO and 5 units Taq polymerase (GIBCO BRL) for 25 cycles of 94° C. for 1 minute, 55° C. for 1 minute and 72° C. for 1 minute. The PCR products were treated with Klenow enzyme (New England Biolabs) at 30° C. for 30 minutes, cloned into the SmaI site of the pRK-5 plasmid (Genentech, Inc.) and subsequently sequenced (Sequenase, USB).

2. Isolation of cDNA clones

Adapter-linked double stranded cDNA was prepared from λ+RNA of day-10 mice embryos (Marathon-ready cDNA synthesize kit, Clontech) using either random hexamer or oligo dT primers. Full-length cDNA was isolated by 5' or 3' rapid amplification of cDNA ends (RACE) of the marathon-ready cDNAs. A lambda cDNA library of adult mouse lung was screened following the standard protocol using cDNA fragments isolated by RACE as probes.

3. Bacterial Expression of GST-PTP Fusion Protein cDNA sequences encoding amino acids 791 to 1436 or amino acids 43 to 741 containing either the cytoplasmic region or the extracellular region of PTP λ was obtained by PCR. PCR fragments were then treated with SalI and NotI restriction enzymes and cloned into the pGEX-4T-1 plasmid (Pharmacia). Fusion proteins were affinity purified using Glutathione sepharose columns (Pharmacia). Polyclonal anti-serum against either the cytoplasmic (Cy) or extracellular (Ex) region was generated by immunizing rabbits with each purified GST-fusion protein.

4. Indirect Immunofluorescence of PC-12 Cells

NGF-treated or untreated PC-12 cells grown on cover slips were fixed with 4% formaldehyde and 0.1% Triton X-100 in phosphate-buffered saline (PBS) and permeabilized with 0.05% saponin. Fixed cells were then blocked with 10% normal goat serum plus 0.05% NP40 in PBS, incubated with polyclonal rabbit anti-Cy primary antiserum (1:3000 dilution), washed, and incubated with phycoerytherin (PE)-tagged goat antibody to rabbit immunoglobulin G. Cells were viewed and digital images were taken by fluorescence confocal microscopy.

5. Immunoprecipitation and Tyrosine Phosphatase Assay of PTPλ

PC-12 cells expressing endogenous PTP λ were washed in cold PBS, then lysed in buffer containing 50 mM Tris-HCl, pH 8.0, 150 mM NaCl, 1 mM EDTA, 1 mM EGTA, 1 mM DTT, 1 mM benzamidine, 1 mg/ml leupeptin, 1 mg/ml aprotinin, 10 mM NaF, 0.5 mM okadaic acid, 10% (v/v) glycerol, 1% (v/v) Triton X-100, 0.5% (w/v) sodium deoxycholate and 0.01% (w/v) SDS (AUTHOR?, *EMBO J.,* 13(16):3763–3771 (1994)). Cell lysates were precleared by incubating with 50 ml of washed protein A-Sepharose beads (Pharmacia). Precleared lysate was then incubated with protein A-Sepharose beads pre-coupled with rabbit polyclonal antiserum (20 ml serum/50 ml beads) at 40° C. for 15 hours. The protein A-Sepharose/PTP λ immunoprecipitate complex was then processed as described (Jiang et al., *Mol. Cell Biol.* 13(5):2942–2951 (1993)). Briefly, the complex was washed four times with HNTG buffer (20 mM HEPES, pH 7.5, 150 mM NaCl, 10% glycerol, 0.1% Triton X-100) and once with M7.6 buffer (60 mM Tris-HCl, pH 7.6, 5 mM EDTA, 10 mM DTT, 50 mM NaCl, 50 mg/ml bovine serum albumin). Washed immunoprecipitate complex was resuspended in M7.6 buffer and subject to non-radioactive protein tyrosine phosphatase assay with synthetic oligopeptide substrates (PPS1 corresponds to the hirudin 53–63 C-terminal fragment: Biotin-DGDFEEIPEEY-$PO_4$ (SEQ ID NO:9), PPS2 corresponds to amino acids 1–17 of human gastrin: Biotin-EGPWLEEEEEAY-$PO_4$ (SEQ ID NO:10)). PTPase assay was carried out following the manufacturer's procedures (Tyrosine Phosphatase Assay Kit, Boehringer Mannheim).

6. Northern Analysis

A 2.5 kb cDNA fragment encoding the cytoplasmic region of PTP λ was used to probe the murine multi-tissue northern blots (Clontech) or the A+RNA of PC-12 cells.

7. In Situ Hybridization

Rat E15.5 embryos and P1 brains were immersion fixed overnight at 4° C. in 4% paraformaldehyde, then cryoprotected overnight in 15% sucrose. Adult rat brains were fresh frozen with powdered dry ice. All tissues were sectioned at 16 um, and processed for in-situ hybridization for PTP λ using $^{33}$P-UTP labeled RNA probes. Sense and antisense probes were synthesized from a 2.5 kb DNA fragment of PTP λ using SP6 or T7 polymerase, respectively.

Further experimental details will be apparent from the following non-limiting examples.

L. Examples

EXAMPLE 1

Isolation and Characterization of the cDNA encoding PTP λ

In order to isolate novel receptor protein tyrosine phosphatases (PTPs) expressed in murine primitive hematopoietic cells, we undertook the cloning of PCR fragments produced by priming with sequences directed against conserved protein motifs found in PTPs from a number of different genes and species (Dixon, *Ann. Ny. Acad. Sci.* 766:18–22 (1995)). Analysis of 70 different PCR-derived subclones revealed an array of previously described PTPs, as well as two novel PTPs. One of these novel PTPs, termed PTP HSC, is a member of the PTP PEST family of enzymes, and it has been previously described (Cheng et al., *Blood*, in press). The second novel PCR fragment was homologous to PTPs κ and μ, both related receptor-type PTPs that mediate homophilic adhesion (Brady-Kalnay et al., *Curr. Opin. Cell. Biol.* 7(5):650–657 (1995)).

In order to further characterize the cDNA encoding this novel PTP, a combined cloning approach that utilized RACE as well as cloning from phage cDNA libraries was performed. The composite cDNA (SEQ ID NO:1) and derived protein (SEQ ID NO:2) sequences determined from these various clones is shown in FIGS. 1A–1D. The ATG start codon utilized for translation of this large open reading frame was embedded within a consensus Kozak sequence, and there are several translational stop codons upstream of this initiator codon. As can be seen from FIGS. 1A–1D, the protein (SEQ ID NO:2) derived from this cDNA (SEQ ID NO:1) is a large receptor-like molecule of 1,436 amino acids and a molecular weight of approximately 161,176 daltons.

FIGS. 2A–2B illustrate that the novel, hematopoietically-derived PTP-related protein reported here shows a high degree of homology to both PTP κ (˜60%) and PTP μ (˜53%) throughout their entire lengths (Jiang et al., (1993) supra and Gebbink et al., (1991) supra). Because this novel PTP is homologous throughout its entire length to PTPs κ and μ, it appears that the new PTP polypeptide contains MAM, IgG, 4 fibronectin type III, and two cytoplasmically localized phosphatase domains (see FIGS. 2A–2B) (Brady-Kalnay et al., *Curr. Opin. Cell. Biol.* 7(5):650–657 (1995), Jiang et al., (1993) supra and Gebbink et al., (1991) supra). These homologies with the novel PTP polypeptide are somewhat less than the homology between PTP κ and μ, (˜62%), suggesting that the novel PTP polypeptide reported here is rather more distantly related to these two PTPs than they are to each other. These data suggest that this novel PTP is the third member of the homotypically interacting PTP family containing PTPs κ and μ, and we have therefore named the novel receptor PTP λ.

As can be seen from FIG. 3, the relative sequence homologies in each of the domains of these three enzymes suggests that they are indeed closely related. Interestingly, previous data suggested that both the MAM and IgG domains mediated specific homotypic adhesion between PTPs κ and μ (Brady-Kalnay et al., (1994) supra and Zondag et al., (1995) supra), and it is clear from the sequence comparisons between these three related proteins that these two domains are substantially homologous. However, the fact that there are a large number of sequence changes between these two motifs is also consistent with the supposition that they can mediate specific homotypic interactions. Thus, it is likely that, while these motifs are undoubtedly structurally related, differences in their relative sequences are involved with homotypic recognition.

The overall sequence homologies between the three proteins is also relatively high in the FnIII domains, although the homology in the first of these domains is significantly higher than in the others. Previous work has also demonstrated that a juxtamembrane site between the transmembrane domain and the first phosphatase domain is distantly homologous to a similar region in the cadherins (Brady- Kalnay et al., *J. Cell. Biol.* 130(4):977–986 (1995)), and this site shows a high degree of homology between these three receptors. A high degree of sequence homology is also found between the first PTPase domains of these three receptors, with a somewhat lower level of homology between the second PTPase domains of these proteins. This latter result may be significant, since it has been reported that the first phosphatase domain is the most important enzymatic motif of the dual phosphatase regions in the receptor PTPs (Pot et al., *J. Biol. Chem.* 266(29):19688–19696 (1991)). The homology between these PTPase domains includes many of the residues previously found to be important for substrate recognition and tyrosine dephosphorylation in the PTP 1B (Jia et al., *Science* 268(5218):1754–1758 (1995)), although not all of these residues are completely conserved. In summary, the sequence homologies between these three proteins suggest a common ancestor as well as potentially similar functions.

EXAMPLE 2

Analysis of the Enzymatic Activity of PTP λ

In order to analyze the enzymatic activity of the PTPase domains of the novel PTP λ polypeptide, we immunoprecipitated the enzyme from PC 12 cells which we show below express the protein. In these experiments, a polyclonal antibody directed against the entire cytoplasmic domain as predicted from the cDNA sequence was produced by injecting rabbits with a GST fusion containing this region of the receptor. The immunoprecipitate was incubated with a tyrosine phosphorylated peptide using a commercial kit, and the degree of dephosphorylation was determined using an anti-phosphotyrosine antibody. As is shown in FIG. 4, the immunoprecipitate obtained using the immune serum had clear phosphatase activity, while the preimmune serum immunoprecipitate showed no such activity. In addition, FIG. 4 demonstrates that this enzymatic activity was completely inhibited by the inclusion of vanadate, a potent tyrosine phosphatase inhibitor. Thus, the PTP λ polypeptide encoded by the cDNA (SEQ ID NO:1) described herein and shown in FIGS. 1A–1D is clearly a receptor tyrosine phosphatase protein.

EXAMPLE 3

Tissue Expression of the PTP λ Transcript

As is shown in FIG. 5, northern blot analysis of fetal as well as adult tissues demonstrates that PTP λ mRNA is expressed in a diversity of tissues outside of the hematopoietic progenitor cells from which it was originally cloned. Thus, the expression of PTP λ mRNA is detected throughout embryonic development beginning in the very early embryo at day 7. Interestingly, analysis of adult organs reveals that the PTP λ transcript is expressed specifically in only a subset of tissues. Thus, there appears to be a very high level of expression of the PTP λ polypeptide in adult brain, lung and kidney, a much decreased level in heart, skeletal muscle and testis, and a lack of obvious expression at this exposure in spleen and liver.

The high level of PTP λ expression in lung and brain, together with the lack of expression in liver, is in contrast to PTP κ, a PTP which is expressed at high levels in liver but is almost undetectable in lung and brain (Jiang et al., (1993) supra). Thus, in spite of the fact that PTP κ was originally isolated from hematopoietic stem cells, there is no obvious expression in two sites which contain hematopoietic cells, the spleen and the liver. The lack of signal in the spleen, an organ which contains mostly mature hematopoietic cells, suggests, therefore, that this receptor may be expressed specifically in earlier hematopoietic progenitor cells. Interestingly, there appears to also be an alternatively spliced transcript in the lung which is not detected in the other two organs that express this receptor at high levels nor in the embryos although the nature of this alternatively spliced transcript remains to be determined. In summary, these data demonstrate that PTP λ is specifically expressed in a subset of adult tissues, some of which are divergent from PTP κ.

EXAMPLE 4

In Situ Hybridization Analysis

We performed in-situ mRNA analysis of the rat E15.5 embryo, P1 and adult rat brain to determine potential sites of PTP λ production. The results in FIG. 6 shown that extensive PTP λ expression was observed in developing skeletal, epithelial, and neuronal structures throughout the E15.5 embryo. Systemic expression was observed in various developing skeletal elements such as vertebral perichondrium, intervertebral discs, teeth, mandible and maxilla (FIG. 6, Panels A and B). Expression of PTP λ within urogenital structures included the genital tubercle (FIG. 6, Panels A and B), urethra, and urogenital sinus (not shown). Other positive areas of PTP λ expression included the anal canal (not shown), skin, olfactory and oral epithelium, esophagus (FIG. 6, Panels A and B), pituitary (FIG. 6, Panels A, B and C), aura mater (FIG. 6, Panels A, B and D), kidney (FIG. 6, Panels A and B), and lung (FIG. 6, Panels A and B). Higher magnification reveals expression restricted to developing glomeruli in the cortical region of the kidney (FIG. 6, Panels F and G), and bronchiolar epithelium of the lung (FIG. 6, Panels H and I). Within the E15.5 embryonic nervous system, high levels of expression were observed in the developing cerebral cortex (FIG. 6, Panels A and B), floor of the midbrain, choroid plexus primordium, gigantocellular reticular nucleus of the brain stem (FIG. 6, Panels A, B and C), aura mater and spinal cord (FIG. 6, Panels A, B and D). High magnification of the spinal cord reveals highest expression of PTP λ in the ventrolateral motor column (FIG. 6, Panel D).

In P1 and adult brain, expression of PTP λ was localized to regions derived from embryonic anlage that also contained high levels of expression. For instance, expression in the embryonic midbrain preceded the high levels of PTP λ expression in the P1 and adult substantia nigra (FIG. 7, Panels C and E, respectively). Expression in the embryonic forebrain (FIG. 6, Panel A) preceded expression observed in the inner layers of the P1 and adult cortex (FIG. 7, Panels A, B and D, E, respectively). Expression in the choroid plexus primordia of the embryo begets high levels of expression in the P1 brain (FIG. 7, Panel A), and low levels of expression in the adult brain (FIG. 7, Panel D).

In general, PTP λ expression in the adult brain appears to be downregulated relative to the P1 brain (FIG. 7). However, other areas of prominent expression in both P1 and adult brain include piriform cortex and endopiriform nucleus (FIG. 7, Panels A and D, respectively), amygdaloid nuclei, subiculum, and CAT, CA2 and, to a lesser extent, CA3 of the hippocampal formation (FIG. 7, Panels B and E, respectively). The P1 brain also exhibits strong expression throughout the septal area, basal ganglia, thalamus, and midbrain (FIG. 7, Panels A, B and C). Weak expression is observed in the adult superior colliculus as well as scattered expression throughout the thalamus (FIG. 7, Panel E).

EXAMPLE 5

Expression of PTP λ in PC 12 Cells

The expression of PTP λ in various regions throughout the embryonic, neonatal and adult brain suggested that this receptor might be expressed in PC12 cells, a cell line which is derived from a neural pheochromocytoma. Indeed, the immunoprecipitation experiments described in Example 2 above demonstrated enzymatic activity in anti-PTP λ precipitates derived from these cells. In addition, these cells will differentiate and extend neurites in response to nerve growth factor, so they provided a system to test a possible role for PTP λ in this developmental transition. As is shown in FIG. 8, the novel PTP λ receptor polypeptide is indeed expressed in these neuronal progenitor cells. FIG. 8 also illustrates that treatment of these cells with NGF results in a modest upregulation (~5 fold) of the transcript encoding this receptor with relatively slow kinetics. These data are thus consistent with a role for this receptor in some aspect of neuronal differentiation in this cell line.

In order to investigate the distribution of PTP λ on PC 2 cells, immunofluorescence was performed using cells that were left untreated or were treated with NGF to induce neurite outgrowth stained with an antibody directed against the cytoplasmic domain of the PTP λ receptor. As is shown in FIG. 9, PTP λ is expressed at significant levels in both treated and untreated cells, confirming the enzymatic analysis shown in FIG. 4 and the northern blot analysis shown in FIG. 8. Perhaps more interesting, however, is the cellular distribution of the PTP λ polypeptide. As FIG. 9 shows, PTP λ is found to be partitioned on the neurites as well as on the growth cone-like structures at the neurite tips. These data are consistent with a role for this receptor in neurite function, perhaps analogous to that recently described for two different Drosophila receptor PTPs (Desai et al., supra and Kreuger et al., supra).

M. Discussion

The relative levels of tyrosine phosphorylation of a diversity of proteins is critical for the regulation of a number of activities during embryonic differentiation and throughout the life of the mammalian organism. The absolute levels of this modification are mediated through the balance of the enzymatic activities of tyrosine kinases with those of the tyrosine phosphatases. In both cases, these large families of proteins perform their roles through conserved enzymatic domains that are coupled to a plethora of specificity-determining motifs. These various motifs are found in the context of both membrane traversing, receptor-like molecules as well as intracellular forms of the enzymes.

The similarities in overall structure of the tyrosine kinases and tyrosine phosphatases suggest that they mediate their relative specific activities through the use of these various domains. In the cases of some of the receptor PTPs, the extracellular motifs are somewhat unusual in that they contain highly glycosylated regions with currently unknown ligand specificity. Alternatively, a subset of these receptor-phosphatases also contain a diversity of domains, including immunoglobulin-like and fibronectin-like, which are associated with cell adhesion and ligand binding activities in other protein families. Among the most interesting of these types of adhesion-associated PTPs are the κ and μ, receptors which are involved with homotypic types of interactions. Earlier predictions, based upon the likely function of these receptors in mediating cell adhesion as well as their limited tissue distribution, suggested that there might be other κ and μ-like receptor PTPs with different tissue dispositions. We here report the isolation of the third member of this family of homotypically interacting receptor PTPs, PTP A, which may be associated with the construction of epithelial and neural structures during development and in the adult.

The strongest data suggesting that the novel PTP λ polypeptide described herein is homologous to the κ and μ receptors lies in the high degree of sequence conservation between these three proteins. Analysis of these three receptors clearly revealed that the novel PTP λ polypeptide of the present invention had a high degree of sequence homology with PTP κ and PTP μ throughout the entire length of the proteins. This homology included the four major types of domains contained in this family including the MAM, the immunoglobulin (IgG), the fibronectin type III (FN III) and the dual phosphatase (PTPase) domains (Jiang et al., (1993) supra and Gebbink et al., (1991) supra). Because previous data have suggested that both the MAM as well as the IgG domain appear to be involved with homotypic adhesion (Brady-Kalnay et al., (1994) supra and Zondag et al., supra), it is likely that these motifs are used for a similar function in PTP λ, a hypothesis that is consistent with a role for this receptor in cell adhesion. However, the degree of sequence homology of these domains between the herein reported PTP λ receptor and the PTP κ and PTP μ receptors is quite divergent, suggesting that the novel receptor may also specifically mediate a homophilic interaction only to itself and not to these domains in the other family members (Zondag et al., supra). As will be discussed below, these results, together with the tissue localization of this receptor, suggest that it may be involved with the formation of very specific edifices during development. It will, of course, be interesting to determine the structural aspects of these domains which are involved with homophilic binding, especially in light of the recent crystallographic analysis of one of the homophilically interacting cadherins (Shapiro et al., *Nature* 374(6520):327–337 (1995)). While it is difficult to currently interpret the significance of the conservation of the FNIII domains, which may act as spacer domains to extend the functionally critical MAM and IgG domains from the cell surface, the conservation of the dual PTP domains lends itself to some comment. For example, the higher degree of conservation of the first domain as compared to the second substantiates previous work suggesting that the N-terminal PTPase motif is the enzymatically active one, while the C-terminal domain may be involved with the regulation of enzyme activity (Pot et al., supra). We have attempted, without success, to bacterially express enzymatically active forms of the PTPase domains of PTP λ under conditions which gave a high level of activity with another PTP, the PTP HSC (Cheng et al., supra) (J. Cheng and L. Lasky-unpublished observations). These negative data, which of course might be technical, suggest that the PTP λ polypeptide may require an activation event, although it is clear from the immunoprecipitation studies with PC 12 cells that this receptor is endowed with enzymatic activity. Finally, previous data have suggested a role for this category of receptor PTPs in cadherin/catenin regulation, and other investigators have pointed to an intracellular, juxtamembrane site with significant homology to a similarly localized region in the cadherins (Brady-Kalnay et al., *Curr. Opin. Cell. Biol.* 7(5):650–657 (1995) and Brady-Kalnay et al., *J. Cell. Biol.* 130(4):977–986 (1995)). We have also found a very high degree of sequence conservation in this region, again consistent with a potential role for this domain in cadherin interactions. In summary, the data reported here are consistent with PTP λ being the third member of the homotypically interacting receptor PTP family.

The in situ hybridization analysis of the expression of PTP λ in the developing embryo and adult suggest some potentially important hypotheses. The expression of this receptor in a diversity of developing skeletal areas as well as in epithelial sites which line various organ systems with a layer of these cells, coupled with the proposed role for PTP $\mu$ (Brady-Kalnay et al., *Curr. Opin. Cell. Biol.* 7(5):650–657 (1995) and Brady-Kalnay et al., *J. Cell. Biol.* 130(4):977–986 (1995)), and potentially PTP κ, in the control of cadherin adhesion suggests that the novel PTP λ might be involved in a similar type of adhesion control in the developing embryo. For example, the development of epithelial layers in the lung bronchioles and kidney glomeruli requires that a sheet of epithelial cells that is one cell thick be constructed. Thus, as the cells grow and migrate during embryogenesis, they would require a mechanism where they sensed the location of other epithelial cells that were in contact with them, so that this cellular contiguity initiated an adhesive response that inhibited further epithelial movement via the enhancement of cell adhesion. One mechanism that would provide for such a sensing phenomenon would be that proposed by Tonks and colleagues (Brady-Kalnay et al., *Curr. Opin. Cell. Biol.* 7(5):650–657 (1995) and Brady-Kalnay et al., *J. Cell. Biol.* 130(4):977–986 (1995)). In this hypothesis, the $\mu$ receptor PTP comes into homophilic contact with another $\mu$ receptor PTP on an adjacent cell, and this contact upregulates cadherin-mediated adhesion through the dephosphorylation of the cadherin/catenin complex. The formation of single cell-thick epithelial structures in these embryonic organs could be mediated by a similar type of sensing mechanism using PTP κ. The expression of this receptor PTP in bone forming chondrocytes would also be expected to perform a similar type of sensing and adhesion function to assemble these structures, although this type of anatomy, which is more complex than the thin-walled epithelial-like morphology described above, would be expected to involve more elaborate types of sensing and adhesive mechanisms. Finally, because many common types of tumors of the lung and other organs involve epithelial cells, it is possible that disruptions in the proposed function of this type of adhesion sensing mechanism might be involved with the disorganized morphology and high rate of metastasis of these tumors (Kemler, supra and Beherens et al., supra). Together, these hypotheses suggest a critical role for PTP λ in the formation of various epithelial-like structures in the embryo.

Recent data from the Drosophila system also suggest interesting possibilities for the function of PTP λ in the developing nervous system (Desai et al., supra and Kreuger et al., supra). In these reports, three different Drosophila receptor PTPs, termed DPTP69D, DPTP99A and DLAR, which all contain IgG and fibronectin type III adhesion domains similar to those found in PTP λ, were shown to be critically involved with neuronal pathfinding in the developing nervous systems. Thus, mutations in either of these receptors resulted in a loss of the ability of certain neural subsets to become reoriented during their formation in the embryo. Because PTP λ is expressed in a number of developing neural sites, it is possible that it plays a similar role in the pathfinding of nerves in mammals. Thus, the expression of this PTP in the developing midbrain, forebrain, and other neural sites would dispose it to function as a mediator of pathfinding in these maturing systems. Interestingly, the expression of this receptor in these embryonic anlage was confirmed by expression in the adult sites which arise from these embryonic structures. However, the expression in the adult appeared to be somewhat reduced as compared to that observed in the embryo, and it was far more organized. These data suggest that this enzyme might be utilized during adult neuronal formation, although the apparent decrease in adult expression suggests a potentially more critical role during embryogenesis. The observed expression of this receptor in neuronal progenitor PC 12 cells, coupled with the upregulation of the transcript during neurite formation in response to NGF in these cells, also agrees with a role for this receptor PTP during neural pathfinding. Indeed, the observation that this PTP is expressed on neurites as well as on the growth-cone like structures at the tips of these processes is consistent with a potential role for this receptor in neuronal pathfinding in the mammalian nervous system. However, the relatively slow kinetics of upregulation suggest that this may be a late function. Finally, while the clear observation of the loss of pathfinding in Drosophila will be difficult to recapitulate in the mouse, due to the relatively high complexity of the mammalian nervous system, it will nevertheless be potentially of interest to examine the formation of the nervous system in animals which have been made null for the expression of this receptor.

In summary, the data reported herein demonstrate the existence of a third member of the family of receptor PTPs, PTP λ, that appear to be involved with homotypic adhesion and, potentially, cadherin mediated organ formation. The role that this novel receptor might play in the formation of epithelial sheets and neuronal structures remains to be determined. However, the existence of three of these types of receptors further suggests that this growing family may be involved with the specific formation of various types of complex structures during development as well as in the adult.

N. Concluding Remarks

The foregoing description details specific methods which can be employed to practice the present invention. Having detailed such specific methods, those skilled in the art will well enough known how to devise alternative reliable methods at arriving at the same information in using the fruits of the present invention. Thus, however, detailed the foregoing may appear in text, it should not be construed as limiting the overall scope thereof; rather, the ambit of the present invention is to be determined only by the lawful construction of the appended claims. All documents cited herein are expressly incorporated by reference.

What is claimed is:

1. An assay for identifying an antagonist or agonist of a protein tyrosine phosphatase polypeptide which comprises:

(a) contacting a phosphatase domain of a protein tyrosine phosphatase λ polypeptide with a candidate antagonist or agonist, wherein said protein tyrosine phosphatase λ polypeptide which dephosphorylates phosphorylated tyrosine residues and comprises an amino acid sequence selected from the group consisting of:

(1) the amino acid sequence shown in FIG. 1 (SEQ ID NO:2); and (2) an amino acid sequence which is encoded by a nucleic acid molecule that hybridizes under stringent conditions to a nucleic acid that encodes the amino acid sequence shown in FIG. 1 (SEQ ID NO:2); and (b) monitoring the ability of said phosphatase domain to dephosphorylate phosphorylated tyrosine residues.

2. The assay according to claim 1, wherein said protein tyrosine phosphatase λ polypeptide comprises the amino acid sequence shown in FIG. 1 (SEQ ID NO:2).

3. The assay according to claim 1, wherein said protein tyrosine phosphatase λ polypeptide is of human origin.

4. The assay according to claim 1, wherein said protein tyrosine phosphatase λ polypeptide is of murine origin.

* * * * *